US012718905B2

(12) United States Patent
Tsalik et al.

(10) Patent No.: US 12,718,905 B2
(45) Date of Patent: Aug. 25, 2026

(54) METHODS FOR CHARACTERIZING INFECTIONS AND METHODS FOR DEVELOPING TESTS FOR THE SAME

(71) Applicant: Biomeme, Inc., Philadelphia, PA (US)

(72) Inventors: Ephraim L. Tsalik, Cary, NC (US); Ricardo Henao Giraldo, Durham, NC (US); Benjamin Charles Schneller, Cary, NC (US); Donna G. Crenshaw, Durham, NC (US); Christopher Woods, Durham, NC (US)

(73) Assignee: Biomeme, Inc., Philadelphia, PA (US)

( * ) Notice: Subject to any disclaimer, the term of this patent is extended or adjusted under 35 U.S.C. 154(b) by 153 days.

(21) Appl. No.: 18/442,694

(22) Filed: Feb. 15, 2024

(65) Prior Publication Data

US 2024/0363197 A1 Oct. 31, 2024

Related U.S. Application Data

(63) Continuation of application No. PCT/US2022/040557, filed on Aug. 17, 2022.

(60) Provisional application No. 63/233,811, filed on Aug. 17, 2021.

(51) Int. Cl.
*G16B 25/10* (2019.01)
*G16H 50/70* (2018.01)

(52) U.S. Cl.
CPC ............. *G16B 25/10* (2019.02); *G16H 50/70* (2018.01)

(58) Field of Classification Search
None
See application file for complete search history.

(56) References Cited

U.S. PATENT DOCUMENTS

| | | | |
|---|---|---|---|
| 8,445,208 B2 * | 5/2013 | Shimada | C12Q 1/6883 435/6.1 |
| 8,476,200 B2 | 7/2013 | Russwurm et al. | |
| 8,821,876 B2 | 9/2014 | Ginsburg et al. | |

(Continued)

FOREIGN PATENT DOCUMENTS

| | | |
|---|---|---|
| EP | 3316875 A1 | 5/2018 |
| JP | 2007522819 A | 8/2007 |

(Continued)

OTHER PUBLICATIONS

Dix et al. Biomarker-based classification of bacterial and fungal whole-blood infections in a genome-wide expression study, Frontiers in Microbiology| www.frontiersin.org Mar. 1, 2015| vol. 6| Article 171.*

(Continued)

*Primary Examiner* — David J Stoltenberg
(74) *Attorney, Agent, or Firm* — Wilson Sonsini Goodrich & Rosati

(57) ABSTRACT

The present disclosure provides methods of developing a test to determine if an infection is present or absent, methods for developing a test to determine the etiology of an infection, methods of using tests to determine presence of an infection, such as infections related to sepsis, versus a non-infectious disease/disorder, such as systemic inflammatory response syndrome (SIRS), and methods of using tests to determine the etiology of an infection. Also provided are systems and computer-implemented methods of developing and using tests as set forth herein.

20 Claims, 19 Drawing Sheets

(56) References Cited

U.S. PATENT DOCUMENTS

| | | | |
|---|---|---|---|
| 9,770,170 B2 | 9/2017 | Shoemaker et al. | |
| 9,791,446 B2 | 10/2017 | Eden et al. | |
| 10,533,224 B2 | 1/2020 | Khatri et al. | |
| 12,473,597 B2 | 11/2025 | Tsalik et al. | |
| 2003/0074363 A1 | 4/2003 | Balaban et al. | |
| 2004/0097460 A1* | 5/2004 | Ivey | C12Q 1/686 435/6.16 |
| 2005/0209785 A1 | 9/2005 | Wells et al. | |
| 2008/0171323 A1 | 7/2008 | Banchereau et al. | |
| 2009/0311269 A1 | 12/2009 | Allen et al. | |
| 2010/0076691 A1 | 3/2010 | Palucka et al. | |
| 2010/0306863 A1* | 12/2010 | Colonna | A61P 31/04 800/13 |
| 2011/0076685 A1 | 3/2011 | Moeller et al. | |
| 2011/0098195 A1* | 4/2011 | Russwurm | C12Q 1/6883 435/6.15 |
| 2011/0110930 A1* | 5/2011 | Walley | A61K 31/573 514/169 |
| 2011/0312521 A1 | 12/2011 | Chaussabel | |
| 2011/0318726 A1 | 12/2011 | Shah et al. | |
| 2014/0141986 A1 | 5/2014 | Spetzler et al. | |
| 2014/0234854 A1 | 8/2014 | Blume et al. | |
| 2014/0323391 A1 | 10/2014 | Tsalik et al. | |
| 2015/0227681 A1 | 8/2015 | Courchesne et al. | |
| 2015/0284780 A1 | 10/2015 | Eley et al. | |
| 2015/0306073 A1 | 10/2015 | Pearlman et al. | |
| 2016/0097099 A1* | 4/2016 | Tsalik | C12Q 1/6883 514/169 |
| 2016/0153993 A1 | 6/2016 | Eden et al. | |
| 2016/0194715 A1 | 7/2016 | Zaas et al. | |
| 2016/0244834 A1* | 8/2016 | Ong | C12Q 1/6883 |
| 2016/0304953 A1 | 10/2016 | Chen et al. | |
| 2017/0030909 A1* | 2/2017 | Oved | G01N 27/44739 |
| 2017/0218455 A1 | 8/2017 | Steelman | |
| 2017/0235871 A1* | 8/2017 | Eden | G06F 17/18 703/2 |
| 2018/0021462 A1 | 1/2018 | Lanza et al. | |
| 2018/0135108 A1* | 5/2018 | Etchebarne | C12Q 1/6806 |
| 2019/0178888 A1* | 6/2019 | Shen-Orr | G01N 33/56972 |
| 2020/0017832 A1 | 1/2020 | Ribeiro Lemos Pereira et al. | |
| 2020/0131574 A1* | 4/2020 | Hall | G01N 33/564 |
| 2022/0299511 A1* | 9/2022 | Reyes | G01N 33/56972 |
| 2023/0036392 A1* | 2/2023 | Kim | A23L 33/40 |
| 2023/0132281 A1* | 4/2023 | Monaghan | C12Q 1/70 435/6.11 |

FOREIGN PATENT DOCUMENTS

| | | |
|---|---|---|
| JP | 7002037 B2 | 2/2022 |
| WO | WO-2012068642 A1 | 5/2012 |
| WO | WO-2013158281 A1 | 10/2013 |
| WO | WO-2014067943 A1 | 5/2014 |
| WO | WO-2015048098 A1 | 4/2015 |
| WO | WO-2016145426 A1 | 9/2016 |
| WO | WO-2017004390 A1 | 1/2017 |
| WO | WO-2017082943 A1 | 5/2017 |
| WO | WO-2018085928 A1 | 5/2018 |
| WO | WO-2018189502 A1 | 10/2018 |
| WO | WO-2020096984 A1 | 5/2020 |

OTHER PUBLICATIONS

He et al. The Optimization and Biological Significance of a 29-Host-Immune-mRNA Panel for the Diagnosis of Acute Infections and Sepsis; Journal of Personalized Medicine, 2021, 11, 735. https://doi.org/10.3390/jpm11080735.*

Ahn, Sun Hee. et al. Gene expression-based classifiers identify *Staphylococcus aureus* infection in mice and humans. PloS one 8(1):e48979, 1-16 (2013).

Angus, D C. et al. Epidemiology of severe sepsis in the United States: analysis of incidence, outcome, and associated costs of care. Crit Care Med 29(7):1303-1310 (2001).

Anderson, Suzanne T. et al. Diagnosis of childhood tuberculosis and host RNA expression in Africa. New England Journal of Medicine 370(18):1712-1723 (2014).

Banchereau, Romain. et al. Host immune transcriptional profiles reflect the variability in clinical disease manifestations in patients with *Staphylococcus aureus* infections. PloS One 7(4):e34390, 1-11 (2012).

Berry, Matthew P R. et al. An interferon-inducible neutrophil-driven blood transcriptional signature in human tuberculosis. Nature 466(7309):973-977 (2010).

Bishop, Christopher M. Pattern Recognition and Machine Learning. Springer (2006). Book Review only.

Bloom, Chloe I. et al. Transcriptional blood signatures distinguish pulmonary tuberculosis, pulmonary sarcoidosis, pneumonias and lung cancers. PloS One 8(8):e70630, 1-17 (2013).

Bone, et al., Definitions for sepsis and organ failure and guidelines for the use of innovative therapies in sepsis. Chest, 101:1644-1655, (1992).

Bukrinsky, Michael I. et al. Active nuclear import of human immunodeficiency virus type 1 preintegration complexes. Proceedings of the National Academy of Sciences 89(14):6580-6584 (1992).

Bustin. Quantification of mRNA using real-time reverse transcription PCR (RT-PCR): trends and problems. J Mol Endocrinol 29(1):23-39 (2002).

Cantrell, Ron. et al. Antibiotic prescribing in ambulatory care settings for adults with colds, upper respiratory tract infections, and bronchitis. Clinical therapeutics 24(1):170-182 (2002).

ClinicalTrials.gov Identifier: NCT00258869. Observational Study of Sepsis and Pneumonia to Develop Diagnostic Tests, Record created Nov. 23, 2005. pp. 1-22. [retrieved on Dec. 31, 2024] Available at URL: https://clinicaltrials.gov/study/NCT00258869?cond=NCT00258869&rank=1.

Cosgrove, Sara E. The relationship between antimicrobial resistance and patient outcomes: mortality, length of hospital stay, and health care costs. Clinical infectious diseases 15:42 Suppl 2:S82-S89 (2006).

Fawcett, Tom. An introduction to ROC analysis. Pattern Recognition Letters 27(8):861-874 (2006).

Fleming-Dutra, Katherine E. et al. Prevalence of Inappropriate Antibiotic Prescriptions Among US Ambulatory Care Visits, 2010-2011. JAMA 315(17):1864-1873 (2016).

Friedman et al.: Regularization paths for generalized linear models via coordinate descent. J Stat Softw. 33(1):1-22 (2010).

Ghildyal, Reena. et al. Nuclear import of the respiratory syncytial virus matrix protein is mediated by importin β1 independent of importin alpha. Biochemistry 44(38):12887-12895 (2005).

Glickman, Seth W. et al. Disease progression in hemodynamically stable patients presenting to the emergency department with sepsis. Academic emergency medicine 17(4):383-390 (2010).

Goerke, Christiane et al., Quantification of Bacterial Transcripts during Infection Using Competitive Reverse Transcription-PCR (RT-PCR) and LightCycler RT-PCR. Clinical and Diagnostic Laboratory Immunology pp. 279-282 (2001).

Gould, I.M. Antibiotic resistance: the perfect storm. International journal of antimicrobial agents (34):S2-S5 (2009).

Greijer, et al. Multiplex real-time NASBA for monitoring expression dynamics of human cytomegalovirus encoded IE1 and pp67 RNA. J Clin Virol. Feb. 2002;24(1-2):57-66.

Hadwiger, Lee A., et al., Fungal mitochondrial DNases: effectors with the potential to activate plant defenses in nonhost resistance. Phytopathology. 103(1): 81-90 (2013).

Hellemans, Jan. et al. qBase relative quantification framework and software for management and automated analysis of real-time quantitative PCR data. Genome Biology 8(2):R19, 1-14 (2007).

Herberg, Jethro A. et al. Transcriptomic profiling in childhood H1N1/09 influenza reveals reduced expression of protein synthesis genes. The Journal of Infectious Diseases 208(10):1664-1668 (2013).

Hesse-Macabata, Jana, et al., Tryptanthrin promotes keratinocyte and fibroblast responses in vitro after infection with Trichophyton benhamiae DSM6916. Scientific Reports 10(1): Article 1863 (2020).

Hu, R. et al. Series GSE40396, Whole blood transcriptional signature distinguishes viral infection from bacterial infection in febrile

(56) References Cited

OTHER PUBLICATIONS young children. Record created Aug. 27, 2012. pp. 1-2. [retrieved on Dec. 31, 2024] Available at URL:https://www.ncbi.nlm.nih.gov/geo/query/acc.cgi?acc=GSE40396.
Huang, et al. Temporal dynamics of host molecular responses differentiate symptomatic and asymptomatic influenza a infection. PLoS Genet. Aug. 2011;7(8):e1002234. doi: 10.1371/journal.pgen.1002234. Epub Aug. 25, 2011.
Iyer, Kali R., et al., Treatment strategies for crypococcal infection: challenges, advances and future outlook. Nature Reviews Microbiology 19: pp. 454-466 (2021).
Jain, Seema. et al. Community-Acquired Pneumonia Requiring Hospitalization among U.S. Adults. N Engl J Med 373(5):415-427 (2015).
Jansen, Rogier R. et al. Frequent detection of respiratory viruses without symptoms: toward defining clinically relevant cutoff values. Journal of clinical microbiology 49(7):2631-2636 (2011).
Kaforou, Myrsini. et al. Detection of tuberculosis in HIV-infected and-uninfected African adults using whole blood RNA expression signatures: A case-control study. PLoS Medicine 10(10):e1001538, 1-18 (2013).
Kim, J.H., and H A Gallis. et al. Observations on spiraling empiricism: its causes, allure, and perils, with particular reference to antibiotic therapy. The American journal of medicine 87(2):201-206 (1989).
Kodani, Maja, et al. Application of TaqMan Low-Density Arrays for Simultaneous Detection of Multiple Respiratory Pathogens. Journal Of Clinical Microbiology pp. 2175-2182 (2011).
Kumar, Swati and Kelly J Henrickson. Update on influenza diagnostics: lessons from the novel H1N1 influenza A pandemic. Clinical microbiology reviews 25(2):344-361 (2012).
Labatut, Vincent, and Hocine Cherifi. Accuracy measures for the comparison of classifiers. arXiv preprint arXiv:1207.3790 (2012). (Year: 2012).
Langley, Raymond J. et al. An integrated clinico-metabolomic model improves prediction of death in sepsis. Science Translational Medicine 5(195):195ra95, 1-18 (2013).
Liu, Vincent. et al. Hospital deaths in patients with sepsis from 2 independent cohorts. JAMA 312(1):90-92 (2014).
Lytkin, Nikita I. et al. Expanding the understanding of biases in development of clinical-grade molecular signatures: a case study in acute respiratory viral infections. PloS one 6(6):e20662, 1-10 (2011).
Madan, Ichchha, et al. The peripheral whole-blood transcriptome of acute pyelonephritis in human pregnancy. J Perinat. Med. 42(1): 31-53 (2014).
Martin, Greg S. et al. The epidemiology of sepsis in the United States from 1979 through 2000. N Engl J Med 348(16):1546-1554 (2003).
Mchugh, Leo. et al. A Molecular Host Response Assay to Discriminate Between Sepsis and Infection-Negative Systemic Inflammation in Critically Ill Patients: Discovery and Validation in Independent Cohorts. PLoS Med 12(12):e1001916, 1-35 (2015).
Mcnemar, Quinn. Note on the sampling error of the difference between correlated proportions or percentages. Psychometrika 12(2):153-157 (1947).
Meacci, Elisabetta, et al., Cytohesin-1, a cytosolic guanine nucleotide-exchange protein for ADP-ribosylation factor. Proc. Natl. Acad. Sci. USA pp. 1745-1748 (1997).
Mejias, Asuncion. et al. Whole blood gene expression profiles to assess pathogenesis and disease severity in infants with respiratory syncytial virus infection. PLoS medicine 10(11):e1001549, 1-20 (2013).
Opal, Steven M. et al. The next generation of sepsis clinical trial designs: what is next after the demise of recombinant human activated protein C?*. Crit Care Med 42(7):1714-1721 (2014).
Pena, Olga M. et al. An Endotoxin Tolerance Signature Predicts Sepsis and Organ Dysfunction at Initial Clinical Presentation. EBioMedicine 1(1):64-71 (2014).
Puskarich, Michael A. et al. Outcomes of patients undergoing early sepsis resuscitation for cryptic shock compared with overt shock. Resuscitation 82(10):1289-1293 (2011).
Schappert, Susan M., and Elizabeth A. Rechtsteiner. Ambulatory medical care utilization estimates for 2007. Vital and Health Statistics. Series 13, Data from the National Health Survey 169:1-38 (2011).
Severino, Patricia. et al. Patterns of gene expression in peripheral blood mononuclear cells and outcomes from patients with sepsis secondary to community acquired pneumonia. PloS One 9(3):e91886, 1-8 (2014).
Shapiro, Daniel J. Antibiotic prescribing for adults in ambulatory care in the USA, 2007-09. The Journal of antimicrobial chemotherapy 69(1):234-240 (2014).
Steinbrink, Julie M. et al. The host transcriptional response to Candidemia is dominated by neutrophil activation and heme biosynthesis and supports novel diagnostic approaches. Genome medicine 13(1):108, 1-13 (2021).
Subramanian, T. et al. Interaction of CtBP with adenovirus E1A suppresses immortalization of primary epithelial cells and enhances virus replication during productive infection. Virology. 443(2): 313-320 (2013).
Thach, D.C. Surveillance of transcriptomes in basic military trainees with normal, febrile respiratory illness, and convalescent phenotypes. Genes and immunity 6(7):588-595 (2005).
Tsalik, Ephraim L. et al. Discriminative value of inflammatory biomarkers for suspected sepsis. J Emerg Med 43(1):97-106 (2012). Published Online Nov. 6, 2011.
Tsalik, Ephraim L. et al. Multiplex PCR to diagnose bloodstream infections in patients admitted from the emergency department with sepsis. Journal of clinical microbiology 48(1):26-33 (2010). Published Online Oct. 21, 2009.
Varlamov, Dmitriy A. et al. Combinations of PCR and Isothermal Amplification Techniques Are Suitable for Fast and Sensitive Detection of SARS-CoV-2 Viral RNA. Frontiers in Bioengineering and Biotechnology (2020).
Woods, Christopher W. A host transcriptional signature for presymptomatic detection of infection in humans exposed to influenza H1N1 or H3N2. PloS one 8(1):e52198, 1-9 (2013).
Yates, Frank. Contingency tables involving small numbers and the $\chi$ 2 test. Supplement to the Journal of the Royal Statistical Society 1(2):217-235 (1934).
Athar, et al., ArrayExpress update—from bulk to single-cell expression data, Nucleic Acids Res., 47(D1):D711-D715, (2019).
Australian Examination Report corresponding to AU 2016288208; dated Oct. 27, 2020 (6 pages).
Australian Examination Report corresponding to AU 2016288208; dated Sep. 29, 2021 (4 pages).
Barrett, et al., NCBI GEO: archive for functional genomics data sets—update, Nucleic Acids Res., 41 (Database issue):D991-995, (2013).
Canadian Office Action corresponding to CA 2,989,199; mailed Sep. 21, 2022 (7 pages).
Canadian Office Action corresponding to CA 2,989,199; mailed Aug. 8, 2023 (5 pages).
Chinese Office Action corresponding to CN 201680038489.9; dated Oct. 19, 2020 (12 pages, including English translation.
Chinese Office Action corresponding to CN 201680038489.9; mailed Mar. 31, 2020 (20 pages including English translation).
Chinese Rejection Decision corresponding to 201680038489.9; issued Mar. 2, 2022 (15 pages, including English translation).
Colvin, Joshua M., et al., "Detection of Viruses in Young Children With Fever Without an Apparent Source", Pediatrics 130(6): e1455-e1462 (2012).
European Office Action corresponding to EP Application No. 21207860.4; dated Nov. 3, 2023 (4 pages).
European Search Report corresponding to European Patent Application No. 16818801.9, dated Nov. 22, 2018, 12 pages.
Extended European Search Report corresponding to EP 21207860.4; dated Feb. 25, 2022 (11 pages).
Gliddon, Harriet D., et al., "Genome-wide host RNA signatures of infectious diseases: discovery and clinical translation", Immunology 153.2, 2018, 171-178.

(56) References Cited

OTHER PUBLICATIONS

Hu, Xinran , et al., "Gene expression profiles in febrile children with defined viral and bacterial infection", PNAS, 110 (31), 2013, 12792-12797.
International Preliminary Report on Patentability issued in PCT/US2022/040557, dated Feb. 13, 2024.
International Search Report and Written Opinion issued in PCT/US2022/040557, mailed Dec. 28, 2022.
International Search Report and Written Opinion, PCTUS2016/040437, mailed Oct. 4, 2016.
Japanese Decision of Rejection corresponding to JP 2021-135662, issued Apr. 21, 2023 (9 pages, including English translation).
Japanese Office Action corresponding to JP 2017-568212; dated Jul. 17, 2020 (11 pages, including English translation).
Japanese Office Action corresponding to JP 2017-568212; dated Apr. 23, 2021 (20 pages, including English translation).
Japanese Office Action corresponding to JP 2021-135662; dated Aug. 9, 2022 (8 pages, including English translation).
Kozera, et al., Reference genes in real-time Pcr, J. Appl. Genet., 54(4):391-406, (2013).
Parnell, Grant P., et al., "A distinct influenza infection signature in the blood transcriptome of patients with severe community-acquired pneumonia", Critical Care, 16(Article No. R157), 2012, 1-12.
Ramilo, Octavio , et al., "Gene expression patterns in blood leukocytes discriminate patients with acute infections", Blood, 109(5), 2007, 2066-2077.
Rao, Sakshi, et al., "Recent trends in molecular techniques for food pathogen detection", Chemical Analysis of Food, Techniques and Applications, 2020, 177-285 (abstract only).
Singer, et al., The third international consensus definitions for sepsis and septic shock (sepsis-3), JAMA, 315(8):801-810, (2016).
Stone, Judy , "Under The Weather? A Drop Of Blood Can Tell If Antibiotics Are Needed", Retrieved from Forbes: http://onforb.es/1ZBQ9MM (5 pages), 2016.
Tang, Collin HH, et al., Non-invasive classification of severe sepsis and systemic inflammatory response syndrome using a nonlinear support vector machine: a preliminary study, Physiological Measurement 31:775-793, 2010.
Tsalik, Ephraim L., et al., "Host gene expression classifiers diagnose acute respiratory illness etiology", Science Translational Medicine, 8(322): 322ra11, 2016, 1-10.
Tsalik, Ephraim L., et al., "Supplementary Materials for "Host gene expression classifiers diagnose acute respiratory illness etiology"", Science Translational Medicine, 8(322): 322ra11 (24 pages), 2016.
Wang, et al., RNA-Seq: a revolutionary took for transcriptomics, Nat. Rev. Genet., 10(1):57-63, (2009).
Zaas, Aimee K., et al., "Gene expression signatures diagnose influenza and other symptomatic respiratory viral infections in humans", Cell Host Microbe, 6(3), 2009, 207-217.
Zaas, Aimee K., et al., "The current epidemiology and clinical decisions surrounding acute respiratory infections", Trends in Molecular Medicine, 20(10), 2014, 579-588.
Zaas, Aimee K., et al., "Supplementary Materials for "Gene Expression Signatures Diagnose Influenza and Other Symptomatic Respiratory Viral Infections in Humans"", Cell Host & Microbe, 6(3) (17 pages), 2009.
Zaas, et al., A host-based RT-PCR gene expression signature to identify acute respiratory viral infection, Sci. Transl. Med., 5(203):203ra126, (2013).
Ramilo, et al., Gene expression patterns in blood leukocytes discriminate patients with acute infections, Blood, 109 (5):2066-2077, (2007), including Supplemental Data: Table S2: Influenza A versus bacterial infection; class comparison results.
Lin, Gu-Lung. et al. Epidemiology and Immune Pathogenesis of Viral Sepsis. Frontiers in immunology 9:2147, 1-21 (2018).
Sweeney, Timothy E., and Purvesh Khatri. Benchmarking Sepsis Gene Expression Diagnostics Using Public Data. Critical care medicine 45(1):1-10 (2017).
Sweeney, Timothy E. et al. Unsupervised Analysis of Transcriptomics in Bacterial Sepsis Across Multiple Datasets Reveals Three Robust Clusters. Critical care medicine 46(6):915-925 (2018).
Tolle, Angelika. et al. Identification of microRNAs in blood and urine as tumour markers for the detection of urinary bladder cancer. Oncology reports 30(4):1949-1956 (2013).
U.S. Appl. No. 18/324,475 Office Action dated Sep. 2, 2025.
Zubakov, Dmitry. et al. Stable RNA markers for identification of blood and saliva stains revealed from whole genome expression analysis of time-wise degraded samples. International journal of legal medicine 122(2):135-142 (2008).

* cited by examiner

| | Infection | No Infection |
|---|---|---|
| Infection | 49 | 6 |
| No Infection | 8 | 37 |

FIG. 16

| Metric | Value |
|---|---|
| Accuracy | 59.0% |
| AUC Bacteria | 0.81 |
| AUC Viral | 0.84 |
| AUC SIRS | 0.8 |
| AUC Healthy | 0.97 |
| AUC Fungal | 0.7 |

| | Bacterial | Viral | Fungal | SIRS | Healthy |
|---|---|---|---|---|---|
| **Bacterial** | 13 | 5 | 1 | 4 | 2 |
| **Viral** | 4 | 12 | 0 | 3 | 2 |
| **Fungal** | 3 | 1 | 0 | 4 | 1 |
| **SIRS** | 2 | 1 | 0 | 17 | 5 |
| **Healthy** | 0 | 0 | 1 | 2 | 17 |

FIG. 18

METHODS FOR CHARACTERIZING INFECTIONS AND METHODS FOR DEVELOPING TESTS FOR THE SAME

CROSS REFERENCE

This application is a continuation of International Patent Application No. PCT/US2022/040557, filed on Aug. 17, 2022, which claims the benefit of U.S. Provisional Patent Application No. 63/233,811, filed on Aug. 17, 2021, which is incorporated by reference in its entirety.

BACKGROUND

The WHO identified communicable diseases among the leading causes of morbidity and mortality world-wide. Infections are extraordinarily varied in their clinical manifestations, whether due to differences in pathogens (e.g., viral, bacterial, fungal), site of infection (e.g., lung, urinary tract, nervous system), host (e.g., neonatal, adolescent, elderly), geography (e.g., tropical, temperate), or socioeconomics (e.g., low/middle vs. high income) among other factors. This heterogeneity makes diagnosing and managing infections exceptionally challenging. Existing diagnostics such as culture, antigen assays, and PCR for pathogen detection each has strengths and limitations. Even when comprehensive pathogen detection testing is performed, it fails to identify the presence of infection or its cause in most cases. In the absence of readily available diagnostic information, treatment is empiric resulting in high rates of inappropriate antibiotic use, which drives the development and spread of antimicrobial resistance.

When infections go untreated or inappropriately treated, they may progress to severe forms. Sepsis is defined as life-threatening organ dysfunction resulting from a dysregulated immune response to infection. Despite its association with nearly half of all in-hospital deaths, there are still no approved therapies specific for sepsis. Identifying sepsis requires two major elements: evidence of end-organ dysfunction and evidence of infection. End-organ dysfunction is readily identified using standard measures of kidney, liver, cardiac, respiratory, neurologic, metabolic, and hematologic function. However, the identification of infection poses far greater challenges. Although tests such as blood culture can be performed to identify a pathogen, such tests are time consuming often taking days to come back. Furthermore, about 50% of patients with sepsis have a pathogen identified. Therefore, tests that identify the presence of infection can offer significant value, not only to the patient with suspected sepsis, but to any patient with suspected infection including those with mild illness encountered in the outpatient setting.

Therapies that are optimized for individual patients and that target specific sepsis mechanisms have been hard to implement because of nonspecific clinical presentations, delayed diagnosis, cryptic severity, and a heterogeneous clinical course. Patients may arrive at an emergency department with mild clinical manifestations yet rapidly progress to critical illness. Others have benign courses despite a similar onset of symptoms, suggesting that host factors play an important role in sepsis development and outcome. Given that infections account for more than 10 million emergency department visits per year, and sepsis treatment costs $16.7 billion in the United States, there exists an urgent need for more timely sepsis diagnosis, characterization, and prognosis, to inform personalized sepsis treatment of the appropriate intensity.

Sepsis itself is composed of three core components. First and foremost is the presence of infection. Second is a dysregulated immune response. These two components then interact to manifest as the third component: life-threatening organ dysfunction. Organ dysfunction can be readily identified using standard laboratory and physical examination procedures. For example, pulmonary dysfunction can be assessed by oxygenation; renal dysfunction by creatinine or urine output; or cardiac dysfunction by hemodynamic measurements. However, the most difficult element to identify is the presence of infection that leads to a dysregulated immune response and sepsis.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Recognized herein is a need to develop diagnostic host gene expression signatures that can identify the presence of infection in patients who either have suspected sepsis or are at risk for developing sepsis, and methods of using diagnostic host gene expression signatures that, for example, discriminate cases of infection (bacterial, viral, or fungal) from those without infection (SIRS or healthy), as well as the ability to identify whether the source of the infection is bacterial, viral, or fungal, and in so doing, identify patients with infection or sepsis and also identify the pathogen class responsible for the condition.

The present disclosure provides methods for the identification (e.g., diagnosis) of infection and for characterizing the etiology of infections. In some examples, methods of the present disclosure allow for the differentiation of subjects (e.g., patients) with an infection due to either bacterial, viral, and/or fungal etiologies versus subjects with non-infectious conditions or healthy controls, including the differentiation of subjects with sepsis from those with systemic inflammatory response syndrome (SIRS), for determining, for example, the etiology of infection. The present disclosure provides methods for developing tests to characterize and/or identify the nature of such.

The present disclosure also provides methods and systems for the identification of infectious disease classifiers that identify between sepsis and systemic inflammatory response syndrome (SIRS). The present disclosure also provides methods and systems for identification of infectious disease classifiers that identify among bacterial infection, viral infection, fungal infection, or a combination thereof. The methods and systems can have a single classifier that determines one or more among option outcomes (e.g., SIRS or sepsis infection including a bacterial infection, a viral infection and/or a fungal infection).

According to an aspect of the inventive concept, provided is a method for developing a test on a platform to determine presence or absence of infection in a subject including: analyzing expression levels of genes in biological sources on the platform; selecting a set of genes, wherein genes in the set are selected for having differential gene expression levels between where the infection is present, and where the infection is absent; and using expression levels of genes in a set of genes to generate a classifier for a presence or an absence of the infection, wherein the classifier can be used in the test to determine the presence or absence of infection in the subject on the platform.

According to another aspect of the inventive concept, provided is a method for developing a test on a platform to determine etiology of an infection in a subject including: analyzing expression levels for genes in biological sources on the platform; and selecting a set of genes, wherein genes in the set of genes are selected for having differential gene expression levels between when a bacterial infection is present and when the bacterial infection is absent, when a fungal infection is present and when a fungal infection is absent, and/or when a viral infection is present, and when a viral infection is absent, using expression levels for genes in the set of genes to generate a classifier for a presence or an absence of a bacterial infection, a presence or an absence of a fungal infection, and/or a presence or an absence of a viral infection, wherein the classifier can be used in the test to determine the presence or absence of a bacterial infection, the presence or absence of a fungal infection, and/or the presence or absence of a viral infection in the subject on the platform.

According to another aspect of the inventive concept, provided is a method for differentiating sepsis from systemic inflammatory response syndrome (SIRS) in a sample from a biological source including: analyzing gene expression levels in a set of genes with a classifier for a presence of sepsis versus an absence of sepsis/presence of a noninfectious illness/inflammation, wherein presence of sepsis is indicated when a score derived from the classifier for the presence of sepsis for the gene expression levels in the set of genes exceeds a cutoff and/or threshold value indicating the presence of sepsis, or the score falls within a range or band of values indicating the presence of sepsis.

According to another aspect of the inventive concept, provided is a method of detecting an infection in a sample derived from a biological source including: comparing gene expression levels of a set of genes from the sample to a classifier output indicative of presence of infection and/or a classifier output indicative of absence of infection, wherein presence of an infection is indicated when a score derived from the classifier for a presence of infection for the gene expression levels exceeds a cutoff and/or threshold value for the presence of an infection, or the score falls within a range or band indicating the presence of infection.

According to another aspect of the inventive concept, provided is a method of identifying etiology of an infection in a sample derived from a biological source comprising: comparing gene expression levels in a set of genes from the sample to classifiers to determine the etiology of the infection; and determining the etiology of the infection, wherein the etiology of the infection is indicated when a score derived from a classifier indicative of a particular etiology of infection in the set of genes exceeds a cutoff or threshold value indicative of the etiology of the infection or infections, or the score falls within a range or band indicating the presence of that infection etiology.

According to another aspect of the inventive concept, provided is a system for determining etiology of an infection in a subject including: at least one processor; a sample input circuit configured to receive a biological sample from the subject; a sample analysis circuit coupled to the at least one processor and configured to determine gene expression levels in the biological sample; an input/output (I/O) circuit coupled to the at least one processor; a storage circuit coupled to the at least one processor and configured to store data, parameters, and/or classifiers; and a memory coupled to the at least one processor including computer-readable program code stored in the memory that when executed by the at least one processor causes the at least one processor to perform operations including: controlling and/or performing measurement of gene expression levels of a set of genes in the biological sample via the sample analysis circuit; retrieving classifiers of etiology from the storage circuit; analyzing the gene expression levels of the set of genes in the biological sample with the classifiers; deriving an etiology score and/or probability from analysis of the gene expression levels of the set of genes in the biological sample with the classifiers; and controlling output by way of the I/O circuit of a determination of an etiology of the infection.

According to another aspect of the inventive concept, provided is a computer-implemented method for determining etiology of an infection in a subject including: measuring gene expression levels of a set of genes in a biological sample from the subject via a sample analysis circuit; retrieving classifiers of etiology from a storage circuit; analyzing the gene expression levels of the set of genes in the biological sample with the classifiers; deriving an etiology probability from analysis of the gene expression levels of the set of genes in the biological sample with the classifiers; and controlling output by way of an I/O circuit of a determination of an etiology of the infection.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Another aspect of the present disclosure provides methods for developing a test on a platform to determine a presence or an absence of an infection in a subject, comprising: analyzing expression levels of genes in biological sources on the platform; selecting a set of genes, wherein genes in the set are selected for having differential gene expression levels between the infection being present and the infection being absent; and using expression levels of genes in the set of genes to generate a classifier for the presence or the absence of the infection, wherein the classifier is usable in the test to determine the presence or the absence of the infection in the subject on the platform. In some embodiments, the present disclosure provides systems for developing a test on a platform to determine a presence or an absence of an infection in a subject, comprising: one or more computer processors that are individually or collectively programmed to: analyze expression levels of genes in biological sources on the platform; select a set of genes, wherein genes in the set are selected for having differential gene expression levels between the infection being present and the infection being absent; and use expression levels of genes in the set of genes to generate a classifier for the presence or the absence of the infection, wherein the classifier is usable in the test to determine the presence or the absence of the infection in the subject on the platform. In some embodiments, the present disclosure provides computer-implemented methods for training a machine learning classifier comprising: analyzing expression levels of genes in biological sources; selecting at least a subset of the genes that exhibit differential gene expression levels in subjects where an injection is present as compared to subjects where the infection is absent; and using expression levels of the subset of genes to train the machine learning classifier to differentiate between a presence or an absence of the infection in a subject.

In some embodiments, the classifier for the presence or the absence of infection comprises a signature comprising expression levels of individual genes, and a weight for each gene in the signature as determined during test development. In some embodiments, analyzing expression levels of genes comprises normalization of the expression levels of the genes against expression levels of one or more reference genes. In some embodiments, the reference gene is one of any selected from the group consisting of HPRT1, CRCP, WDR33, HIGD1A, DMTF1, UBE3A, G3BP2, PUM1, RBBP4, HNRNPM, and ZNF250, or any combination thereof. In some embodiments, the biological sources in which the infection is present and the biological sources in which the infection is absent comprise in vivo sources, ex vivo sources, or in vitro sources. In some embodiments, the test to determine the presence or the absence of the infection comprises a test to determine a presence or an absence of sepsis. In some embodiments, the test determines a presence of a non-infectious illness if an absence of sepsis is determined by the test. In some embodiments, the non-infectious illness is systemic inflammatory response syndrome (SIRS). In some embodiments, the test determines the class of infection if a presence of sepsis is determined by the test. In some embodiments, the class of infection is selected from the group consisting of a) a bacterial infection, b) a fungal infection, c) a viral infection, d) a bacterial infection and a fungal infection, e) a bacterial infection and a viral infection, f) a fungal infection and a viral infection, and g) a bacterial infection, a fungal infection, and a viral infection.

In some embodiments, the expression levels of the set of genes are obtained from assaying RNA transcription levels of genes in the set. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2IT, GNAI2, STXBP2, KLF6, SERPINB1, BID, SAR1B, EVL, CACYBP, VPS53, UGCG, CCL5, RC3H2, MPZL1, CD44, HNMT, POLC3, HNRNPA3, GABARAPL1, TM7SF3, ST3GAL5, PRKAR1A, ABHD2, KYNU, TAGLN2, PCYOX1, PSMF1, UNC45A, GMEB1, CD46, BASP1, OGFOD1, MKNK2, RXRA, AKIRIN2, and KIF18, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2IT, GNAI2, STXBP2, and KLF6, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, and GBP1, or a subset thereof.

In some embodiments, generating the classifier comprises iteratively: (i) assigning a weight for each gene expression value, entering the weight and expression value for each gene into a classifier equation and determining a score for outcome for each of the plurality of subjects, (ii) determining the accuracy of classification for each outcome across the plurality of subjects, and (iii) adjusting the weight for each gene expression value until accuracy of classification is optimized, to provide the classifier for a presence or absence of an infection for the subject on the platform, wherein genes having a non-zero weight are included in the classifier. In some embodiments, the classifier is a linear or logistic regression classifier, and wherein a score derived from the classifier is converted to a probability.

Another aspect of the present disclosure provides methods for developing a test on a platform to determine etiology of an infection in a subject comprising: analyzing expression levels for genes in biological sources on the platform; selecting a set of genes, wherein genes in the set of genes are selected for having differential gene expression levels between when a bacterial infection is present and when the bacterial infection is absent, when a fungal infection is present and when the fungal infection is absent, or when a viral infection is present, and when a viral infection is absent; and using expression levels for genes in the set of genes to generate a classifiers for a presence or an absence of a bacterial infection, a presence or an absence of a fungal infection, or a presence or an absence of a viral infection, wherein the classifiers can be used in the test to determine the presence or the absence of the bacterial infection, the presence or the absence of the fungal infection, or the presence or the absence of the viral infection in the subject on the platform. In some embodiments, the present disclosure provides systems for developing a test on a platform to determine etiology of an infection in a subject comprising: one or more computer processors that are individually or collectively programmed to: analyze expression levels for genes in biological sources on the platform; select a set of genes, wherein genes in the set of genes are selected for having differential gene expression levels between when a bacterial infection is present and when the bacterial infection is absent, when a fungal infection is present and when the fungal infection is absent, or when a viral infection is present, and when a viral infection is absent; and use expression levels for genes in the set of genes to generate a classifiers for a presence or an absence of a bacterial infection, a presence or an absence of a fungal infection, or a presence or an absence of a viral infection, wherein the classifiers can be used in the test to determine the presence or the absence of the bacterial infection, the presence or the absence of the fungal infection, or the presence or the absence of the viral infection in the subject on the platform. In some embodiments, the present disclosure provides computer-implemented methods for training a machine learning classifier, comprising: analyzing expression levels for genes in biological sources; selecting at least a subset of the genes that exhibit differential gene expression levels in subjects where a bacterial infection is present as compared to subjects where the bacterial infection is absent, in subjects where a fungal infection is present as compared to subjects where the fungal infection is absent, or in subjects where a viral infection is present as compared to subjects where a viral infection is absent; and using expression levels for the subset of genes to train the machine learning classifier to differentiate between a presence or an absence of a bacterial infection, a presence or an absence of a fungal infection, or a presence or an absence of a viral infection.

In some embodiments, classifier for a particular etiology comprises a signature comprising expression levels of individual genes, and a weight for each gene in the signature as determined during test development. In some embodiments, obtaining expression levels of genes comprises normalization of the expression levels of the genes against expression levels of one or more reference genes. In some embodiments, the one or more reference genes is selected from the group consisting of HPRT1, CRCP, WDR33, HIGD1A, DMTF1, UBE3A, G3BP2, PUM1, RBBP4, HNRNPM, and ZNF250, or any combination thereof. In some embodiments, the biological sources in which the bacterial infection is present, the biological sources in which the fungal infection is present, or the biological sources in which the viral infection is present comprise in vivo sources, ex vivo sources, or in vitro sources.

In some embodiments, the expression levels of the set of genes are obtained from assaying RNA transcription levels of genes in the set. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2I1, GNAI2, STXBP2, KLF6, SERPINB1, BID, SAR1B, EVL, CACYBP, VPS53, UGCG, CCL5, RC3H2, MPZL1, CD44, HNMT, POLC3, HNRNPA3, GABARAPL1, TM7SF3, ST3GAL5, PRKAR1A, ABHD2, KYNU, TAGLN2, PCYOX1, PSMF1, UNC45A, GMEB1, CD46, BASP1, OGFOD1, MKNK2, RXRA, AKIRIN2, and KIF18, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2I1, GNAI2, STXBP2, and KLF6, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, and GBP1, or a subset thereof.

In some embodiments, generating the classifier comprises iteratively: (i) assigning a weight for each gene expression value, entering the weight and expression value for each gene into a classifier equation and determining a score for outcome for each of the plurality of subjects, (ii) determining the accuracy of classification for each outcome across the plurality of subjects, and (iii) adjusting the weight for each gene expression value until accuracy of classification is optimized, to provide the classifier for the presence or the absence of a bacterial infection, the presence or the absence of a fungal infection, or the presence or the absence of a viral infection in the subject on the platform, wherein genes having a non-zero weight are included in the classifier for the presence or the absence of a bacterial infection, the presence or the absence of a fungal infection, and/or the presence or the absence of a viral infection. In some embodiments, the classifier is a linear or logistic regression classifier, and wherein a score derived from the classifier is converted to a probability.

Another aspect of the present disclosure provides methods for differentiating sepsis from systemic inflammatory response syndrome (SIRS) in a sample from a biological source, comprising: analyzing gene expression levels in a set of genes with a classifier for a presence of sepsis versus an absence of sepsis/presence of a noninfectious illness/inflammation, wherein the presence of sepsis is indicated when a score derived from the classifier for the presence of sepsis exceeds a cutoff or threshold value indicating the presence of sepsis, or the score falls within a range or band indicating the presence of sepsis. In some embodiments, the present disclosure provides systems for differentiating sepsis from systemic inflammatory response syndrome (SIRS) in a sample from a biological source, comprising: one or more computer processors that are individually or collectively programmed to: analyze gene expression levels in a set of genes with a classifier for a presence of sepsis versus an absence of sepsis/presence of a noninfectious illness/inflammation, wherein the presence of sepsis is indicated when a score derived from the classifier for the presence of sepsis exceeds a cutoff or threshold value indicating the presence of sepsis, or the score falls within a range or band indicating the presence of sepsis. In some embodiments, the present disclosure provides computer-implemented methods for differentiating sepsis from systemic inflammatory response syndrome (SIRS) in a sample from a biological source, comprising: analyzing gene expression levels in a set of genes with a trained machine learning classifier to detect a presence or an absence of sepsis, or a presence or an absence of a noninfectious illness or inflammation, wherein the presence of sepsis is indicated when a score derived from the trained machine learning classifier for the presence of sepsis exceeds a cutoff or threshold value or falls within a range or band of cutoff or threshold values.

In some embodiments, the classifier for the presence of sepsis comprises a signature comprising expression levels of individual genes, and a weight for each gene in the signature as determined during training. In some embodiments, presence of systemic inflammatory response syndrome (SIRS) is indicated when a score derived from the classifier for the presence of sepsis exceeds a cutoff or threshold value for the absence of sepsis, or the score falls within a range or band indicating the absence of sepsis. In some embodiments, comparing expression levels in the set of genes comprises normalization of the expression levels of genes in the set of genes against expression levels of one or more reference genes. In some embodiments, the one or more reference genes is selected from the group consisting of HPRT1, CRCP, WDR33, HIGD1A, DMTF1, UBE3A, G3BP2, PUM1, RBBP4, HNRNPM, and ZNF250, or any combination thereof.

In some embodiments, the gene expression levels in the set of genes are obtained from assaying RNA transcription levels of individual genes in the set. In some embodiments, the classifier indicative of the presence of sepsis comprises a gene signature for the presence of sepsis. In some embodiments, the classifier indicative of the absence of sepsis comprises a gene signature for the presence of systemic inflammatory response syndrome (SIRS). In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2I1, GNAI2, STXBP2, KLF6, SERPINB1, BID, SAR1B, EVL, CACYBP, VPS53, UGCG, CCL5, RC3H2, MPZL1, CD44, HNMT, POLC3, HNRNPA3, GABARAPL1, TM7SF3, ST3GAL5, PRKAR1A, ABHD2, KYNU, TAGLN2, PCYOX1, PSMF1, UNC45A, GMEB1, CD46, BASP1, OGFOD1, MKNK2, RXRA, AKIRIN2, and KIF18, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2I1, GNAI2, STXBP2, and KLF6, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, and GBP1, or a subset thereof.

In some embodiments, the sample comprises a blood sample from the biological source. In some embodiments, the biological source is a human subject.

Another aspect of the present disclosure provides methods for detecting an infection in a sample derived from a biological source comprising: analyzing gene expression levels in a set of genes with a classifier for a presence of an infection, wherein the presence of the infection is indicated when a score derived from the classifier for the presence of the infection exceeds a cutoff or threshold value for the presence of the infection. In some embodiments, the present disclosure provides systems for detecting an infection in a sample derived from a biological source comprising: one or more computer processors that are individually or collectively programmed to: analyze gene expression levels in a set of genes with a classifier for a presence of an infection, wherein the presence of the infection is indicated when a score derived from the classifier for the presence of the infection exceeds a cutoff or threshold value for the presence of the infection. In some embodiments, the present disclosure provides computer-implemented methods for detecting an infection in a sample derived from a biological source comprising: analyzing gene expression levels in a set of genes with a trained machine learning classifier to detect a presence or an absence of an infection, wherein the presence of the infection is indicated when a score derived from the trained machine learning classifier exceeds a cutoff or threshold value or falls within a range or band of cutoff or threshold values.

In some embodiments, the classifier for the presence of the infection comprises a signature comprising expression levels of individual genes and a weight for each gene in the signature as determined during training. In some embodiments, analyzing gene expression levels in the set of genes comprises normalization of the gene expression levels in the set of genes against expression levels of one or more reference genes. In some embodiments, the one or more reference genes is selected from the group consisting of HPRT1, CRCP, WDR33, HIGD1A, DMTF1, UBE3A, G3BP2, PUM1, RBBP4, HNRNPM, and ZNF250, or any combination thereof. In some embodiments, the infection is a bacterial, fungal, and/or viral infection. In some embodiments, the classifier indicative of the presence of the infection comprises a gene signature for the presence of the infection, and the classifier indicative of the absence of the infection comprises a gene signature for the absence of the infection.

In some embodiments, the expression levels of the set of genes are obtained from assaying RNA transcription levels of genes in the set. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, and GBP1, CDC42EP2, ADAP2, CHPT1, SPATS2, PGRMC2, SLC39A8, YWHAH, TNFAIP3, GLRX, IL1RAP, SPSB3, CNIH4, UBE2I1, GNAI2, STXBP2, KLF6, SERPINB1, BID, SAR1B, EVL, CACYBP, VPS53, UGCG, CCL5, RC3H2, MPZL1, CD44, HNMT, POLC3, HNRNPA3, GABARAPL1, TM7SF3, ST3GAL5, PRKAR1A, ABHD2, KYNU, TAGLN2, PCYOX1, PSMF1, UNC45A, GMEB1, CD46, BASP1, OGFOD1, MKNK2, RXRA, AKIRIN2, and KIF18 or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2I1, GNAI2, STXBP2, and KLF6, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, and GBP1, or a subset thereof.

In some embodiments, detecting the presence of the infection comprises detecting the presence of a bacterial infection. In some embodiments, detecting the presence of a bacterial infection comprises an indication of a presence of sepsis. In some embodiments, detecting the presence of the infection comprises detecting the presence of a fungal infection. In some embodiments, detecting the presence of a fungal infection comprises an indication of a presence of sepsis. In some embodiments, detecting the presence of the infection comprises detecting the presence of a viral infection. In some embodiments, detecting the presence of a viral infection comprises an indication of a presence of sepsis. In some embodiments, detecting an absence of an infection comprises an indication of the presence of a non-infectious illness or systemic inflammatory response syndrome (SIRS).

In some embodiments, the sample comprises a blood sample from the biological source. In some embodiments, the biological source is a human subject.

Another aspect of the present disclosure provides methods for identifying etiology of an infection in a sample derived from a biological source comprising: analyzing gene expression levels in a set of genes with one or more classifiers of etiology; and determining the etiology of the infection, wherein the etiology of the infection is indicated when a score derived from a classifier indicative of a particular etiology of infection exceeds a cutoff or threshold value indicative of the etiology of the infection or infections. In some embodiments, the present disclosure provides systems for identifying etiology of an infection in a sample derived from a biological source comprising: one or more computer processors that are individually or collectively programmed to: analyze gene expression levels in a set of genes with one or more classifiers of etiology; and determine the etiology of the infection, wherein the etiology of the infection is indicated when a score derived from a classifier indicative of a particular etiology of infection exceeds a cutoff or threshold value indicative of the etiology of the infection or infections. In some embodiments, the present disclosure provides computer-implemented methods for determining an etiology of an infection in a sample derived from a biological source, comprising: analyzing gene expression levels in a set of genes with one or more trained machine learning classifiers of etiology; and determining the etiology of the infection based at least in part on the analyzing, wherein the etiology of the infection is indicated when a score derived from the one or more trained machine learning classifiers exceeds a cutoff or threshold value or falls within a range or band of cutoff or threshold values.

In some embodiments, comparing expression levels in a set of genes comprises normalization of the expression levels of genes in the set of genes against expression levels of one or more reference genes. In some embodiments, the one or more reference genes is selected from the group consisting of HPRT1, CRCP, WDR33, HIGD1A, DMTF1, UBE3A, G3BP2, PUM1, RBBP4, HNRNPM, and ZNF250, or any combination thereof. In some embodiments, the classifiers of etiology comprise a bacterial infection classifier, a fungal infection classifier, a viral infection classifier, or a non-infectious illness classifier. In some embodiments, each classifier of etiology comprises a signature comprising expression levels of individual genes and a weight for each gene in the signature as determined during training.

In some embodiments, the expression levels of the set of genes are obtained from assaying RNA transcription levels of individual genes in the set of genes. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2I1, GNAI2, STXBP2, KLF6, SERPINB1, BID, SAR1B, EVL, CACYBP, VPS53, UGCG, CCL5, RC3H2, MPZL1, CD44, HNMT, POLC3, HNRNPA3, GABARAPL1, TM7SF3, ST3GAL5, PRKAR1A, ABHD2, KYNU, TAGLN2, PCYOX1, PSMF1, UNC45A, GMEB1, CD46, BASP1, OGFOD1, MKNK2, RXRA, AKIRIN2, and KIF18, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2I1, GNAI2, STXBP2, and KLF6, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, and GBP1, or a subset thereof.

In some embodiments, the etiology of the infection is a bacterial infection. In some embodiments, indication of a presence of a bacterial infection comprises an indication of sepsis. In some embodiments, detecting the presence of the infection comprises detecting the presence of a fungal infection. In some embodiments, detecting the presence of a fungal infection comprises an indication of a presence of sepsis. In some embodiments, detecting the presence of the infection comprises detecting the presence of a viral infection. In some embodiments, detecting the presence of a viral infection comprises an indication of a presence of sepsis.

In some embodiments, the sample comprises a blood sample from the biological source. In some embodiments, the biological source is a human subject.

Another aspect of the present disclosure provides a test or kit for determining etiology or presence of an infection comprising a test developed by the methods disclosed herein. In some embodiments, the present disclosure provides a test or kit for determining etiology or presence of an infection comprising a trained machine learning classifier that is trained by the methods disclosed herein.

In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2I1, GNAI2, STXBP2, KLF6, SERPINB1, BID, SAR1B, EVL, CACYBP, VPS53, UGCG, CCL5, RC3H2, MPZL1, CD44, HNMT, POLC3, HNRNPA3, GABARAPL1, TM7SF3, ST3GAL5, PRKAR1A, ABHD2, KYNU, TAGLN2, PCYOX1, PSMF1, UNC45A, GMEB1, CD46, BASP1, OGFOD1, MKNK2, RXRA, AKIRIN2, and KIF18, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2I1, GNAI2, STXBP2, and KLF6, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, and GBP1, or a subset thereof.

Another aspect of the present disclosure provides systems for determining etiology of an infection in a subject, comprising: at least one processor; a sample input circuit configured to receive a biological sample from the subject; a sample analysis circuit coupled to the at least one processor and configured to determine gene expression levels in the biological sample; an input/output (I/O) circuit coupled to the at least one processor; a storage circuit coupled to the at least one processor and configured to store data, parameters, or classifiers; and a memory coupled to the at least one processor comprising computer-readable program code stored in the memory that when executed by the at least one processor causes the at least one processor to perform operations comprising: controlling or performing measurement of gene expression levels of a set of genes in the biological sample via the sample analysis circuit; retrieving classifiers of etiology from the storage circuit; analyzing the gene expression levels of the set of genes in the biological sample with the classifiers; deriving an etiology probability from analysis of the gene expression levels of the set of genes in the biological sample with the classifiers; and controlling output of a determination of an etiology of the infection by way of the I/O circuit.

In some embodiments, the classifiers each comprise a signature comprising expression levels of individual genes and a weight for each gene in the signature as determined during training. In some embodiments, analyzing the gene expression levels of the set of genes comprises normalizing measured gene expression levels of genes in the set of genes against gene expression levels of one or more reference genes and analyzing normalized gene expression levels. In some embodiments, the one or more reference genes is selected from the group consisting of HPRT1, CRCP, WDR33, HIGD1A, DMTF1, UBE3A, G3BP2, PUM1, RBBP4, HNRNPM, and ZNF250, or any combination thereof.

In some embodiments, each classifier for a particular etiology comprises a signature comprising expression levels of individual genes and a weight for each gene in the signature as determined during training. In some embodiments, etiologies of the infection comprise bacterial infections, viral infections, fungal infections, or no infection. In some embodiments, an etiology of no infection represents a non-infectious inflammatory response. In some embodiments, the system comprises computer-readable code to transform quantitative or semi-quantitative determination of gene expression levels to a cumulative score or probability of the etiology of the infection. In some embodiments, the system comprises a set platform, a thermal cycler platform, a hybridization and multi-signal coded detector platform, a nucleic acid mass spectroscopy platform, or a nucleic acid sequencing platform, or any combination thereof.

In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2I1, GNAI2, STXBP2, KLF6, SERPINB1, BID, SAR1B, EVL, CACYBP, VPS53, UGCG, CCL5, RC3H2, MPZL1, CD44, HNMT, POLC3, HNRNPA3, GABARAPL1, TM7SF3, ST3GAL5, PRKAR1A, ABHD2, KYNU, TAGLN2, PCYOX1, PSMF1, UNC45A, GMEB1, CD46, BASP1, OGFOD1, MKNK2, RXRA, AKIRIN2, and KIF18, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2I1, GNAI2, STXBP2, and KLF6, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, and GBP1, or a subset thereof.

In some embodiments, the classifiers comprise a presence of infection classifier or an absence of infection classifier. In some embodiments, determination of the etiology of the infection comprises determination of a presence of sepsis if an infection is determined to be present, and a presence of a non-infectious illness or systemic inflammatory response syndrome (SIRS) if an infection is determined to be absent. In some embodiments, the analyzing of the gene expression levels of the set of genes in the biological sample with the classifiers comprises: a classifier reporting a score; and comparing the score to cutoff or threshold values for a score indicative of a probability or likelihood for the etiology of the infection.

Another aspect of the present disclosure provides computer implemented methods for determining etiology of an infection in a subject comprising: measuring gene expression levels of a set of genes in a biological sample from the subject via a sample analysis circuit; retrieving classifiers of etiology from a storage circuit; analyzing the gene expression levels of the set of genes in the biological sample with the classifiers; deriving an etiology probability from analysis of the gene expression levels of the set of genes in the biological sample with the classifiers; and controlling output by way of an I/O circuit of a determination of an etiology of the infection.

In some embodiments, the classifiers each comprise a signature comprising expression levels of individual genes and a weight for each gene in the signature as determined during training. In some embodiments, analyzing the gene expression levels of the set of genes comprises normalizing measured gene expression levels of genes in the set of genes against gene expression levels of one or more reference genes and analyzing normalized gene expression levels. In some embodiments, the one or more reference genes is selected from the group consisting of HPRT1, CRCP, WDR33, HIGD1A, DMTF1, UBE3A, G3BP2, PUM1, RBBP4, HNRNPM, and ZNF250, or any combination thereof. In some embodiments, the etiologies of the infection comprise bacterial infections, fungal infections, viral infections, or no infection. In some embodiments, an etiology of no infection represents a non-infectious inflammatory response. In some embodiments, quantitative or semi-quantitative measuring of gene expression levels is transformed to a cumulative score or probability of the etiology of the infection.

In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2I1, GNAI2, STXBP2, KLF6, SERPINB1, BID, SAR1B, EVL, CACYBP, VPS53, UGCG, CCL5, RC3H2, MPZL1, CD44, HNMT, POLC3, HNRNPA3, GABARAPL1, TM7SF3, ST3GAL5, PRKAR1A, ABHD2, KYNU, TAGLN2, PCYOX1, PSMF1, UNC45A, GMEB1, CD46, BASP1, OGFOD1, MKNK2, RXRA, AKIRIN2, and KIF18, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE2I1, GNAI2, STXBP2, and KLF6, or a subset thereof. In some embodiments, the set of genes comprises XAF1, DDX58, HPSE, SMOX, IDH1, GRB10, C19orf66, MKRN2, CLN8, MPZL2, ACO1, TRIM5, TRIM25, OGFRL1, EGR1, and GBP1, or a subset thereof.

In some embodiments, the classifiers comprise a classifier for a presence of an infection or a classifier for an absence of an infection. In some embodiments, determination of the etiology of the infection comprises determination of a presence of sepsis if an infection is determined to be present, and a presence of a non-infectious illness or systemic inflammatory response syndrome (SIRS) if an infection is determined to be absent. In some embodiments, the analyzing of the gene expression levels of the set of genes in the biological sample with the classifiers comprises a classifier; reporting a score; and comparing the score to cutoff or threshold values indicative of a probability or likelihood for the etiology of the infection.

Another aspect of the present disclosure provides methods for determining whether a subject has sepsis or systemic inflammatory response syndrome (SIRS), comprising: (a) measuring an expression level of one or more markers in a blood sample of said subject; (b) using a trained machine learning algorithm to process said expression level to determine that said subject has sepsis or SIRS at an accuracy of at least 80%; and (c) outputting a report indicative of said subject having sepsis or SIRS at said accuracy of at least 80%.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 16 depicts a confusion matrix for infection vs. no infection test on the Qvella FAST-HR qRT-PCR platform.

FIG. 18 depicts the performance metrics (left) and confusion matrix (right panel) for the multi-classifier system performed on the Qvella FAST-HR qRT-PCR platform.

DETAILED DESCRIPTION

Figure 1:
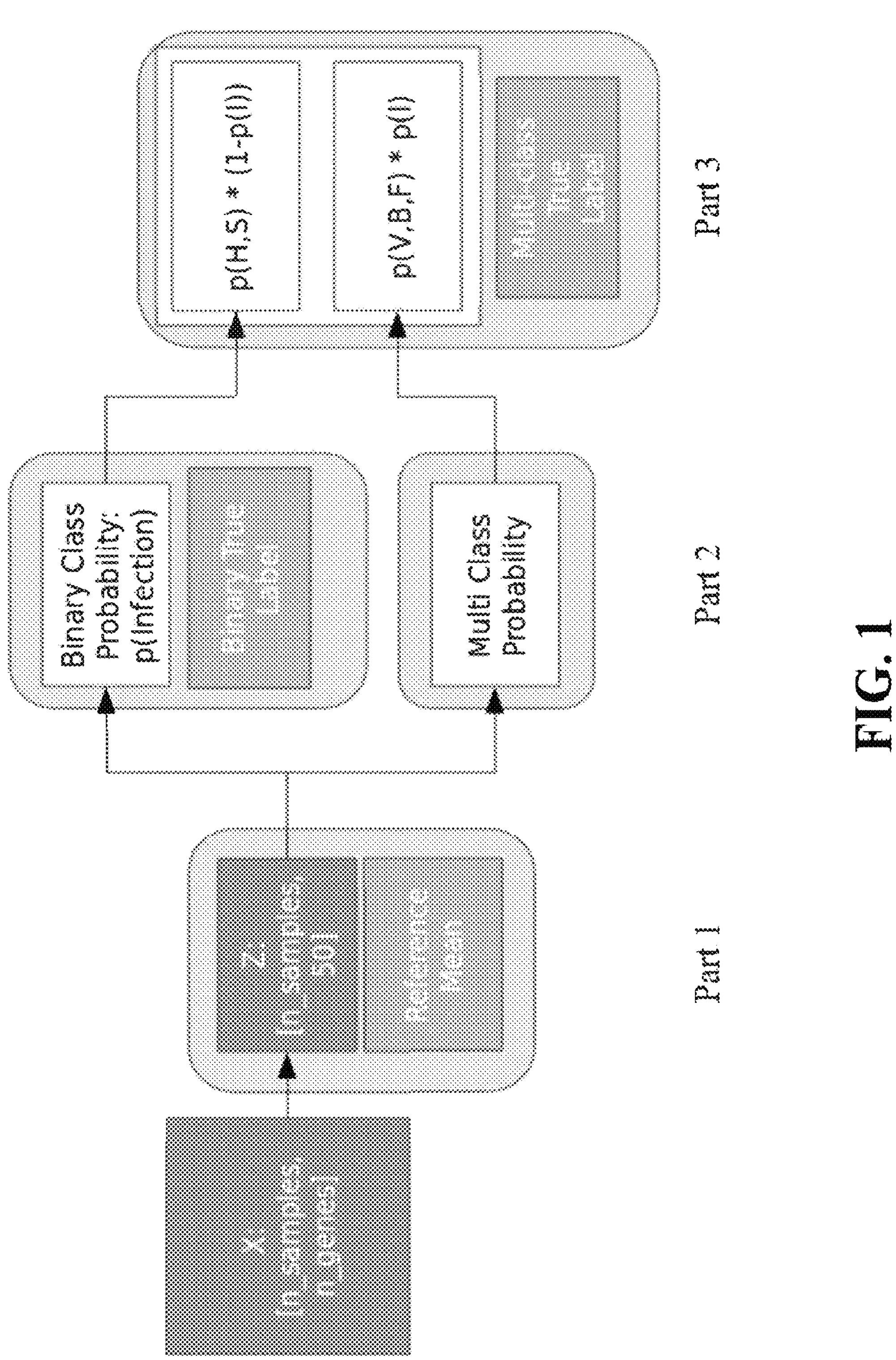
FIG. 1 depicts a schematic of the signature discovery model. The model projects the gene expression data to a lower dimensional space of dimension 50, and then branches to two decision layers (binary, multi class). The multi class predictions (bacterial, viral, fungal, SIRS or healthy) are further conditioned on the binary class predictions (infection or non-infection).

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a," "an," and "the" are used herein to refer to one or to more than one (i.e., at least one) of the grammatical object of the article. By way of example, "an element" means at least one element and can include more than one element. The term "and/or" includes any and all combinations of one, or more, of the associated listed items and may be abbreviated as "/".

Unless otherwise defined, all technical terms used herein have the same meaning as commonly understood by one of ordinary skill in the art to which this disclosure belongs.

The present disclosure provides that alterations in analyte levels, for example, gene, protein and/or metabolite expression, in blood in response to pathogen exposure that causes an infection, such as infections that lead to sepsis, can be used to identify and characterize the etiology of the infection, such as a bacterial infection, a fungal infection, a viral infection, and/or a non-infectious response, in a subject with a high degree of accuracy.

Definitions

The term “infection,” as used herein, generally refers to the invasion and/or multiplication of microorganisms such as bacteria, viruses, and parasites that are not normally present within the body. An infection may cause no symptoms and be subclinical, or it may cause symptoms and be clinically apparent. An infection may remain localized, or it may spread through the blood or lymphatic vessels to become systemic (affecting the entire body). Microorganisms that live naturally in the body are not considered infections. For example, bacteria that normally live within the mouth and intestine are not infections.

The term “sepsis,” as used herein, generally refers to a life-threatening condition that arises when a dysregulated inflammatory immune response to infection by the body causes injury to its own tissues and organs. Thus, an important distinction between infection and sepsis can be that infection does not necessarily imply sepsis, whereas sepsis can be induced by an infection (see JAMA. 2016 Feb. 23; 315(8): 801-810. for clinical definitions of sepsis and SIRS). Bacterial infections, such as, but not limited to, *Staphylococcus aureus* and *Escherichia coli* infections, are generally the most common cause of sepsis, but fungal infections, such as, but not limited to, *Candida* spp. infections, and viral infections, such as, but not limited to, Influenza and SARS-CoV-2 infections, can also lead to sepsis. In some embodiments, presence and/or etiology of an infection may be used to differentiate between the presence of sepsis, or the presence of a non-infectious illness, for example, systemic inflammatory response syndrome (SIRS), in a subject, wherein presence of an infection, for example, but not limited to, a bacterial infection can be indicative of the presence of sepsis, and absence of an infection can be indicative of SIRS.

The term “signature” or “host response signature,” as used herein, generally refers to a set of biological analytes and the measurable quantities of said analytes whose particular combination signifies the presence or absence of the specified biological state. These signatures can be discovered in a plurality of subjects with known status (e.g., with a confirmed bacterial infection, fungal infection, viral infection, or suffering from a non-infectious illness/inflammatory response), and can be discriminative (individually or jointly) of one or more categories or outcomes of interest. These measurable analytes, also known as biological markers, or biomarkers, include, but are not limited to, gene expression levels, protein or peptide levels, or metabolite levels. See also US 2015/0227681 to Courchesne et al.; US 2016/0153993 to Eden et al. In some embodiments, gene expression levels may be determined by measuring/determining nucleic acid levels, for example, by measuring/determining mRNA levels.

In some embodiments, a “signature” can be a particular combination of genes, for example, a pre-defined set, for example, genes 1-64 as ranked and set forth in Table 1, or any subset thereof, for example, but not limited to, genes 1-32, or genes 1-16, as ranked and set forth in Table 1, whose expression levels, when incorporated into a classifier as described herein, can discriminate a condition such as a bacterial infection, fungal infection, viral infection, or a non-infectious illness/inflammatory response. In some embodiments, the signature can be agnostic to the species (e.g., while differentiating between pathogen classes such as virus or bacteria or fungus, it does not differentiate between particular genus or species of virus or bacteria or fungus) and/or agnostic to the particular cause of the non-infectious illness/inflammatory response.

In some embodiments, the classifier or classifiers as described herein, can discriminate between the presence or absence of an infection. In some embodiments, the classifier or classifiers as described herein, can discriminate between the presence or absence of an infection, wherein absence of an infection can be indicative of a presence of a non-infectious illness, or can be indicative that the subject is healthy. In some embodiments, the classifier or classifiers as described herein, can discriminate between the presence or absence of an infection, wherein presence of an infection can be indicative of the presence of a bacterial infection. In some embodiments, the classifier or classifiers as described herein, can discriminate between the presence or absence of an infection, wherein presence of an infection can be indicative of the presence of a viral infection. In some embodiments, the classifier or classifiers as described herein, can discriminate between the presence or absence of an infection, wherein presence of an infection can be indicative of the presence of a fungal infection. In some embodiments, the classifier or classifiers as described herein, can discriminate between the presence or absence of an infection, wherein presence of an infection can be indicative of the presence of sepsis. In some embodiments, the classifier or classifiers as described herein, can discriminate between the presence or absence of an infection, wherein presence of an infection can be indicative of the presence of sepsis, and wherein absence of an infection can be indicative of the presence of SIRS. In some embodiments, the classifier or classifiers as described herein, can discriminate between the etiology of the infection, for example, can determine the presence or absence of a bacterial infection, the presence or absence of a fungal infection, the presence or absence of a viral infection, and/or the presence or absence of a non-infectious illness. In some embodiments, the classifier or classifiers as described herein can discriminate between presence of a bacterial infection and SIRS.

For example, a classifier can be a machine learning algorithm. The machine learning algorithm can be trained with a training set to yield a trained machine learning algorithm. Examples of machine learning algorithms include, but are not limited to: neural networks, convolutional neural networks, artificial neural networks, supervised or non-supervised machine learning algorithms, regression algorithms, instance-based algorithms, decision tree algorithms, clustering algorithms, association rule learning algorithms, deep learning algorithms, dimensionality reduction algorithms, or ensemble algorithms.

A trained machine learning algorithm can determine whether a subject has sepsis at an accuracy of at least 70%, at least 75%, at least 80%, at least 85%, at least 90%, at least 91%, at least 92% at least 93%, at least 94%, at least 95%, at least 96%, at least 97%, at least 98%, or at least 99%. A trained machine learning algorithm can determine whether a subject has SIRS at an accuracy of at least 70%, at least 75%, at least 80%, at least 85%, at least 90%, at least 91%, at least 92% at least 93%, at least 94%, at least 95%, at least 96%, at least 97%, at least 98%, or at least 99%.

A trained machine learning algorithm can output a report indicative of a subject having sepsis at an accuracy of at least 70%, at least 75%, at least 80%, at least 85%, at least 90%, at least 91%, at least 92% at least 93%, at least 94%, at least 95%, at least 96%, at least 97%, at least 98%, or at least 99%. A trained machine learning algorithm can output a report indicative of a subject having SIRS at an accuracy of at least 70%, at least 75%, at least 80%, at least 85%, at least 90%, at least 91%, at least 92% at least 93%, at least 94%, at least 95%, at least 96%, at least 97%, at least 98%, or at least 99%.

TABLE 1

The 64 genes of a host response/gene expression signature according to the inventive concept. These 64 genes are sorted in rank order by weight determined during the discovery process to identify presence or absence of infection and/or to identify the pathogen class/etiology that is the cause of infection.

| Rank order by weight in model | Gene name |
| --- | --- |
| 1 | XAF1 |
| 2 | DDX58 |
| 3 | HPSE |
| 4 | SMOX |
| 5 | IDH1 |
| 6 | GRB10 |
| 7 | C10orf66* |
| 8 | MKRN2 |
| 9 | CLN8 |
| 10 | MPZL2 |
| 11 | ACO1 |
| 12 | TRIM5 |
| 13 | TRIM25 |
| 14 | OGFRL1 |
| 15 | EGR1 |
| 16 | GBP1 |
| 17 | CDC42EP2 |
| 18 | ADAP2 |
| 19 | CHPT1 |
| 20 | SPATS2 |
| 21 | PGRMC2 |
| 22 | SLC39A8 |
| 23 | YWHAH |
| 24 | TNFAIP3 |
| 25 | GLRX |
| 26 | IL1RAP |
| 27 | SPSB3 |
| 28 | CNIH4 |
| 29 | UBE2I1 |
| 30 | GNAI2 |
| 31 | STXBP2 |
| 32 | KLF6 |
| 33 | SERPINB1 |
| 34 | BID |
| 35 | SAR1B |
| 36 | EVL |
| 37 | CACYBP |
| 38 | VPS53 |
| 39 | UGCG |
| 40 | CCL5 |
| 41 | RC3H2 |
| 42 | MPZL1 |
| 43 | CD44 |
| 44 | HNMT |
| 45 | POLC3 |
| 46 | HNRNPA3 |
| 47 | GABARAPL1 |
| 48 | TM7SF3 |
| 49 | ST3GAL5 |
| 50 | PRKAR1A |
| 51 | ABHD2 |
| 52 | KYNU |
| 53 | TAGLN2 |
| 54 | PCYOX1 |
| 55 | PSMF1 |
| 56 | UNC45A |
| 57 | GMEB1 |
| 58 | CD46 |
| 59 | BASP1 |
| 60 | OGFOD1 |

TABLE 1-continued

The 64 genes of a host response/gene expression signature according to the inventive concept. These 64 genes are sorted in rank order by weight determined during the discovery process to identify presence or absence of infection and/or to identify the pathogen class/etiology that is the cause of infection.

| Rank order by weight in model | Gene name |
| --- | --- |
| 61 | MKNK2 |
| 62 | RXRA |
| 63 | AKIRIN2 |
| 64 | KIF18 |

*Aliases for C19orf66: Chromosome 19 Open Reading Frame 66, Repressor of Yield of Dengue Virus, RyDEN, Repressor of Yield of DENV Protein, Interferon-Regulated Antiviral, UPF0515 Protein C19orf66, IRAV.

In some embodiments, the signature may refer to the set of genes, such as the 64 genes as set forth in Table 1, included in a host response/gene expression signature, or in more specific embodiments, a subset of genes within the host response/gene expression signature that may be used in any of the various tasks, for example, discriminating between presence of infection versus no infection, determining etiology of an infection/pathogen class (bacterial, fungal, protozoan, viral), discriminating sepsis versus a non-infectious illness/SIRS, and determining pathogen class causing sepsis. The subset of genes from the host response signature is not particularly limited, and may be as many or as few a number of genes in the host response signature that are required to perform any one of the various tasks as set forth herein. Exemplary numbers of genes in the signature may be 5, 10, 16, 20, 25, 32, 40, 50, 60 genes, for example from the 64 genes of the host response signature as set forth in Table 1, but it will be appreciated that the number of genes in the signature may be any number of genes between about, for example, 5-64 genes from those as set forth in Table 1. It will be appreciated that signatures that may be used to perform a particular task, for example, discriminating between sepsis and SIRS, using a particular technology or platform X, may differ from signatures that may be used to perform the same task using technology or platform Y. It will also be appreciated that used to perform another particular task, for example, determining the pathogen that can be causing sepsis on platform X, may require different biomarkers than used for discriminating between sepsis and a non-infectious illness/SIRS on platform X.

The terms "classifier" and "predictor," as used herein, may be used interchangeably and generally refer to a rules engine and/or a process that uses the values of the signature (e.g., gene expression levels for a defined set of genes) and a pre-determined coefficient (or weight) for each signature component to generate scores for a given observation or individual patient for the purpose of assignment to a category. The classifier may be linear and/or probabilistic. A classifier can be linear if scores are a function of summed signature values weighted by a set of coefficients. Furthermore, a classifier can be probabilistic if the function of signature values generates a probability, a value between 0 and 1.0 (or 0 and 100%) quantifying the likelihood that a subject or observation belongs to a particular category or will have a particular outcome, respectively. Probit regression and logistic regression are examples of probabilistic linear classifiers that use probit and logistic link functions, respectively, to generate a probability. In some embodiments, determining a probability that an observation belongs to a particular category, for example, the probability a subject has an infection or the probability the subject does not have an infection; the probability a subject has sepsis or the probability the subject has a non-infectious illness/SIRS; or the probability the subject has a bacterial infection, the probability the subject has a viral infection, the probability the subject has a fungal infection (determining etiology of infection), or the probability the subject has a non-infectious illness, includes comparing the probability the observation belongs to a particular category to pre-defined thresholds, cut-off values, and/or ranges or bands of values that indicate the likelihood the observation belongs to a particular category.

A classifier may be developed by a procedure known as "training," which makes use of a set of data containing observations with known category membership (e.g., bacterial, fungal, protozoan, viral, sepsis, infection, and/or non-infectious illness/inflammatory response). Specifically, training seeks to find the optimal coefficient (e.g., weight) for each component of a given signature (e.g., gene expression level components and differential expression levels of components), as well as an optimal signature, such as a set of genes/biomarkers, where the optimal result can be determined by the highest achievable classification accuracy.

The term "classification," as used herein, generally refers to a method of assigning a subject suffering from or at risk for symptoms to one or more categories or outcomes (e.g., a patient is infected with a pathogen or is not infected, another categorization may be that a patient is infected with a virus and/or infected with a bacterium). In some cases, a subject may be classified to more than one category, e.g., in case of bacterial and viral co-infection. The outcome, or category, can be determined by the value of the scores reported by, provided by, generated by, and/or derived from the classifier, or scores reported by, provided by, generated by, and/or derived from multiple classifiers, as may be the case when a subject belongs to more than one category, which may be compared to cutoff values or threshold values, confidence levels, or limits, to derive, generate and/or report a probability for the score or scores reported by, provided by, and/or derived from the classifier or classifiers that the subject suffering from or at risk for symptoms belongs to a particular category or categories. In some embodiments, the probability of belonging to a particular category or categories may be given, e.g., if the classifier reports probabilities. In some embodiments, a high probability or likelihood reported by the classifier may be about 0.7 or greater, may be about 0.75 or greater, about 0.8 or greater, about 0.85 or greater, about 0.9 or greater, about 0.95 or greater, about 0.98 or greater, or about 0.99 or greater. In some embodiments a high percentage likelihood reported by the classifier may be about 70% or greater, about 75% or greater, about 80% or greater, about 85% or greater, about 90% or greater, about 95% or greater, about 98% or greater, or about 99% or greater.

Threshold values, for the purpose of determining if an observation or an individual patient falls in a particular category or can be determined as positive for belonging to a particular category, are not particularly limited, and can be any value, for example, a probability between 0 and 1. In some embodiments, a threshold value for determining if an observation or an individual patient falls in a particular category may be in a (probability) range, for example, about 0.25 or greater, may be about 0.3 or greater, may be about 0.35 or greater, may be about 0.4 or greater, may be about 0.45 or greater, may be about 0.5 or greater, may be about 0.55 or greater, may be about 0.6 or greater, may be about 0.65 or greater, may be about 0.7 or greater, may be about 0.75 or greater, may be about 0.8 or greater, may be about 0.85 or greater, may be about 0.9 or greater, may be about 0.95 or greater, may be about 0.98 or greater, or may be about 0.99 or greater, up to and including 1, and any value between 0 and 1, and/or any value within the specified range.

In some embodiments, threshold values, for the purpose of determining if an observation or an individual patient falls in a particular category or can be determined as positive for belonging to a particular category, may be provided in terms of a percentage from 0 to 100%. In some embodiments, a threshold value for determining if an observation or an individual patient falls in a particular category may be in a (percentage) range, for example, about 25% or greater, may be about 30% or greater, may be about 35% or greater, may be about 40% or greater, may be about 45% or greater, may be about 50% or greater, may be about 55% or greater, may be about 60% or greater, may be about 65% or greater, may be about 70% or greater, may be about 75% or greater, may be about 80% or greater, may be about 85% or greater, may be about 90% or greater, may be about 95% or greater, may be about 98% or greater, or may be about 99% or greater, up to and including 100%, and any value between 0% and 100%, and/or any value within the specified range.

The term "indicative," as used herein, when used with gene expression levels, can generally mean that the gene expression levels are up-regulated or down-regulated, altered, or changed compared to the expression levels in alternative biological states (e.g., bacterial infection, fungal infection, protozoan infection, viral infection, noninfectious illness/inflammation and/or healthy) or control. The term "indicative," as used herein, when used with protein levels, can generally mean that the protein levels are higher or lower, increased or decreased, altered, or changed compared to the standard protein levels or levels in alternative biological states. Measured gene expression levels and/or protein levels, when analyzed with pre-determined weights in the context of a classifier, such as a classifier for a presence of an infection, etiology of an infection and/or a biological state as described herein, may report, provide, and/or generate a score, probability, outcome, and/or result "indicative" of the presence of an infection in, the etiology of an infection in, and/or a biological state of, a subject or patient.

The terms "subject" and "patient," as used herein, may be used interchangeably and generally refer to any animal being examined, studied, or treated. It is not intended that the present disclosure be limited to any particular type of subject. In some embodiments, humans are the preferred subject, while in other embodiments non-human animals are the preferred subject, including, but not limited to, mice, monkeys, ferrets, cattle, sheep, goats, pigs, chicken, turkeys, dogs, cats, horses and reptiles, and for example, a laboratory animal such as a rat, mouse, guinea pig, rabbit, primates, etc.), a farm or commercial animal (e.g., a cow, pig, horse, goat, donkey, sheep, etc.), or a domestic animal (e.g., cat, dog, ferret, horse, etc.).

In certain embodiments, the subject can be suffering from an infection and/or can be displaying signs and/or symptoms consistent with sepsis.

The terms "platform" or "technology," as used herein, generally refer to an apparatus (e.g., instrument and associated parts, computer, computer-readable media comprising one or more databases as taught herein, reagents, etc.) that may be used to measure a signature, e.g., gene expression levels, in accordance with the inventive concept. Platforms include the subcategories of 'open' or 'closed' platforms. A closed platform may include a sample to answer system of modules for sample preparation and purification, amplification, and detection, often housed in a closed test cartridge.

Such platforms can be more rapid and lower throughput than their open platform counterparts, and require less technical expertise to operate. Examples of platforms include, but are not limited to, an array hybridization platform, a thermal cycling or isothermal amplification and detection platform (e.g., multiplexed and/or real-time PCR platform), a nucleic acid sequencing platform, a next generation (second generation) sequencing platform, a single-molecule nanopore sequencing (third generation) platform, a hybridization and multi-signal coded (e.g., fluorescence) detector platform, etc., a nucleic acid mass spectrometry platform, a magnetic resonance platform, a diagnostic platform, and any combination or combinations thereof.

In some embodiments, the platform can be configured to measure gene expression levels semi-quantitatively, that is, rather than measuring discrete or absolute expression, the expression levels are measured as an estimate and/or relative to each other or a specified marker or markers (e.g., expression of another, "standard" or "reference," gene).

In some embodiments, semi-quantitative measuring may include "real-time amplification" by performing, for example, PCR cycles or isothermal amplification, which may include intermediary reverse transcription of RNA to cDNA and amplification of cDNA, until a signal indicating the specified mRNA can be detected, and using the number of amplification cycles needed until detection to provide the estimated or relative expression levels of the genes within the signature.

A real-time PCR platform may include, for example, a TaqMan® Low Density Array (TLDA), in which samples undergo multiplexed reverse transcription, followed by real-time PCR on an array card with a collection of wells in which real-time PCR can be performed. See Zaas et al. 2013, Sci. Transl. Med. 5(203):203ra126. doi: 10.1126/scitranslmed.3006280. PMID: 24048524. A real-time PCR platform also includes, for example, a Biocartis Idylla™ sample-to-result technology, in which cells are lysed, DNA/RNA extracted, real-time PCR can be performed, and results detected. Other platform technologies using real-time PCR, or qPCR, include the Franklin™ by Biomeme and the Qvella FAST™ device. A thermal cycler platform may include, for example, the FilmArray® multiplex PCR system, which extract and purifies nucleic acids from an unprocessed sample and performs nested multiplex PCR; and the RainDrop Digital PCR System, which is a droplet-based PCR platform using micro fluidic chips.

In some cases, the amplification procedure may be an isothermal amplification procedure, such as Loop-Mediated Isothermal Amplification (LAMP), Multiple Displacement Amplification (MDA), Strand Displacement Amplification (SDA), Helicase-Dependent Amplification (HDA), Recombinase Polymerase Amplification (RPA), Nucleic Acid Sequences Based Amplification (NASBA), Rolling Circle Amplification (RCA). An isothermal amplification technology includes, for example, Abbott ID NOW™ isothermal amplification technology.

A magnetic resonance platform may include, for example, T2 Biosystems® T2 Magnetic Resonance (T2MR®) technology, in which molecular targets may be identified in biological samples without the need for purification.

The terms "array," "microarray" and "micro array," as used herein, are interchangeable and may generally refer to an arrangement of a collection of nucleotide sequences presented on a substrate. Any type of array can be utilized in the methods provided herein. For example, arrays can be on a solid substrate (a solid phase array), such as a glass slide, or on a semi-solid substrate, such as nitrocellulose membrane. Arrays can also be presented on beads, e.g., a bead array. These beads can be microscopic and may be made of, e.g., polystyrene. The array can also be presented on nanoparticles, which may be made of, e.g., particularly gold, but also silver, palladium, or platinum. See, e.g., Nano sphere Verigene® System, which uses gold nanoparticle probe technology. Magnetic nanoparticles may also be used. Other examples include nuclear magnetic resonance micro-coils. The nucleotide sequences can be DNA, RNA, or any permutations thereof (e.g., nucleotide analogues, such as locked nucleic acids (LNAs), and the like). In some embodiments, the nucleotide sequences span exon/intron boundaries to detect gene expression of spliced or mature RNA species rather than genomic DNA. The nucleotide sequences can also be partial sequences from a gene, primers, whole gene sequences, non-coding sequences, coding sequences, published sequences, known sequences, or novel sequences. The arrays may additionally comprise other compounds, such as antibodies, peptides, proteins, tissues, cells, chemicals, carbohydrates, and the like that specifically bind proteins or metabolites.

An array platform may include, for example, the TaqMan® Low Density Array (TLDA) mentioned above, and an Affymetrix® microarray platform.

A hybridization and multi-signal coded detector platform includes, for example, NanoString nCounter® technology, in which hybridization of a color-coded barcode attached to a target-specific probe (e.g., corresponding to a gene expression transcript of interest) can be detected; and Luminex® xMAP® technology, in which microsphere beads are color coded and coated with a target-specific (e.g., gene expression transcript) probe for detection; and Illumina® BeadArray, in which microbeads are assembled onto fiber optic bundles or planar silica slides and coated with a target-specific (e.g., gene expression transcript) probe for detection.

A nucleic acid sequencing platform may include, for example, the Illumina bridge amplification technology, generating amplified DNA clusters and reversible dye terminators for sequence determination. Sequencing in the context of gene expression provides absolute read counts and relative levels for RNA transcripts, and may provide information on transcript sequence and spicing variants. Other sequencing technologies include, for example, nanopore sequencing technologies in which single RNA or DNA molecules can be directly sequenced with or without the need for amplification or labeling, and detect unique electrical signals as polynucleotides pass through nanopores in the surface of a semiconductor or other solid state or biological substrate. Nanopore sequencing technologies include, for example, direct sequencing using the Oxford Nanopore Technologies MinION™ and GridION™, and nanopore sequencing of modified or surrogate molecules, such as the Roche SBX™ (Sequencing By eXpansion) technology.

The term "computer readable medium," as used herein, generally refers to any device or system for storing and providing information (e.g., data and instructions) to a computer processor. Examples of computer readable media include, but are not limited to, DVDs, CDs hard disk drives, magnetic tape and servers for streaming media over networks, and applications, such as those found on smart phones and tablets. In some aspects, data structures and methods may be stored on a computer readable medium. Processing and data may also be performed on numerous device types, including but not limited to, desktop and laptop computers, tablets, smart phones, and the like.

The term "biological sample," as used herein, generally includes any sample that may be taken from a subject/biological source that contains genetic material that can be used in the methods provided herein. For example, a biological sample may comprise a blood sample, such as a peripheral blood sample. The term "peripheral blood sample," as used herein, generally refers to a sample of blood circulating in the circulatory system or body taken from the system of body. Other samples may comprise those taken from the upper respiratory tract, including but not limited to, sputum, nasopharyngeal swab and nasopharyngeal wash, or synovial fluid, or cerebrospinal fluid. A biological sample may also include those samples taken from the lower respiratory tract, including but not limited to, sputum, bronchoalveolar lavage and endotracheal aspirate. A biological sample may also include any combinations thereof. A "biological source" includes, for example, human or non-human subjects ("in vivo"), cultured cells ("in vitro"), and primary human tissues ("ex vivo") from which a sample/biological sample may be obtained/derived from. Measurements/determinations/analysis of, for example, expression levels of genes, in a biological source or in biological sources include, and may be provided by, in some embodiments, measurements/determinations/analysis of expression levels of genes in a sample/biological sample derived from the biological source.

The terms "obtaining," "gathering," and/or "collecting," as used herein, when referring to expression levels of genes/gene expression levels may generally include experimentally measuring expression levels of genes/gene expression levels in, for example, a sample/biological sample derived from, for example, a biological source, as well as drawing measured/determined gene expression levels from, for example, public and/or commercially available databases of gene expression data. The terms "obtaining," "gathering," and/or "collecting," as used herein, when referring to a sample, such as a biological sample, may generally include experimentally obtained, gathered, and/or collected samples from a source, such as a biological source, as well samples drawn from, for example, publicly available and/or commercial repositories.

The terms "treat", "treatment" and "treating," as used herein, generally refer to the reduction or amelioration of the severity, duration and/or progression of a disease or disorder, such as an infection resulting from bacterial, viral, or fungal sources, or one or more symptoms thereof resulting from the administration of one or more therapies. Such terms may refer to a reduction in the replication of bacteria, a fungus or a virus, or a reduction in the spread of bacteria, a fungus or a virus to other organs or tissues in a subject or to other subjects. Treatment may also include therapies for non-infectious inflammatory disease or disorders.

The term "appropriate treatment regimen," as used herein, generally refers to the standard of care needed to treat a specific disease or disorder. Often such regimens require the act of administering to a subject a therapeutic agent(s) capable of producing a curative effect in a disease state. For example, an appropriate treatment regimen may include administration of any therapeutic agent for treatment of bacterial, fungal, and/or viral infections, such as antibiotics, antifungals and/or antivirals in an appropriate amount. The inventive concept further contemplates the use of methods according to the inventive concept to determine treatments of bacterial, fungal, and/or viral infections with therapeutics, such as antibiotics, antifungals, and/or antivirals that are not yet available.

Methods for Generating and/or Discovering a Host Response Signature

The present inventive concept includes methods for generating a host response signature. In some embodiments of the inventive concept, the method may include (i) identifying a host response signature using open platform data, (ii) generating a classifier(s) during the process of translating said signature, or a subset(s) thereof to a closed diagnostic platform, and (iii) selecting coefficients for the classifier(s) using data generated on the closed diagnostic platform. In some embodiments the signature may include, for example, a pre-defined set of 64 genes, and this signature, or subsets of this pre-defined set of genes, for example, but not limited to, a 32 gene or a 16 gene subset, or even subsets of the 32 gene or 16 gene subsets, can be used in diagnostic tests when translated to diagnostic testing platforms. This translation process includes not only the ability to physically measure expression of each gene and normalizing the expression levels, but also the development of a mathematical equation, e.g., a classifier, that can be in a form of a logistic regression equation. This classifier will include normalized expression values (these are the "features" of the regression equation), each of which can be accompanied by a weighting value. The weighted expression values can be summed in the classifier and the output of the regression equation can be a probability or score. The score can be compared to a cutoff value or threshold or a range or a band of scores in order to make a decision regarding, e.g., a classification, a patient's condition. It can be noted that the same genes or overlapping gene sets may be used in multiple classifiers, e.g., for determination of infection, sepsis versus non-infectious illness/SIRS, and etiology of infection, for example whether an infection is bacterial, viral, or fungal in nature. The discriminatory power of each classifier arises not only from the features (genes) of the classifiers but also from the predetermined gene weights and the predetermined cutoff or threshold values that are discovered as the classifier is "trained."

Methods of generating a host response signature and classifiers include methods as set forth in International Application No. PCT/US2016/040437, the disclosure of which is incorporated by reference in its entirety. A classifier as taught herein may be obtained by a procedure known as "training," which makes use of a set of data containing observations with known category membership (e.g., bacterial infection, viral infection, fungal infection, and/or non-infectious illness). Specifically, training seeks to find the optimal coefficient (e.g., weight) for each component of a given signature (e.g., gene expression level components), as well as an optimal signature, where the optimal result can be determined by the highest achievable classification accuracy.

Accordingly, classifiers may be obtained, where each classifier can be composed of a weighted sum of all or a subset of normalized gene expression levels. This weighted sum defines a probability that allows for a decision (classification), particularly when compared to a threshold value or another result-reporting scheme such as the use of bands. The exact combination of genes, their weights and the threshold(s) for each classifier obtained by the training are particular to a specific platform. The classifier (or more precisely its components, namely weights and threshold(s)) go to a database. Weights with a nonzero value determine the subset of genes used in the classifier. The process may be repeated to obtain all classifiers (infection classifier, sepsis classifier, bacterial infection classifier, viral infection classifier, fungal infection classifier, non-infectious illness classifier and SIRS classifier) within a specified platform matching the gene expression values.

The weights and threshold or cutoff values can be determined by a process of training during translation of the host response signature, or a subset of genes in the signature, to a diagnostic testing platform and will be unique to each new test. Training can be a computationally intensive, iterative process that seeks to optimize classification accuracy by adjusting the weighting values. Training requires the use of a population of gene expression data from samples (in vivo, in vitro or ex vivo samples) with known status or label (e.g., infection, bacterial infection, viral infection, fungal infection, sepsis, no infection, SIRS, healthy). Once these weights and threshold values are recorded in a database on a testing instrument (including, but not limited to, computers, for example, personal computers (PCs), such as desktop or laptop PCs, mobile/handheld devices, such as tablets and/or mobile phones, or located on the cloud, etc.), then an individual patient can be tested using the stored weights and thresholds that were determined using the population of labeled data.

As an example of the workflow, a patient can present with symptoms that can be due to an infection, sepsis, or a non-infectious inflammatory condition. A sample (e.g., a blood sample or any sample that can yield RNA) can be withdrawn from the patient. The RNA in the sample may be purified, or not, before being applied to the testing platform, it may be purified on the testing platform, or may not be purified. The testing platform will measure the expression levels of the genes and then will computationally normalize these expression levels against the expression of one or more normalization (e.g., "housekeeping") genes measured in the same patient sample. These normalized expression values can be entered into the classifier with the weights that are retrieved from the database. A computer retrieves the weights, conducts all the expression normalization, and calculates a score. The computer may also graph or otherwise present the score versus a threshold or cutoff value, or interval range, or band of values, that was previously determined during training and translation to the platform (and determined from the population of samples of known status). Based on the score versus the cutoff value(s), the computer may also offer a presumptive diagnosis. The clinician, or the person running the test who may be the patient themselves, will use this score or presumptive diagnosis in the context of the cutoff value, or band, and often in conjunction with other clinical or epidemiological information, to make a diagnosis. It can also be noted that threshold or cut-off values can be adjusted to change test performance, e.g., test sensitivity and specificity. For example, the threshold for assignment of the condition of sepsis may be intentionally lowered to increase the sensitivity of the test for sepsis.

The test can have a sensitivity of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%. The test can have a specificity of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%. The test can have an accuracy of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%.

The testing platform can measure the expression levels of the genes and may normalize these expression levels against the expression of one or more normalization (e.g., "housekeeping") genes. These normalized expression values may be entered into the classifier with the weights that are retrieved from the database. A computer may be used to retrieve the weights, conduct all the expression normalization, and calculate a score. The computer may also graph or otherwise present the score versus a threshold or cutoff value, or confidence interval that was previously determined during translation to the platform (and determined from the population of samples of known status). Based on the probability versus the cutoff value(s), the computer may also offer a presumptive diagnosis. The clinician, or the person running the test that may be the patient themselves, will use this score or presumptive diagnosis in the context of the cutoff value, and likely in conjunction with other clinical or epidemiological information, to make a final diagnosis.

The overall process from discovery of the host response signature to translation includes: 1) host response signature discovery; 2) host response signature performance evaluation; and 3) translation of the host response signature to a platform, wherein translation may include developing methods to measure expression of genes, developing methods to normalize gene expression, determining weights for each gene in the logistic regression classifier and determining cutoff, threshold or, which can be done with a population of samples with "known" labels or class status, locking these weights and cutoff values in a computer database, enacting the regression equation on a computer that can pull the weights and compare the output probability to the cutoff, threshold(s), and express the result in a useful format.

Accordingly, discovery of a host response signature of genes according to embodiments of the inventive concept, all, or a subset thereof which can be used to: determine the presence or absence of an infection, wherein no infection may include healthy or non-infectious illness; and/or determine whether an infectious agent is bacterial, fungal, or viral in nature.

The host response signature, or a subset of genes thereof, may be used more particularly, in some embodiments, for determining if a subject has sepsis, or a non-infectious illness, including systemic inflammatory response syndrome (SIRS). The signature may also be used to determine the class of pathogen causing sepsis.

It will also be appreciated that normalization genes may be useful on a technology platform to normalize gene expression levels. These genes can be selected for having expression levels that do not change in response to any of the conditions of interest, e.g., presence or absence of infection, sepsis, as described herein. Examples of normalization/reference genes include, but are not limited to, for example, HPRT1, CRCP, WDR33, HIGD1A, DMTF1, UBE3A, G3BP2, PUM1, RBBP4, HNRNPM, and ZNF250, or any combination thereof. In some embodiments, the normalization/reference gene may be HPRT1. In some embodiments, the normalization/reference gene may be PUM1. In some embodiments, the normalization/reference genes may be HPRT1 and PUM1.

Evaluation of Model Performance

The ability of a classification model composed of the host response signature (64 genes), and subsets of the signature (for example, but not limited to, 32 and 16 genes, or even subsets thereof), to undertake the various classification tasks can be evaluated in a number of ways. The performance can be expressed as an AUROC (area under the receiver operating characteristics) or AUC, which is a global statistic that tells us how well the model distinguishes between the various classes. An AUC of 0.5 means that the model is not able to discriminate between the possible classes any better than chance. The visualization of this is the ROC (receiver operating characteristics) curve, which plots the True Positive Rate (TPR) (y-axis) versus the False Positive Rate (FPR) (x-axis). The TPR indicates the "sensitivity" of the model. The "specificity" of the model is (1-FPR). One may balance sensitivity versus specificity by shifting the threshold between true negatives and true positives. Using the Receiver Operating Characteristic curves as a guide, if the threshold or cutoff is lowered, sensitivity is favored over specificity. Therefore, the threshold may be "tuned" to accommodate the performance requirements of the eventual diagnostic test.

The other performance measurement used for evaluation of the classification model can be the confusion matrix. In the cases presented herein, multiclass confusion matrices can be constructed to show the performance of the model across all classes. These matrices plot the predicted class (vertical) versus the actual class (horizontal). The 'true' class of each sample can be the label that is attached to it in the discovery datasets.

Methods for Measuring Gene Expression

There are a number methods for quantifying gene expression. This may be accomplished by direct measurement of RNA, such as mRNA, by measurement of derived materials (e.g., cDNA), and by measurement of RNA products (e.g., encoded proteins or peptides). Any method of extracting and measuring gene expression may be used for the purpose described.

In some embodiments, measurement of mRNA may be quantitative or semi-quantitative. In some embodiments, detection and quantification of mRNA may involve a reverse transcription and/or amplification step, e.g., RT-PCR such as quantitative RT-PCR. In some embodiments, detection and quantification may be based upon the unamplified mRNA molecules present in or purified from the biological sample. Direct detection and measurement of RNA molecules can involves hybridization to complementary primers and/or labeled probes. Such methods include northern blotting and surface-enhanced Raman spectroscopy (SERS), which involves shooting a laser at a sample exposed to surfaces of plasmonic-active metal structures with gene-specific probes and measuring changes in light frequency as it scatters. Other methodologies for measuring mRNA include northern blotting, ribonuclease protection assays, surface-enhanced Raman spectroscopy (SERS), and serial analysis of gene expression (SAGE). Other methods include quantitative polymerase change reaction (qPCR) (e.g. real-time, reverse transcription quantitative PCR), digital PCR (dPCR), loop mediated isothermal amplification (LAMP), and quantitative nucleic acid sequence-based amplification (QT-NASBA), and next generation sequencing, microarrays, and in situ hybridization.

Detection of RNA derivatives, such as cDNA, can involve hybridization to complementary primers and/or labeled probes. This may include high-density oligonucleotide probe arrays (e.g., solid state microarrays and bead arrays) or related probe-hybridization methods, and polymerase chain reaction (PCR)-based amplification and detection, including real-time, digital, and end-point PCR methods for relative and absolute quantitation of specific RNA molecules.

Additionally, sequencing-based methods can be used to detect and quantify RNA or RNA-derived material levels. When applied to RNA, sequencing methods are referred to as RNAseq, and provide both qualitative (sequence, or presence/absence of an RNA, or its cognate cDNA, in a sample) and quantitative (copy number) information on RNA molecules from a sample. See, e.g., Wang et al. 2009 Nat. Rev. Genet. 10(1), 57-63. Another sequence-based method, serial analysis of gene expression (SAGE), uses cDNA "tags" as a proxy to measure expression levels of RNA molecules.

Moreover, use of proprietary platforms for RNA detection and quantification may also be used to complete the methods of the present disclosure. Examples of these include Pixel™ System, incorporating Molecular Indexing™, developed by CELLULAR RESEARCH, INC.®, NanoString® Technologies nCounter gene expression system; mRNA-Seq, Tag-Profiling, BeadArray™ technology and VeraCode from Illumina, the ICEPlex System from PrimeraDx, the QuantiGene 2.0 Multiplex Assay from Affymetrix and Qvella FAST-ID™ technology. In some embodiments, detection, and quantification of gene expression levels in the methods according to the inventive concept are accomplished by detecting and quantitating mRNA levels using Qvella FAST-ID™ technology.

Gene expression may be detected using a number of chemistries, including DNA binding dyes, hybridization probes, molecular beacons, hydrolysis probes, Light upon extension (LUX) primers, among others. These detection methods can rely upon detection of a fluorescence signal.

In some embodiments, the measuring includes the detection and quantification (e.g., semi-quantification) of mRNA in the sample. In some embodiments, the gene expression levels can be normalized by adjustment relative to the expression of one or more normalization or housekeeping genes ("normalized"). Normalizing can be done to remove technical variability inherent to a platform and process.

Signature Generation and Discovery Data

Data for discovery of gene targets that can be used to determine whether a host (e.g. a human patient) has an infection or no infection, has sepsis or an infection and therefore at risk of developing sepsis, or whether a host can be infected by a particular class of pathogen, was drawn from publicly available data in two databases, Array Express (www.ebi.ac.uk/arrayexpress/, Athar et al. 2019. Nucleic Acids Res. doi: 10.1093/nar/gky964. Pubmed ID 30357387) and Gene Expression Omnibus (GEO; www.ncbi.nlm.nih-.gov/geo/. Barrett et al. 2013. Nucleic Acids Res. 41(Database issue), D991-995).

Processed expression data from the studies downloaded from GEO and ArrayExpress was extracted and normalized. A number of studies were excluded during data extraction and normalization due to an absence of processed data, corrupted processed data, absence of sample expression data (differential studies), missing platform information paired with generic probe IDs, or the expression data was not from a human source. All genes in the subsequent discovery analysis were mapped to the 41,424 HUGO approved genes.

The following studies and samples were used as input data to the Signature Discovery Model to discover a gene target signature to differentiate between the binary phenotypes, infection and non-infection (which included non-infectious illness, inclusive of systemic inflammatory response syndrome (SIRS) and healthy phenotypes). The signature can also differentiate between viral, fungal and bacterial causes of infection. The multiclass phenotypes used in this discovery process are infection, healthy, non-infectious illness, SIRS, bacterial infection, fungal infection, and viral infection. The phenotype labels were either included in the dataset or were identified from the literature cited in the annotation for the dataset. The 'infection' class included a broad array of conditions where the infectious pathogen was not specifically identified, including infectious syndromes such as appendicitis, pneumonia, diverticulitis, endocarditis, peritonitis, sepsis, septic shock, ventilator-associated pneumonia. In addition, the 'infection' class included all samples that were labeled with the phenotype indicating a bacterial, a viral, and/or a fungal infection. Furthermore, non-infectious illness, which encompasses a large number of non-infectious conditions, including systemic inflammatory response syndrome (SIRS), are exemplified as shown in Table 2, along with various bacterial, viral, and fungal pathogens making up the classes of infections that are part of these studies.

TABLE 2

Classes of infections included in these studies.

| Unspecified Infections | Bacterial | Viral | Fungal | Non-infectious |
|---|---|---|---|---|
| Appendicitis | Acinetobacter Iwoffii | Hepatitis B virus, acute | Aspergillus fumigatus | Acute lymphoblastic leukemia |
| Pneumonia | Acinetobactor baumannii | Hepatitis C virus, acute | Candida albicans | Acute myeloid leukemia |
| Diverticulitis | Aeromonas | HIV, acute | Candida parapsilosis | Allergic rhinitis |
| Endocarditis | Aeromonas hydrophila | Adenovirus | Cryptococcus neoformans | Amyotrophic Lateral Sclerosis |
| Peritonitis | Bacillus | BK virus | Trichosporon asahii | Acute Respiratory Distress Syndrome |
| Sepsis | Bacterial infection, NOS | Bocavirus | | Asthma |
| Septic shock | Bordetella pertussis | Chikungunya | | Bowel obstruction |
| Ventilator-Associated Pneumonia | *Brucella abortus* | CMV | | Breast cancer |
| | Burkholderia pseudomallei | Coronavirus | | Chronic Obstructive Pulmonary Disease |
| | Campylobacter jejuni | Dengue | | Crohn's disease |
| | Chlamydia pneumoniae | Ebola | | Diabetes Mellitus |
| | Corynebacterium | Epstein Barr Virus | | Drug reaction |
| | Coxiella burnetii | Enterovirus | | Gastrointestinal hemorrhage |
| | Eikenella | Herpes Simplex Virus | | Hemochromatosis |
| | Enterobacter | Influenza | | Hernia |
| | Enterobacter cloacae | Japanese Encephalitis Virus | | Henoch-Schonlein purpura |
| | Enterococcus | Kaposi Sarcoma Herpes Virus | | Hypersensitivity pneumonitis |
| | Enterococcus faecalis | Lassa | | Juvenile Idiopathic Arthritis |
| | Enterococcus faecium | Measles | | Kawasaki disease |
| | *Escherichia coli* | Metapneumovirus | | Lung cancer |
| | Francisella tularensis | Monkeypox | | Microscopic Polyangiitis |
| | Gram negative, NOS | Orf Virus | | Multiple sclerosis |
| | Gram positive, NOS | Parvovirus B26 | | Multiple myeloma |
| | Group B Streptococcus | Rhinovirus | | Myeloproliferative neoplasm |
| | Haemophilus influenzae | Rift Valley Fever | | Pancreatitis |
| | Klebsiella oxytoca | Rotavirus | | Post-operative status |
| | Klebsiella pneumoniae | Respiratory Syncytial Virus | | Rheumatoid arthritis |
| | Legionella pneumophila | SARS coronavirus | | Sarcoidosis |
| | Leptospira interrogans | Sendai | | Systemic Inflammatory Response Syndrome |
| | Listeria monocytogenes | Vaccinia | | Still's disease |
| | Micrococcus | Varicella zoster virus | | Systemic lupus erythematosus |
| | Neisseria meningitidis | Viral infection, NOS | | Trauma |
| | Orientia tsutsugamushi | Western Equine Encephalitis virus | | Ulcerative colitis |
| | Pseudomonas aeruginosa | West Nile Virus | | Ureterolithiasis |
| | Rickettsia | Yellow fever | | Vasculitis |
| | Salmonella | Zika | | Wegener's Granulomatosis |
| | Salmonella typhi | | | |
| | Salmonella typhimurium | | | |
| | Serious Bacterial Infection | | | |
| | Serratia marcescens | | | |
| | Shigella flexneri | | | |
| | Sphingobacterium | | | |
| | Sphingomanas | | | |
| | *Staphylococcus aureus* | | | |
| | Staphylococcus coagulase negative | | | |
| | Staphylococcus epidermidis | | | |
| | Staphylococcus hominis | | | |
| | Stenotrophomonas maltophilia | | | |
| | Streptoccus suis | | | |
| | Streptococcus agalactiae | | | |
| | Streptococcus pneumoniae | | | |
| | *Streptococcus pyogenes* | | | |
| | Tropheryma whipplei | | | |
| | Viridans Group Streptococcus | | | |

Gene expression data were derived from three biological sources, including biological samples such as blood or tissue samples from human subjects with the specified condition (labeled "in vivo"), cultured cells exposed to the specified pathogen (labeled "in vitro"), and primary human tissues that were challenged in vitro with the specified pathogen (labeled "ex vivo").

Database

GEO—194 Studies, 7476 Samples
ArrayExpress—12 Studies, 520 Samples

Binary Phenotypes
Infection (4965 samples)
Non-infection includes healthy and non-infectious conditions (3031 samples)

Multi-class Phenotypes
Healthy (2204 samples)
Non-infectious conditions (subsequently used interchangeably with SIRS, though for some samples SIRS criteria may not have been met) (827 samples)
Viral (2479 samples)
Bacterial (865 samples)
Fungal (73 samples)
Infection (no pathogen class label was included in the dataset) (1548 samples)
Information on the biological source of the sample was extracted from the annotations for each dataset.

Biological Source
in vivo (6812 samples)—In vivo refers to samples collected from human subjects with the specified condition.
ex vivo (753 samples)—Ex vivo refers to biological samples (e.g. peripheral blood mononuclear cells) drawn from human subjects and challenged with various pathogens or treatments under experimental conditions.
in vitro (431 samples)—In vitro refers to cultured, immortalized cell lines challenged with various pathogens or treatments under experimental conditions.

Methods of Generating the Host Response Signature

The method of generating a host response signature, such as a pre-defined set of genes, and host response classifiers to make diagnostic test decisions according to the inventive concept, includes using gene expression data from publicly available datasets obtained from GEO and ArrayExpress. Datasets from these sources were included if the infection occurred in human subjects (in vivo), in cells derived from human subjects (ex vivo), and in human cell cultures (in vitro). The condition of 'infection' included data from samples labeled as 'infection', where the cause of infection may or may not have been specifically described (e.g., been labeled as an unspecified infection), or labeled as 'sepsis', as infection due to a bacterium ('bacterial infection'), as infection due to a fungus ('fungal infection'), or as infection due to a virus ('viral infection'). The comparator data for development of the host response signature are similarly from in vivo, ex vivo or in vitro sources. This comparator data can be broadly labeled as 'non-infection' and includes data from samples labeled as 'healthy', 'non-infectious illness' (see Table 2), or 'SIRS' (systemic inflammatory response syndrome). In addition to the gene expression data and the source of the sample, each gene expression datapoint was included if it had an unequivocal phenotype label, e.g., infection, healthy, sepsis, SIRS, one of a number of non-infectious illnesses, or infection due to fungi, virus, or bacteria. See Table 2 for a list of etiologies for unspecified infection, non-infectious illness, and bacterial, viral, and fungal infections.

The broad array of sample types and conditions included during signature discovery is innovative and a strength of this approach. One advantage of this approach can be that it enables the generalizability and robustness of the signatures and resultant host response classifiers for use in broad populations and testing scenarios. Inclusion of a large number of data sets from different sources and diverse sample types (e.g., in vivo, ex vivo, and in vitro data), also ensures inclusion of data that recalls mild to serious disease and biological responses from the earliest time points from early infection to late-stage infection. Another advantage of this approach can be that it powers the generation of a host response signature and classifier(s) that can distinguish between infection or non-infectious illness that may be due to dysregulated inflammatory response without infection, and sepsis, which can be a condition characterized by organ dysfunction due to a dysregulated host inflammatory response to an infection. A third advantage of the approach for generation of the host response signature can be that it permits not only determination of the presence of infection, or sepsis, but also the identification of the class of pathogen causing the condition (the etiology of infection), where determination of etiology can be conditioned on the presence or absence of infection.

The discovery model accounts for systematic differences between studies that generated each data set [using the Reference Mean, as illustrated in Part 1 of FIG. 1] while also allowing the estimation of the importance of individual covariates (genes) during translation to a diagnostic testing platform. The model projects the gene expression data to a lower dimensional space (50 dimensions), and then branches to two decision layers (binary and multi class) [see Part 2 of FIG. 1]. The multi class predictions can be further conditioned on the binary class predictions as shown in Part 3 of FIG. 1. Binary class refers to "infection" and "non-infection". Multi class refers to bacterial, fungal viral, SIRS (e.g., non-infectious illness), and healthy.

Given a set of M studies, each composed of $N_m$ pairs $$\{N_{nm}, y_{nm}\}_{n=1}^{M_m},$$

for m=1, . . . , M, where $X_{nm} \in \mathbb{R}^d$ is a vector of d normalized gene expression values for subject n in study m, and $y_{nm} \in$ {Bacterial, Viral, Fungal, Infection, SIRS, Healthy} is the phenotype assignment for subject n in study m.

The objective is to build a model to estimate $p(y_{nm})=f(X_{nm}; \theta)$, such that, i) the model accounts for systematic differences between gene expression profiles from different studies, e.g., the model is robust to study effects [using the Reference Mean, as illustrated in Part 1 of FIG. 1];
ii) the model can accurately estimate the phenotype from gene expression data; and
iii) the model is sparse, e.g., predictions are obtained using a relatively small number of transcripts (genes); e.g., the gene signature.

Study effects, also referred in more general contexts as batch effects, originate from different sources such as study-wise differences in population, sample collection, sample processing, assay platform and processing procedures. Note that for this discovery task, there is no interest in characterizing these differences or even correcting for them, but rather producing a model that is robust to study effects.

Model sparsity can be a desirable property when the discovered host response signature will be translated to different testing platforms, some of which may not accommodate a large number of gene targets.

Provided that the phenotypes of interest can be structured into a 2-layer hierarchy, instead of attempting to predict all six phenotypes at once, the $p(y_{nm}=\text{Infection})$ for the Infection vs. Non-infection distinction was estimated (See 'Binary True Label' in Part 2 of FIG. 1). Then, the more specific conditionals, $p(y_{nm}=\text{Infection})\in\{\text{Bacterial, Viral, Fungal}\}$, and $p(y_{nm}=\text{Non-infection})\in\{\text{SIRS, Healthy}\}$, where $p(y_{nm}=\text{Non-infection})=1-p(y_{nm}=\text{Infection})$ were estimated (See 'Multi-class True Label' in Part 3 of FIG. 1). Below the subject and study subscripts, n and m, in gene profiles X and labels y are ignored for notational simplicity.

With the considerations above, the proposed model illustrated in FIG. 1 is specified as a four-module classification model composed of the following components:

i) an encoder mapping gene expression profiles X into a latent representation $Z=g(X;\theta_a)$;

ii) a binary classifier mapping the latent representation into the likelihood of infection, $p(y=\text{Infection})=g(Z;\theta_b)$;

iii) a multiclass classifier mapping the latent representation into the likelihood of specific infections, $p(y=\text{Non-infection})=g(Z;\theta_c)$; and iv) a binary classifier mapping the latent representation into the likelihood of SIRS (non-infection) vs. healthy, $p(y=\text{Non-infection})=g(Z;\theta_d)$.

The complete model concisely denoted as $p(X)=f(X;\theta)$, with parameters $\theta=\{\theta_a,\theta_b,\theta_c,\theta_d\}$ is specified with Z as a 50-dimensional vector, and $g(\bullet;\bullet)$ as fully connected layers with appropriate activation functions, namely, the identity for the latent representation, sigmoid for the binary classifier and softmax for the multiclass classifier.

The loss function guiding the training includes four components that are jointly optimized:

$$\text{L1Loss}+\text{MSE}(\text{mean}(Z),\text{Ref\_Mean})+\text{Binary CrossEntropyLoss}(p(\text{Infection}))+\text{MultiClassCrossEntropyLoss}(p(\text{Pathogen})).$$

The L1 Loss sparsifies the projected gene data to exclude genes that are not important in predicting the outcomes. The MSE domain adaptation loss encourages latent representations from different studies to be uninformative of study and thus reduces the influence on non-biological variance. The two Cross Entropy Classification Losses guide the model to make correct predictions concerning the presence or absence of an infection and the biological source of the infection. In practice, the parameters of the model are optimized using the loss function and stochastic gradient descent.

Figure 2:
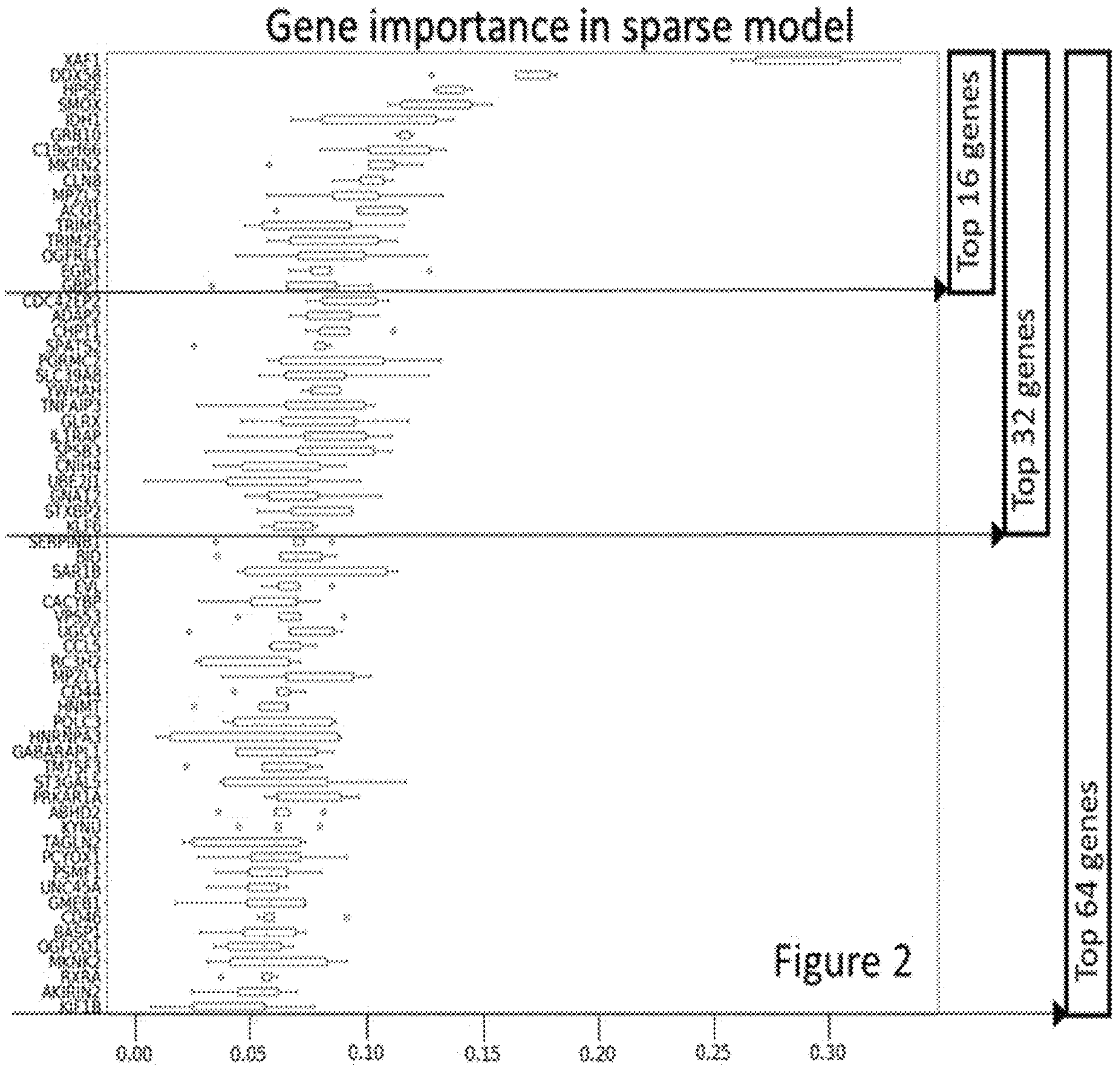
FIG. 2 illustrates the 64 top performing genes in the sparse model arising from the discovery process, where importance is indicated by the weights associated with each individual gene in the discovery model (x-axis). The genes are listed in the figure according to the weight determined during training, sorted from largest (most highly weighted) to smallest (least highly weighted). The weight for each gene is assumed to indicate the importance of the particular gene in correctly predicting the presence or absence of infection as well as the biological source of infection.

64 genes, the host response signature, whose expression are most informative for the classification tasks were selected using this discovery process and are shown in Table 1 and FIG. 2.

Methods of Generating Classifiers

The present inventive concept provides methods for determining whether a patient has an infection, which may be, in some embodiments, indicative of a patient having sepsis, for determining whether the infection or sepsis is due to a bacterial, a viral, or a fungal pathogen, or for determining if the patient has no infection/a non-infectious illness or SIRS. Each of these determinations can be made using a classifier that is in the form of a logistic regression and is the weighted sum of all or a subset of normalized expression levels of the gene targets of the host response signature. This weighted sum can be a probability that allows for a decision (classification) when compared to a threshold or cutoff value or a confidence interval. The exact combination of genes to achieve a specific classification task (e.g., each biomarker), the gene weights and the threshold for each classification can be obtained during classifier training and are specific to each testing platform. The classifier (more particularly, its components, e.g., weights and threshold or cutoff value or range or band of values are stored in a database. Those genes from the host response signature that have non-zero weights are useful for the classification task. This process for determining the subset of host response genes that comprise the biomarker, and the weighting values for each of the genes, and the cutoff, threshold, range, or band of values are determined for each classifier (infection, sepsis, SIRS (non-infectious illness), and bacterial, fungal, viral infection) as implemented on each technology platform.

The normalized expression values for each gene in a host response signature (the entire host response signature from Table 1 and FIG. 2 or a subset thereof) are the independent variables or features used in the logistic regression equation that constitutes the classifier.

The classifier equation may take the general form:

$$P(\text{having condition}) = \Phi(\beta_1 X_1 + \beta_2 X_2 + \ldots + \beta_d X_d)$$

wherein the condition is, e.g., infection. $\Phi(.)$ is the probit (or logistic, etc.) link function; $\{\beta1,\beta2, \ldots, \beta d\}$ are the coefficients obtained through training of the classifier when the host response biomarker is translated to the platform (the coefficients are the previously described weights {w1,w2, . . . ,wd}); {X1,X2, . . . ,Xd} are the normalized gene expression levels of the signature/biomarker; and d is the size of the signature/biomarker (e.g., number of genes).

It can be noted that the threshold or cutoff value may be adjusted to accommodate the diagnostic decision. For example, the threshold for diagnosing a bacterial infection may be lowered to favor test sensitivity and thus reduce the possibility of a potentially life-threatening false negative result.

A flowchart for training a classifier:

1. Use biological samples obtained from a population of subjects with each of the conditions of interest, where the subject condition is determined using a "gold standard" method (e.g., clinical adjudication). These conditions are infection, sepsis, SIRS (or non-infectious illness), bacterial infection, viral infection, fungal infection, or are healthy.
2. Measure gene expression of the host response signature genes.
3. Normalize the gene expression values.
4. Generate the classifiers, e.g., for sepsis, infection, etc. through a computational, iterative process to identify the weighting value for each gene target such that classification performance is optimized.
5. Record the gene targets with non-zero weights ($X_1, \ldots X_d$), e.g., the value of the weight associated with each gene target ($w_1, \ldots, w_d$), and the threshold value that achieves optimal classification performance for each classification task, to a database associated with the specific testing platform.
6. There may be databases for, A) the gene targets, B) the weights, and C) the threshold values.

Development of Tests

Accordingly, in embodiments of the inventive concept, classifiers derived from the host response signature may be used in methods of determining etiology of an infection in a subject. For example, in some embodiments, methods of determining etiology of an infection may include detecting the presence or absence of an infection, wherein presence of an infection may be indicative of the presence of sepsis in the subject, and absence of an infection may be indicative of the presence of SIRS/non-infectious illness in the subject. In some embodiments, detecting the presence of an infection may include identifying the pathogen class (bacterial, fungal, or viral) that can be causing the infection. In some embodiments, detecting the presence of an infection may include identifying the pathogen class that can be causing sepsis. Gene expression-based classifiers can be developed that can be used to identify and/or characterize the etiology of an infection with a high degree of accuracy.

According to some embodiments, the present inventive concept provides a method of developing a test, such as, for example, a host response classifier and host response signature, the signature comprising: obtaining/measuring gene expression levels from a plurality of biological subjects and various sources (e.g. peripheral blood samples in in vivo samples, in vitro samples and ex vivo samples), such as biological sources/subjects having/suffering from an infection, sepsis, bacterial infections, fungal infections, viral infections, non-infectious illness or healthy; and selecting a pre-defined group of genes, wherein genes in the pre-defined group are selected for having a differential gene expression where an infection can be present and where an infection can be absent, where sepsis can be present and where sepsis can be absent, where a bacterial infection can be present and where a bacterial infection can be absent, where a fungal infection can be present and where a fungal infection can be absent, and/or where a viral infection can be present and where a viral infection can be absent, and wherein the differential gene expression in the pre-defined set of genes, and the weights determined during classifier training, may be used to generate, for example, an infection classifier, a sepsis classifier, a bacterial infection classifier, a fungal infection classifier, a viral infection classifier, a non-infectious illness classifier, or a SIRS classifier.

In some embodiments, the test can differentiate among a bacterial infection, a fungal infection, and/or a viral infection. In some embodiments, the test can identify a sample that has a bacterial infection. In some embodiments, the test can identify a sample that has a fungal infection. In some embodiments, the test can identify a sample that has a viral infection. In some embodiments, the test can identify a sample that has both a bacterial infection and a fungal infection. In some embodiments, the test can identify a sample that has both a bacterial infection and a viral infection. In some embodiments, the test can identify a sample that has both a fungal infection and a viral infection. In some embodiments, the test can identify a sample that has a bacterial infection, a viral infection, and a fungal infection. In some embodiments, the best can differentiate between an infected sample (e.g., a sample infected with a bacterial infection, a viral infection, and/or a fungal infection) and a non-infected sample (e.g., healthy or SIRS). In some embodiments, the test can identify a sample that has an infection indicative of sepsis.

In some embodiments, the sample is not purified after collection. In some embodiments, the sample may be purified to remove extraneous material, before or after lysis of cells. In some embodiments, the sample can be purified with cell lysis and removal of cellular materials, isolation of nucleic acids, and/or reduction of abundant transcripts, such as, for example, globin and/or ribosomal RNAs.

In some embodiments, biological sources from which gene expression levels are measured include samples from human subjects ("in vivo"), such as blood samples, cultured cells ("in vitro"), and primary human tissues ("ex vivo"). In some embodiments, gene expression levels may be measured by isolating RNA from a biological source, e.g., total RNA to create a transcriptome, and quantitating gene expression levels from the pre-defined group of genes expressed in the RNA. In some embodiments, gene expression levels from the pre-defined group of genes are normalized, e.g., adjusted relative to one or more genes whose expression levels do not change as a result of the state (infection, sepsis, fungal, bacterial or viral infection, or non-infectious illness). Normalizing can be performed to remove variability that may be inherent to the source of the sample, the assay methodology or measurement modality of the testing platform to give a quantity or relative quantity, e.g., for expressed genes.

In some embodiments of the inventive concept, biological samples, including those from a cohort of patients encompassing, for example, infection, sepsis, bacterial infections, fungal infections, viral infections, healthy, and/or SIRS/non-infectious illness are used to generate gene expression-based classifiers for each condition. Specifically, the infection classifier can be obtained to positively identify those with an infection versus those without an infectious illness; the sepsis classifier can be obtained to positively identify those with sepsis versus those without an infectious illness or versus those with SIRS; the bacterial infection classifier can be obtained to positively identify those with bacterial infection vs. those without; the viral infection classifier can be obtained to positively identify those with viral infection vs. those without; the fungal infection classifier can be obtained to positively identify those with fungal infection vs. those without. Inclusion of the non-infectious illness samples improves the specificity for classification of patients with infection, sepsis, bacterial infection, fungal infection, or viral infection. Next, signatures for infection classifiers, sepsis classifiers, bacterial infection classifiers, fungal infection classifiers, viral infection classifiers, and/or non-infectious illness classifiers are generated (e.g., by applying a sparse logistic regression model). In some embodiments of the inventive concept, using classifiers includes (i) measuring gene expression/transcript levels, which may include normalizing expression/transcript levels in, for example, a sample derived from a subject, (ii) applying a classifier or classifiers, e.g., a sepsis classifier, as a test and obtaining a score for whether a subject/patient has, e.g., sepsis, and (iii) comparing the score to a pre-defined threshold, cut-off value, or range or bands of values indicative of the likelihood for the presence and/or absence of sepsis. It will be appreciated that application of more than one classifier may include sequentially applying the classifiers, e.g., first, applying a classifier to determine if an infection and/or sepsis is present, and second, applying a classifier to determine whether the infection is bacterial in nature, viral in nature, or fungal in nature, or simultaneously applying multiple classifiers and obtaining a score/probability whether a subject belongs to one of several categories (infection/sepsis, bacterial, viral, fungal). The application of more than one classifier may occur simultaneously, e.g., determining bacterial infection versus no bacterial infection, determining viral infection versus no viral infection, determining fungal infection versus no fungal infection, or even the determination of one type of infection versus another, e.g., the determination of bacterial versus viral infection.

Individual classifiers may be combined into a single classifier by following a one-versus-all scheme whereby largest membership probability assigns class label. In some embodiments, the combined classifier may be validated using leave-one-out cross-validation in the same population from which it was derived and/or may be validated using publicly available human gene expression datasets of samples from subjects suffering from illness of known etiology. For example, validation may be performed using publicly available human gene expression datasets (e.g., GSE6269, GSE42026, GSE40396, GSE20346, and/or GSE42834), the datasets chosen if they include at least two clinical groups (infection/sepsis, bacterial, fungal, viral, or non-infectious illness).

The classifier may be validated in a standard set of samples, for example, blood samples and/or samples containing RNA, from subjects suffering from illness of known etiology, e.g., infection/sepsis, bacterial infection, fungal infection, viral infection, or non-infectious illness.

The methodology for generating classifiers as described herein may be readily translated to different gene expression platforms, e.g., mRNA detection and quantification, platforms. In addition to the platforms set forth herein, methods for mRNA detection and quantification using proprietary platforms are described in International Application No. PCT/US2016/040437, the disclosure of which is incorporated by reference in its entirety.

Real-time PCR may be used to quickly identify gene expression from a whole blood sample. For example, the isolated mRNA can be reverse transcribed and then amplified and detected in real time using non-specific fluorescent dyes that intercalate with the resulting ds-DNA, or sequence-specific DNA probes labeled with a fluorescent reporter which permits detection after hybridization of the probe with its complementary DNA target.

Hence, it can be understood that there are many methods of mRNA quantification and detection that may be used by a platform in accordance with the methods of the inventive concept as set forth herein. The expression levels can be normalized following detection and quantification as appropriate for the particular platform.

With mRNA detection and quantification and a matched normalization methodology in place for a platform, it is simply a matter of using carefully selected and adjudicated patient samples for the training methods. These subject-samples can also be used to generate coefficients and cutoffs for a test implemented using a different mRNA detection and quantification platform.

In some embodiments, the individual categories of classifiers (e.g., infection, sepsis, bacterial infection, fungal infection, viral infection, non-infectious illness) are formed from a cohort inclusive of a variety of such causes thereof. For instance, the bacterial infection classifier can be obtained from a cohort having bacterial infections from multiple bacterial genera and/or species, the viral infection classifier can be obtained from a cohort having viral infections from multiple viral genera and/or species, the fungal infection classifier can be obtained from a cohort having fungal infections from multiple fungal general and/or species, and the non-infectious illness classifier can be obtained from a cohort having a non-infectious illness due to multiple non-infectious causes. In this way, the respective classifiers obtained are agnostic to the specific bacteria, fungus, virus, or non-infectious cause. In some embodiments, some, or all of the subjects with non-infectious causes of illness in the cohort have symptoms consistent with an infection, for example, a non-infectious process whose symptoms overlap with those of an infection.

In some embodiments, signatures may be obtained using a supervised statistical approach known as sparse linear classification in which sets of genes are identified by the model according to their ability to separate phenotypes during a training process that uses the selected set of patient samples. The outcomes of training are signatures and classification coefficients for the comparisons. Together the signatures and coefficients provide a classifier or predictor. Training may also be used to establish threshold or cutoff values. Threshold or cutoff values can be adjusted to change test performance, e.g., test sensitivity and specificity. For example, the threshold for a bacterial infection may be intentionally lowered to increase the sensitivity of a test for the presence of sepsis, for example, to reduce the possibility of a false negative result.

In some embodiments, generating the classifier includes iteratively: (i) assigning a weight for each gene in the signature, in some embodiments, for each normalized gene expression value, entering the weight and expression value for each gene into a classifier equation and determining a score or outcome for each of the plurality of subjects, then (ii) determining the accuracy of classification for each outcome across the plurality of subjects, and then (iii) adjusting the weight until accuracy of classification is optimized. Genes having a non-zero weight are included in the final form of the respective classifier. The generated classifier or classifiers of the inventive concept may be used to analyze expression levels of genes in a sample/subject to provide a score, that may be converted to a probability that indicates the likelihood of, for example, the presence or absence of an infection, such as a presence or absence of sepsis; and/or the etiology of an infection, such as a bacterial, a viral, a fungal infection, or a non-infectious illness/disorder, in the subject.

In some embodiments, the classifier can be a linear regression classifier and said generating includes converting a score of said classifier to a probability using a link function. The link function can specify the link between the target/output of the model (e.g., probability of having an infection/sepsis) and systematic components (in this instance, the combination of explanatory variables that include the predictor) of the linear model. It conveys how the expected value of the response relates to the linear predictor of explanatory variable.

Methods of Determining Classifications

The inventive concept further provides methods for determining whether a subject has an infection versus a non-infectious illness, and/or illness due to a bacterial infection, a fungal infection, a viral infection, or a non-infectious cause. In some embodiments, the determining whether a subject has an infection versus no infection or non-infectious illness may include determining that a subject has sepsis if an infection is present, and determining the patient has non-infectious illness in the absence of an infection. The methods for making this determination rely upon use of classifiers provided as described herein. The methods may include: measuring gene expression levels of a pre-defined set of genes in a sample from a subject; analyzing the gene expression levels measured in the sample with classifiers of presence or absence of an infection and/or etiology of an infection; and determining if an infection is present and/or the etiology of infection in the subject from the analyzing of the gene expression levels with the classifiers. The gene expression levels measured may be normalized for the technology/platform used to make the measurement. The classifiers may have pre-defined weighting values (coefficients) for each gene in the group/pre-defined set of genes. The analysis of gene expression levels with the classifiers may include comparing the sum of the weighted and normalized gene expression levels of a pre-defined set of genes in the signature to pre-defined thresholds, cut-off values, confidence intervals and/or ranges of values that provide a likelihood or probability for the presence of an infection and/or the etiology of an infection.

Examples of methods of the inventive concept is as follows. In some embodiments, a gene "signature" may be informative of a host response of the patient to presence of an infection, different etiologies of infection (bacterial, fungal, viral), or to an ill, but not infected state. The signature includes a group of genes that have consistent and coordinated increased or decreased levels of expression in response to one of the clinical states of interest, for example, a bacterial infection, fungal infection, viral infection, or a non-infected but ill state. In some embodiments, the clinical state may be presence of an infection, which may be indicative of the presence of sepsis, or a non-infected but ill state, which can be indicative of the presence of a non-infectious illness/SIRS in the subject/patient. These signatures may be derived using gene expression data from samples obtained from carefully adjudicated groups of samples with the condition(s) of interest (training).

A signature can be indicative of a clinical state and can be defined relative to at least one of the other two possibilities. For example, the infection signature can be identified as a group of genes (a biomarker), and specifically by the level of expression of those genes, that distinguish patients with an infection from those with no infection (non-infectious illness including SIRS and/or healthy). The bacterial infection signature can be identified as a group of genes (a biomarker), specifically by the level of expression of those genes, that distinguish patients with a bacterial infection and those without a bacterial infection, including patients/samples with a fungal infection, a viral infection, a non-infectious illness, or the healthy state as it pertains to this inventive concept as described herein. The fungal infection signature can be defined by a group of differentially expressed genes that distinguish patients/samples with a fungal infection from those without a fungal infection, including patients with either a bacterial infection, a viral infection, a non-infectious illness, or the healthy state. The viral infection signature can be defined by a group of differentially expressed genes that distinguish patients/samples with a viral infection from those without a viral infection, including patients with either a bacterial infection, a fungal infection, a non-infectious illness, or the healthy state. The non-infectious illness signature can be defined by a group of differentially expressed genes that distinguish patients with non-infectious causes of illness relative to those with either bacterial, fungal, or viral infections.

As would be understood by one skilled in the art, the value of the coefficients for each independent variable will change for each technology platform used to measure the expression of the genes or a subset of genes used in the regression model.

The sensitivity, specificity, and overall accuracy of each classifier may be optimized by changing the threshold for classification using receiving operating characteristic (ROC) curves as a guide.

The classifiers that are developed during training and using a training set of samples are applied for prediction purposes to deliver a patient-specific result, a process known as classification (see https://www.fda.gov/regulatory-information/search-fda-guidance-documents/vitro-diagnostic-multivariate-index-assays-draft-guidance-industry-clinical-laboratories-and-fda, accessed Apr. 30, 2021). To provide a single, patient-specific result, a biological sample can be taken from a patient and the normalized levels of gene expression (e.g., the relative amount of mRNA expression) in the sample of each of the genes specified in the signature, or subset of signature genes, are entered into the classifiers. The weighting coefficients for each gene that are discovered during training are also downloaded from a database and entered into the classifier or classifiers, which takes the form of a linear or probit regression equation. As outputs, the classifier or classifiers compute a probability value or values or scores. Each probability value or score may be used to determine the likelihood of the considered clinical states: infection, sepsis, bacterial infection, fungal infection, viral infection, or non-infectious illness.

In some embodiments, the results of one or more of the classifiers—e.g., the probability a patient has an infection or a non-infectious illness, or the probability the new subject or patient has an infection, a bacterial infection, a fungal infection, or a viral infection are reported. In final form, the signatures with their corresponding weights (coefficients) are applied to an individual patient to obtain probability values or scores, e.g., a probability of having an infection, having sepsis, a bacterial infection, a fungal infection, a viral infection, or a non-infectious illness. In some embodiments, these values may be reported relative to a reference range that indicates the confidence with which the classification is made. In some embodiments, the output of an individual classifier or multiple classifiers may be compared to a threshold or cutoff value or values (for multiple classifiers). For example, to report a "positive" in the case that the classifier score or probability exceeds the threshold indicating the presence of one or more of an infection, of sepsis, of a bacterial infection, a fungal infection, and/or a viral infection, or a non-infectious illness. These reference ranges and threshold or cutoff values are also determined during classifier training. If the classifier score or probability fails to reach the threshold, the result can be reported as "negative" for the respective condition.

It can be noted that a classifier obtained with one platform may not show optimal performance on another platform. This can be due to the promiscuity of probes, methods of detection, or other technical issues particular to the platform. Accordingly, also described herein are methods to adapt a signature as taught herein from one platform for another. For example, a signature obtained from a TLDA platform may be adapted to a Qvella platform by the use of corresponding Qvella probes for the genes in the signature and/or substitute genes correlated with those in the signature obtained from the TLDA platform. "Substitute genes" may be introduced as replacements for those that either may not perform well on the Qvella platform for technical reasons or to replace those for which there is no cognate Qvella probe. These replacements may indicate highly correlated genes or may be probes that bind to a different location in the same gene transcript. Additional genes may be included.

Methods of Treatment

Another embodiment of the inventive concept includes methods of treating an infection whose etiology is unknown in a subject comprising: obtaining a sample from the subject; determining a gene expression profile for the subject from the sample by evaluating the expression levels of a pre-defined set of genes; analyzing the expression levels with a bacterial classifier, a fungal classifier, a viral classifier or a non-infectious illness classifier that have pre-defined weighting values (coefficients) for each of the genes in the pre-defined set for each classifier; comparing the output of the classifiers to pre-defined thresholds, cut-off values, or ranges of values that indicate likelihood of infection; classifying the sample as having an infection of bacterial etiology, fungal etiology, or viral etiology, or having a noninfectious illness; and administering to the subject an appropriate treatment regimen for an etiology of infection as identified in the classifying step. The method may include normalizing the expression levels as may be required for the technology used to make said measurement to generate normalized values for gene expression and analyzing the normalized values for gene expression as described above.

In some embodiments, treating an infection of unknown etiology may include treating sepsis, wherein analyzing the normalized values for gene expression includes analyzing with an infection classifier and a non-infectious illness classifier, and wherein classification includes classifying the sample as having an infection or sepsis, or as having a noninfectious illness.

In some embodiments, the administering step includes administering an antibacterial therapy when the etiology of infection is determined to be bacterial. In some embodiments, the administering step includes administering an antifungal therapy when the etiology of the infection is determined to be fungal. In some embodiments, the administering step includes administering an antiviral therapy when the etiology of the infection is determined to be viral. In some embodiments, the administering step includes administering an anti-inflammatory agent when the etiology of the illness is determined to be non-infectious illness. In some embodiments, subjects classified with a noninfectious illness may be referred for further diagnosis or treatment.

The person obtaining the sample, for example, a blood sample, may not perform the comparison. However, it is contemplated that a laboratory may communicate the output of one or more classifiers in the form of a score or probability, the threshold, cutoff or range of values for comparison, with or without an interpretation of the score in relation to said threshold, cutoff, or range of value to a clinician for the purpose of identifying the presence of infection, the etiology of an infection, the presence of non-infectious illness for the administration of an appropriate treatment. In some instances, the laboratory may communicate the gene expression values of the genes comprising the signature or signatures. It is also contemplated that a clinician/medical professional, after examining a patient/subject, can order a sample be obtained, such as a peripheral blood sample, and/or assayed by another, and have the test result of the patient/subject reported back to the clinician/medical professional. The clinician/medical professional can then direct/order suitable treatment.

In other embodiments of the inventive concept, provided is a kit for determining presence or absence of an infection or non-infectious illness, and/or the etiology of an infection in a subject comprising: a method for extracting a biological sample; a method for generating one or more arrays/measuring gene expression levels including a plurality of synthetic oligonucleotides with regions homologous to a group/pre-defined set of gene transcripts as described herein; and instructions for use.

Classification Systems

A classification system, computer program product, and/or computer-implemented methods may be used in or by a platform, according to various embodiments described herein. A classification system, computer program product, and/or computer-implemented method may be embodied as one or more enterprise, application, personal, pervasive and/or embedded computer systems that are operable to receive, transmit, process and store data using any suitable combination of software, firmware and/or hardware and that may be standalone and/or interconnected by any conventional, public and/or private, real and/or virtual, wired and/or wireless network including all or a portion of the global communication network known as the Internet, and may include various types of tangible, non-transitory computer readable medium. Hardware on which classification systems, computer program products and/or computer-implemented methods of the inventive concept may be used is not particularly limited, and may include, without limitation, personal computers, handheld and/or mobile devices, phones, etc. In some embodiments, the systems, computer programs, and/or compute-implemented methods of the inventive concept may be cloud-based.

The classification system may include a processor subsystem, including one or more Central Processing Units (CPU) on which one or more operating systems and/or one or more applications run. It will be understood that multiple processors may be present, which may be either electrically interconnected or separate. Processor(s) are configured to execute computer program code from memory devices, such as memory, to perform at least some of the operations and methods described herein, and may be any conventional or special purpose processor, including, but not limited to, digital signal processor (DSP), field programmable gate array (FPGA), application specific integrated circuit (ASIC), and multi-core processors.

The memory subsystem may include a hierarchy of memory devices such as random access memory (RAM), read-only memory (ROM), erasable programmable read-only memory (EPROM) or flash memory, and/or any other solid state memory devices.

A storage circuit may also be provided, which may include, for example, a portable computer diskette, a hard disk, a portable compact disk read-only memory (CDROM), an optical storage device, a magnetic storage device and/or any other kind of disk- or tape-based storage subsystem. The storage circuit may be provided on hardware including, but not limited to, computers, such as personal computers (PCs), mobile/handheld devices, such as tablets and/or mobile phones, etc., or may be provided on the cloud. The storage circuit may provide non-volatile storage of data/parameters/classifiers for the classification system. The storage circuit may include disk drive and/or network store components. The storage circuit may be used to store code to be executed and/or data to be accessed by the processor. In some embodiments, the storage circuit may store databases which provide access to the data/parameters/classifiers used for the classification system such as the signatures, weights, thresholds, etc. Any combination of one or more computer readable media may be utilized by the storage circuit. The computer readable media may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium can include the following: a portable computer diskette, a hard disk, a random access memory (RAM), a read-only memory (ROM), an erasable programmable read-only memory (EPROM or flash memory), a portable compact disc read-only memory (CD-ROM), an optical storage device, a magnetic storage device, or any suitable combination of the foregoing. As used herein, a computer readable storage medium may be any tangible medium that can contain or store a program for use by or in connection with an instruction execution system, apparatus, or device.

An input/output circuit may include displays and/or user input devices, such as keyboards, touch screens and/or pointing devices. Devices attached to the input/output circuit may be used to provide information to the processor by a user of the classification system. Devices attached to the input/output circuit may include networking or communication controllers, input devices (keyboard, a mouse, touch screen, etc.) and output devices (printer or display). The input/output circuit may also provide an interface to devices, such as a display and/or printer, to which results of the operations of the classification system can be communicated so as to be provided to the user of the classification system.

An optional update circuit may be included as an interface for providing updates to the classification system. Updates may include updates to the code executed by the processor that are stored in the memory and/or the storage circuit. Updates provided via the update circuit may also include updates to portions of the storage circuit related to a database and/or other data storage format which maintains information for the classification system, such as the signatures, weights, thresholds, etc.

The sample input circuit of the classification system may provide an interface for the platform as described hereinabove to receive biological samples to be analyzed. The sample input circuit may include mechanical elements, as well as electrical elements, which receive a biological sample provided by a user to the classification system and transport the biological sample within the classification system and/or platform to be processed. The sample input circuit may include a bar code reader that identifies a bar-coded container for identification of the sample and/or test order form. The sample processing circuit may further process the biological sample within the classification system and/or platform so as to prepare the biological sample for automated analysis. The sample analysis circuit may automatically analyze the processed biological sample. The sample analysis circuit may be used in measuring, e.g., gene expression levels of a group/pre-defined set of genes with the biological sample provided to the classification system. The sample analysis circuit may also generate normalized gene expression values by normalizing the gene expression levels. The sample analysis circuit may retrieve from the storage circuit a classifier for infection, a classifier for sepsis, a bacterial infection classifier, a fungal infection classifier, a viral infection classifier and a non-infectious illness classifier, these classifier(s) comprising pre-defined weighting values (e.g., coefficients) for each of the genes of the group/pre-defined set of genes. The sample analysis circuit may enter the normalized gene expression values into one or more infection classifiers selected from the infection classifier, the sepsis classifier, the bacterial infection classifier, the fungal infection classifier, the viral infection classifier, and the non-infectious illness classifier, the no infection classifier. The sample analysis circuit may calculate and/or determine a probability for one or more of the presence of infection, of sepsis, of a bacterial infection, fungal infection, viral infection and non-infectious illness based upon said classifier(s), and control output, via the input/output circuit, of a report/determination whether an infection or sepsis is present or absent, or whether the infection in the subject is bacterial in origin, fungal in origin, viral in origin, non-infectious in origin, or some combination thereof. In some embodiments, the sample analysis circuit may calculate and/or determine a probability or score for the presence of an infection or absence of an infection/presence of a non-infectious illness, wherein presence of an infection is indicative of a presence of sepsis, and absence of an infection is indicative of a presence of non-infectious illness.

The sample input circuit, the sample processing circuit, the sample analysis circuit, the input/output circuit, the storage circuit, and/or the update circuit may execute at least partially under the control of the one or more processors of the classification system. As used herein, executing "under the control" of the processor means that the operations performed by the sample input circuit, the sample processing circuit, the sample analysis circuit, the input/output circuit, the storage circuit, and/or the update circuit may be at least partially executed and/or directed by the processor, but does not preclude at least a portion of the operations of those components being separately electrically or mechanically automated. The processor may control the operations of the classification system, as described herein, via the execution of computer program code.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the classification system, partly on the classification system, as a stand-alone software package, partly on the classification system and partly on a remote computer or entirely on the remote computer or server. In the latter scenario, the remote computer may be connected to the classification system through any type of network, including a local area network (LAN) or a wide area network (WAN), or the connection may be made to an external computer (for example, through the Internet using an Internet Service Provider) or in a cloud computer environment or offered as a service such as a Software as a Service (SaaS).

In some embodiments, the system includes computer readable code that can transform quantitative, or semi-quantitative, detection of gene expression to a cumulative score or probability of the etiology of an infection. In some embodiments, the system includes computer readable code that can transform quantitative, or semi-quantitative, detection of gene expression to a cumulative score or probability of a presence or absence of an infection, wherein presence of an infection may be indicative of the presence of sepsis, and absence of an infection may be indicative of the presence of non-infectious illness or SIRS.

In some embodiments, the system can be a sample-to-result system, with the components integrated such that a user can simply insert a biological sample to be tested, and a period of time later (e.g., a short amount of time, e.g., 10, 30 or 45 minutes, or 1, 2, or 3 hours, up to 8, 12, 24 or 48 hours) receive a result output from the system.

Trained Algorithms

After using one or more assays to process one or more samples derived from the subject to generate one or more datasets indicative of sepsis due to a bacterial infection, a fungal infection, and/or a viral infection, or datasets indicative of non-infection (e.g., SIRS), a trained algorithm may be used to process one or more of the datasets (e.g., at each of a plurality of sepsis-related state-associated genomic loci) to determine the sepsis-related state or a non-sepsis-related state. For example, the trained algorithm may be used to determine quantitative measures of sequences at each of the plurality of sepsis-related state-associated genomic loci in the samples. The trained algorithm may be configured to identify the sepsis-related state or the non-sepsis related state (e.g., SIRS) with an accuracy of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more than 99% for at least about 25, at least about 50, at least about 100, at least about 150, at least about 200, at least about 250, at least about 300, at least about 350, at least about 400, at least about 450, at least about 500, or more than about 500 independent samples.

The trained algorithm may comprise a supervised machine learning algorithm. The trained algorithm may comprise a classification and regression tree (CART) algorithm. The supervised machine learning algorithm may comprise, for example, a Random Forest, a support vector machine (SVM), a neural network, or a deep learning algorithm. The trained algorithm may comprise an unsupervised machine learning algorithm.

The trained algorithm may be configured to accept a plurality of input variables and to produce one or more output values based on the plurality of input variables. The plurality of input variables may comprise one or more datasets indicative of a sepsis-related state or a non-sepsis related state (e.g., SIRS). For example, an input variable may comprise a number of sequences corresponding to or aligning to each of the plurality of sepsis-related state-associated genomic loci. The plurality of input variables may also include clinical health data of a subject.

The trained algorithm may comprise a classifier, such that each of the one or more output values comprises one of a fixed number of possible values (e.g., a linear classifier, a logistic regression classifier, etc.) indicating a classification of the sample by the classifier. The trained algorithm may comprise a binary classifier, such that each of the one or more output values comprises one of two values (e.g., {0, 1}, {positive, negative}, or {sepsis, non-sepsis}) indicating a classification of the sample by the classifier. The trained algorithm may be another type of classifier, such that each of the one or more output values comprises one of more than two values (e.g., {0, 1, 2} or {bacterial infection, fungal infection, or viral infection}) indicating a classification of the sample by the classifier. The output values may comprise descriptive labels, numerical values, or a combination thereof. Some of the output values may comprise descriptive labels. Such descriptive labels may provide an identification or indication of the disease or disorder state of the subject, and may comprise, for example, positive, negative, sepsis, not-sepsis, SIRS, fungal infection, bacterial infection, viral infection, or indeterminate. Such descriptive labels may provide an identification of a treatment for the subject's sepsis-related state or non-sepsis-related state, and may comprise, for example, a therapeutic intervention, a duration of the therapeutic intervention, and/or a dosage of the therapeutic intervention suitable to treat a sepsis-related condition or a SIRS-related condition. Such descriptive labels may provide an identification of secondary clinical tests that may be appropriate to perform on the subject, and may comprise, for example, an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof. For example, such descriptive labels may provide a prognosis of the sepsis-related state of the subject. As another example, such descriptive labels may provide a relative assessment of the sepsis-related state of the subject. Some descriptive labels may be mapped to numerical values, for example, by mapping "positive" to 1 and "negative" to 0.

Some of the output values may comprise numerical values, such as binary, integer, or continuous values. Such binary output values may comprise, for example, {0, 1},{positive, negative}, or {sepsis, not sepsis}. Such integer output values may comprise, for example, {0, 1, 2}. Such continuous output values may comprise, for example, a probability value of at least 0 and no more than 1. Such continuous output values may comprise, for example, an un-normalized probability value of at least 0. Such continuous output values may indicate a prognosis of the sepsis-related state of the subject. Some numerical values may be mapped to descriptive labels, for example, by mapping 1 to "positive" and 0 to "negative."

Some of the output values may be assigned based on one or more cutoff values. For example, a binary classification of samples may assign an output value of "positive" or 1 if the sample indicates that the subject has at least a 50% probability of having a sepsis-related state (e.g., a bacterial, fungal, and/or viral infection). For example, a binary classification of samples may assign an output value of "negative" or 0 if the sample indicates that the subject has less than a 50% probability of having a sepsis-related state (e.g., a bacterial, fungal, and/or viral infection). In this case, a single cutoff value of 50% is used to classify samples into one of the two possible binary output values. Examples of single cutoff values may include about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, and about 99%.

As another example, a classification of samples may assign an output value of "positive" or 1 if the sample indicates that the subject has a probability of having a sepsis-related state (e.g., a bacterial, fungal, and/or viral infection) of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more. The classification of samples may assign an output value of "positive" or 1 if the sample indicates that the subject has a probability of having a sepsis-related state (e.g., a bacterial, fungal, and/or viral infection) of more than about 50%, more than about 55%, more than about 60%, more than about 65%, more than about 70%, more than about 75%, more than about 80%, more than about 85%, more than about 90%, more than about 91%, more than about 92%, more than about 93%, more than about 94%, more than about 95%, more than about 96%, more than about 97%, more than about 98%, or more than about 99%.

The classification of samples may assign an output value of "negative" or 0 if the sample indicates that the subject has a probability of having a sepsis-related state (e.g., a bacterial, fungal, and/or viral infection) of less than about 50%, less than about 45%, less than about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1%. The classification of samples may assign an output value of "negative" or 0 if the sample indicates that the subject has a probability of having a sepsis-related state (e.g., a bacterial, fungal, and/or viral infection) of no more than about 50%, no more than about 45%, no more than about 40%, no more than about 35%, no more than about 30%, no more than about 25%, no more than about 20%, no more than about 15%, no more than about 10%, no more than about 9%, no more than about 8%, no more than about 7%, no more than about 6%, no more than about 5%, no more than about 4%, no more than about 3%, no more than about 2%, or no more than about 1%.

The trained algorithm may be trained with a plurality of independent training samples. Each of the independent training samples may comprise a sample from a subject, associated datasets obtained by assaying the sample (as described elsewhere herein), and one or more known output values corresponding to the sample (e.g., a clinical diagnosis, prognosis, absence, or treatment efficacy of a sepsis-related state of the subject). Independent training samples may comprise samples and associated datasets and outputs obtained or derived from a plurality of different subjects. Independent training samples may comprise samples and associated datasets and outputs obtained at a plurality of different time points from the same subject (e.g., on a regular basis such as weekly, biweekly, or monthly). Independent training samples may be associated with presence of the sepsis-related state (e.g., training samples comprising samples and associated datasets and outputs obtained or derived from a plurality of subjects known to have the sepsis-related state). Independent training samples may be associated with absence of the sepsis-related state (e.g., training samples comprising samples and associated datasets and outputs obtained or derived from a plurality of subjects who are known to not have a previous diagnosis of the sepsis-related state or who have received a negative test result for the sepsis-related state). Independent training samples may be associated with presence of the non-sepsis-related state (e.g., training samples comprising samples and associated datasets and outputs obtained or derived from a plurality of subjects known to have the non-sepsis-related state). Independent training samples may be associated with presence of a SIRS-related state (e.g., training samples comprising samples and associated datasets and outputs obtained or derived from a plurality of subjects known to have the SIRS-related state).

The trained algorithm may be trained with at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The independent training samples may comprise samples associated with presence of the sepsis-related state and/or samples associated with absence of the sepsis-related state. The trained algorithm may be trained with no more than about 500, no more than about 450, no more than about 400, no more than about 350, no more than about 300, no more than about 250, no more than about 200, no more than about 150, no more than about 100, or no more than about 50 independent training samples associated with presence of the sepsis-related state. In some embodiments, the sample is independent of samples used to train the trained algorithm.

The trained algorithm may be trained with a first number of independent training samples associated with presence of the sepsis-related state and a second number of independent training samples associated with absence of the sepsis-related state. The first number of independent training samples associated with presence of the sepsis-related state may be no more than the second number of independent training samples associated with absence of the sepsis-related state. The first number of independent training samples associated with presence of the sepsis-related state may be equal to the second number of independent training samples associated with absence of the sepsis-related state. The first number of independent training samples associated with presence of the sepsis-related state may be greater than the second number of independent training samples associated with absence of the sepsis-related state.

The trained algorithm may be configured to identify the sepsis-related state at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more; for at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The accuracy of identifying the sepsis-related state by the trained algorithm may be calculated as the percentage of independent test samples (e.g., subjects known to have the sepsis-related state or subjects with negative clinical test results for the sepsis-related state) that are correctly identified or classified as having or not having the sepsis-related state.

The trained algorithm may be configured to identify the sepsis-related state with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the sepsis-related state using the trained algorithm may be calculated as the percentage of samples identified or classified as having the sepsis-related state that correspond to subjects that truly have the sepsis-related state.

The trained algorithm may be configured to identify the sepsis-related state with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the sepsis-related state using the trained algorithm may be calculated as the percentage of samples identified or classified as not having the sepsis-related state that correspond to subjects that truly do not have the sepsis-related state.

The trained algorithm may be configured to identify the sepsis-related state with a clinical sensitivity at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the sepsis-related state using the trained algorithm may be calculated as the percentage of independent test samples associated with presence of the sepsis-related state (e.g., subjects known to have the sepsis-related state) that are correctly identified or classified as having the sepsis-related state.

The trained algorithm may be configured to identify the sepsis-related state with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the sepsis-related state using the trained algorithm may be calculated as the percentage of independent test samples associated with absence of the sepsis-related state (e.g., subjects with negative clinical test results for the sepsis-related state) that are correctly identified or classified as not having the sepsis-related state.

The trained algorithm may be configured to identify the sepsis-related state with an Area-Under-Curve (AUC) of at least about 0.50, at least about 0.55, at least about 0.60, at least about 0.65, at least about 0.70, at least about 0.75, at least about 0.80, at least about 0.81, at least about 0.82, at least about 0.83, at least about 0.84, at least about 0.85, at least about 0.86, at least about 0.87, at least about 0.88, at least about 0.89, at least about 0.90, at least about 0.91, at least about 0.92, at least about 0.93, at least about 0.94, at least about 0.95, at least about 0.96, at least about 0.97, at least about 0.98, at least about 0.99, or more. The AUC may be calculated as an integral of the Receiver Operator Characteristic (ROC) curve (e.g., the area under the ROC curve) associated with the trained algorithm in classifying samples as having or not having the sepsis-related state.

The trained algorithm may be configured to identify the SIRS-related state with an Area-Under-Curve (AUC) of at least about 0.50, at least about 0.55, at least about 0.60, at least about 0.65, at least about 0.70, at least about 0.75, at least about 0.80, at least about 0.81, at least about 0.82, at least about 0.83, at least about 0.84, at least about 0.85, at least about 0.86, at least about 0.87, at least about 0.88, at least about 0.89, at least about 0.90, at least about 0.91, at least about 0.92, at least about 0.93, at least about 0.94, at least about 0.95, at least about 0.96, at least about 0.97, at least about 0.98, at least about 0.99, or more. The AUC may be calculated as an integral of the Receiver Operator Characteristic (ROC) curve (e.g., the area under the ROC curve) associated with the trained algorithm in classifying samples as having or not having the SIRS-related state.

The trained algorithm may be adjusted or tuned to improve one or more of the performance, accuracy, PPV, NPV, clinical sensitivity, clinical specificity, or AUC of identifying the sepsis-related state or the non-sepsis-related state (e.g., SIRS). The trained algorithm may be adjusted or tuned by adjusting parameters of the trained algorithm (e.g., a set of cutoff values used to classify a sample as described elsewhere herein, or weights of a neural network). The trained algorithm may be adjusted or tuned continuously during the training process or after the training process has completed.

After the trained algorithm is initially trained, a subset of the inputs may be identified as most influential or most important to be included for making high-quality classifications. For example, a subset of the plurality of sepsis-related state-associated genomic loci may be identified as most influential or most important to be included for making high-quality classifications or identifications of sepsis-related states (or sub-types of sepsis-related states). The plurality of sepsis-related state-associated genomic loci or a subset thereof may be ranked based on classification metrics indicative of each genomic locus's influence or importance toward making high-quality classifications or identifications of sepsis-related states (or sub-types of sepsis-related states (e.g., bacterial infection, fungal infection, and/or viral infection)). Such metrics may be used to reduce, in some cases significantly, the number of input variables (e.g., predictor variables) that may be used to train the trained algorithm to a desired performance level (e.g., based on a desired minimum accuracy, PPV, NPV, clinical sensitivity, clinical specificity, AUC, or a combination thereof). For example, if training the trained algorithm with a plurality comprising several dozen or hundreds of input variables in the trained algorithm results in an accuracy of classification of more than 99%, then training the trained algorithm instead with only a selected subset of no more than about 5, no more than about 10, no more than about 15, no more than about 20, no more than about 25, no more than about 30, no more than about 35, no more than about 40, no more than about 45, no more than about 50, or no more than about 100 such most influential or most important input variables among the plurality can yield decreased but still acceptable accuracy of classification (e.g., at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%). The subset may be selected by rank-ordering the entire plurality of input variables and selecting a predetermined number (e.g., no more than about 5, no more than about 10, no more than about 15, no more than about 20, no more than about 25, no more than about 30, no more than about 35, no more than about 40, no more than about 45, no more than about 50, or no more than about 100) of input variables with the best classification metrics.

Identifying or Monitoring a Sepsis-Related State

After using a trained algorithm to process the dataset, the sepsis-related state or non-sepsis-related state (e.g., SIRS) may be identified or monitored in the subject. The identification may be based at least in part on quantitative measures of sequence reads of the dataset at a panel of sepsis-related state-associated genomic loci (e.g., quantitative measures of RNA transcripts or DNA at the sepsis-related state-associated genomic loci), proteomic data comprising quantitative measures of proteins of the dataset at a panel of sepsis-related state-associated proteins, and/or metabolome data comprising quantitative measures of a panel of sepsis-related state-associated metabolites.

The sepsis-related state may be identified in the subject at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The accuracy of identifying the sepsis-related state by the trained algorithm may be calculated as the percentage of independent test samples (e.g., subjects known to have the sepsis-related state or subjects with negative clinical test results for the sepsis-related state) that are correctly identified or classified as having or not having the sepsis-related state.

The sepsis-related state may be identified in the subject with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the sepsis-related state using the trained algorithm may be calculated as the percentage of samples identified or classified as having the sepsis-related state that correspond to subjects that truly have the sepsis-related state.

The sepsis-related state may be identified in the subject with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the sepsis-related state using the trained algorithm may be calculated as the percentage of samples identified or classified as not having the sepsis-related state that correspond to subjects that truly do not have the sepsis-related state.

The sepsis-related state may be identified in the subject with a clinical sensitivity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the sepsis-related state using the trained algorithm may be calculated as the percentage of independent test samples associated with presence of the sepsis-related state (e.g., subjects known to have the sepsis-related state) that are correctly identified or classified as having the sepsis-related state.

The sepsis-related state may be identified in the subject with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the sepsis-related state using the trained algorithm may be calculated as the percentage of independent test samples associated with absence of the sepsis-related state (e.g., subjects with negative clinical test results for the sepsis-related state) that are correctly identified or classified as not having the sepsis-related state.

The SIRS-related state may be identified in the subject at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The accuracy of identifying the SIRS-related state by the trained algorithm may be calculated as the percentage of independent test samples (e.g., subjects known to have the SIRS-related state or subjects with negative clinical test results for the SIRS-related state) that are correctly identified or classified as having or not having the SIRS-related state.

The SIRS-related state may be identified in the subject with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the SIRS-related state using the trained algorithm may be calculated as the percentage of samples identified or classified as having the SIRS-related state that correspond to subjects that truly have the SIRS-related state.

The SIRS-related state may be identified in the subject with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the SIRS-related state using the trained algorithm may be calculated as the percentage of samples identified or classified as not having the SIRS-related state that correspond to subjects that truly do not have the SIRS-related state.

The SIRS-related state may be identified in the subject with a clinical sensitivity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the SIRS-related state using the trained algorithm may be calculated as the percentage of independent test samples associated with presence of the SIRS-related state (e.g., subjects known to have the SIRS-related state) that are correctly identified or classified as having the SIRS-related state.

The SIRS-related state may be identified in the subject with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the SIRS-related state using the trained algorithm may be calculated as the percentage of independent test samples associated with absence of the SIRS-related state (e.g., subjects with negative clinical test results for the SIRS-related state) that are correctly identified or classified as not having the SIRS-related state.

After the sepsis-related state is identified in a subject, a sub-type of the sepsis-related state (e.g., selected from among a plurality of sub-types of the sepsis-related state) may further be identified. The sub-type of the sepsis-related state may be determined based at least in part on the quantitative measures of sequence reads of the dataset at a panel of sepsis-related state-associated genomic loci (e.g., quantitative measures of RNA transcripts or DNA at the sepsis-related state-associated genomic loci), proteomic data comprising quantitative measures of proteins of the dataset at a panel of sepsis-related state-associated proteins, and/or metabolome data comprising quantitative measures of a panel of sepsis-related state-associated metabolites. For example, the subject may be identified as having a bacterial infection, a fungal infection, and/or a viral infection. After identifying the subject as being at risk of a bacterial infection, a fungal infection, and/or a viral infection, a clinical intervention for the subject may be selected based at least in part on the sub-type of bacterial infection, fungal infection, and/or viral infection for which the subject is identified as having. In some embodiments, the clinical intervention is selected from a plurality of clinical interventions (e.g., clinically indicated for different sub-types of infection).

In some embodiments, the trained algorithm may determine that the subject is at risk of bacterial infection of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

The trained algorithm may determine that the subject is at risk of bacterial infection at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more.

In some embodiments, the trained algorithm may determine that the subject is at risk of fungal infection of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

The trained algorithm may determine that the subject is at risk of fungal infection at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more.

In some embodiments, the trained algorithm may determine that the subject is at risk of viral infection of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

The trained algorithm may determine that the subject is at risk of viral infection at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more.

Upon identifying the subject as having the sepsis-related state, the subject may be optionally provided with a therapeutic intervention (e.g., prescribing an appropriate course of treatment to treat the sepsis-related state of the subject). The therapeutic intervention may comprise a prescription of an effective dose of a drug, a further testing or evaluation of the sepsis-related state, a further monitoring of the sepsis-related state, or a combination thereof. If the subject is currently being treated for the sepsis-related state with a course of treatment, the therapeutic intervention may comprise a subsequent different course of treatment (e.g., to increase treatment efficacy due to non-efficacy of the current course of treatment).

The therapeutic intervention may comprise recommending the subject for a secondary clinical test to confirm a diagnosis of the sepsis-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

The quantitative measures of sequence reads of the dataset at the panel of sepsis-related state-associated genomic loci (e.g., quantitative measures of RNA transcripts or DNA at the sepsis-related state-associated genomic loci), proteomic data comprising quantitative measures of proteins of the dataset at a panel of sepsis-related state-associated proteins, and/or metabolome data comprising quantitative measures of a panel of sepsis-related state-associated metabolites may be assessed over a duration of time to monitor a patient (e.g., subject who has sepsis-related state or who is being treated for sepsis-related state). In such cases, the quantitative measures of the dataset of the patient may change during the course of treatment. For example, the quantitative measures of the dataset of a patient with decreasing risk of the sepsis-related state due to an effective treatment may shift toward the profile or distribution of a healthy subject (e.g., a subject without a sepsis-related complication). Conversely, for example, the quantitative measures of the dataset of a patient with increasing risk of the sepsis-related state due to an ineffective treatment may shift toward the profile or distribution of a subject with higher risk of the sepsis-related state or a more advanced sepsis-related state.

The sepsis-related state of the subject may be monitored by monitoring a course of treatment for treating the sepsis-related state of the subject. The monitoring may comprise assessing the sepsis-related state of the subject at two or more time points. The assessing may be based at least on the quantitative measures of sequence reads of the dataset at a panel of sepsis-related state-associated genomic loci (e.g., quantitative measures of RNA transcripts or DNA at the sepsis-related state-associated genomic loci), proteomic data comprising quantitative measures of proteins of the dataset at a panel of sepsis-related state-associated proteins, and/or metabolome data comprising quantitative measures of a panel of sepsis-related state-associated metabolites determined at each of the two or more time points.

In some embodiments, a difference in the quantitative measures of sequence reads of the dataset at a panel of sepsis-related state-associated genomic loci (e.g., quantitative measures of RNA transcripts or DNA at the sepsis-related state-associated genomic loci), proteomic data comprising quantitative measures of proteins of the dataset at a panel of sepsis-related state-associated proteins, and/or metabolome data comprising quantitative measures of a panel of sepsis-related state-associated metabolites determined between the two or more time points may be indicative of one or more clinical indications, such as (i) a diagnosis of the sepsis-related state of the subject, (ii) a prognosis of the sepsis-related state of the subject, (iii) an increased risk of the sepsis-related state of the subject, (iv) a decreased risk of the sepsis-related state of the subject, (v) an efficacy of the course of treatment for treating the sepsis-related state of the subject, and (vi) a non-efficacy of the course of treatment for treating the sepsis-related state of the subject.

In some embodiments, a difference in the quantitative measures of sequence reads of the dataset at a panel of sepsis-related state-associated genomic loci (e.g., quantitative measures of RNA transcripts or DNA at the sepsis-related state-associated genomic loci), proteomic data comprising quantitative measures of proteins of the dataset at a panel of sepsis-related state-associated proteins, and/or metabolome data comprising quantitative measures of a panel of sepsis-related state-associated metabolites determined between the two or more time points may be indicative of a diagnosis of the sepsis-related state of the subject. For example, if the sepsis-related state was not detected in the subject at an earlier time point but was detected in the subject at a later time point, then the difference is indicative of a diagnosis of the sepsis-related state of the subject. A clinical action or decision may be made based on this indication of diagnosis of the sepsis-related state of the subject, such as, for example, prescribing a new therapeutic intervention for the subject. The clinical action or decision may comprise recommending the subject for a secondary clinical test to confirm the diagnosis of the sepsis-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the quantitative measures of sequence reads of the dataset at a panel of sepsis-related state-associated genomic loci (e.g., quantitative measures of RNA transcripts or DNA at the sepsis-related state-associated genomic loci), proteomic data comprising quantitative measures of proteins of the dataset at a panel of sepsis-related state-associated proteins, and/or metabolome data comprising quantitative measures of a panel of sepsis-related state-associated metabolites determined between the two or more time points may be indicative of a prognosis of the sepsis-related state of the subject.

In some embodiments, a difference in the quantitative measures of sequence reads of the dataset at a panel of sepsis-related state-associated genomic loci (e.g., quantitative measures of RNA transcripts or DNA at the sepsis-related state-associated genomic loci), proteomic data comprising quantitative measures of proteins of the dataset at a panel of sepsis-related state-associated proteins, and/or metabolome data comprising quantitative measures of a panel of sepsis-related state-associated metabolites determined between the two or more time points may be indicative of the subject having an increased risk of the sepsis-related state. For example, if the sepsis-related state was detected in the subject both at an earlier time point and at a later time point, and if the difference is a negative difference (e.g., the quantitative measures of sequence reads of the dataset at a panel of sepsis-related state-associated genomic loci (e.g., quantitative measures of RNA transcripts or DNA at the sepsis-related state-associated genomic loci), proteomic data comprising quantitative measures of proteins of the dataset at a panel of sepsis-related state-associated proteins, and/or metabolome data comprising quantitative measures of a panel of sepsis-related state-associated metabolites increased from the earlier time point to the later time point), then the difference may be indicative of the subject having an increased risk of the sepsis-related state. A clinical action or decision may be made based on this indication of the increased risk of the sepsis-related state, e.g., prescribing a new therapeutic intervention or switching therapeutic interventions (e.g., ending a current treatment and prescribing a new treatment) for the subject. The clinical action or decision may comprise recommending the subject for a secondary clinical test to confirm the increased risk of the sepsis-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the quantitative measures of sequence reads of the dataset at a panel of sepsis-related state-associated genomic loci (e.g., quantitative measures of RNA transcripts or DNA at the sepsis-related state-associated genomic loci), proteomic data comprising quantitative measures of proteins of the dataset at a panel of sepsis-related state-associated proteins, and/or metabolome data comprising quantitative measures of a panel of sepsis-related state-associated metabolites determined between the two or more time points may be indicative of the subject having a decreased risk of the sepsis-related state. For example, if the sepsis-related state was detected in the subject both at an earlier time point and at a later time point, and if the difference is a positive difference (e.g., the quantitative measures of sequence reads of the dataset at a panel of sepsis-related state-associated genomic loci (e.g., quantitative measures of RNA transcripts or DNA at the sepsis-related state-associated genomic loci), proteomic data comprising quantitative measures of proteins of the dataset at a panel of sepsis-related state-associated proteins, and/or metabolome data comprising quantitative measures of a panel of sepsis-related state-associated metabolites decreased from the earlier time point to the later time point), then the difference may be indicative of the subject having a decreased risk of the sepsis-related state. A clinical action or decision may be made based on this indication of the decreased risk of the sepsis-related state (e.g., continuing or ending a current therapeutic intervention) for the subject. The clinical action or decision may comprise recommending the subject for a secondary clinical test to confirm the decreased risk of the sepsis-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scanor any combination thereof.

In some embodiments, a difference in the quantitative measures of sequence reads of the dataset at a panel of sepsis-related state-associated genomic loci (e.g., quantitative measures of RNA transcripts or DNA at the sepsis-related state-associated genomic loci), proteomic data comprising quantitative measures of proteins of the dataset at a panel of sepsis-related state-associated proteins, and/or metabolome data comprising quantitative measures of a panel of sepsis-related state-associated metabolites determined between the two or more time points may be indicative of an efficacy of the course of treatment for treating the sepsis-related state of the subject. For example, if the sepsis-related state was detected in the subject at an earlier time point but was not detected in the subject at a later time point, then the difference may be indicative of an efficacy of the course of treatment for treating the sepsis-related state of the subject. A clinical action or decision may be made based on this indication of the efficacy of the course of treatment for treating the sepsis-related state of the subject, e.g., continuing or ending a current therapeutic intervention for the subject. The clinical action or decision may comprise recommending the subject for a secondary clinical test to confirm the efficacy of the course of treatment for treating the sepsis-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the quantitative measures of sequence reads of the dataset at a panel of sepsis-related state-associated genomic loci (e.g., quantitative measures of RNA transcripts or DNA at the sepsis-related state-associated genomic loci), proteomic data comprising quantitative measures of proteins of the dataset at a panel of sepsis-related state-associated proteins, and/or metabolome data comprising quantitative measures of a panel of sepsis-related state-associated metabolites determined between the two or more time points may be indicative of a non-efficacy of the course of treatment for treating the sepsis-related state of the subject. For example, if the sepsis-related state was detected in the subject both at an earlier time point and at a later time point, and if the difference is a negative or zero difference (e.g., the quantitative measures of sequence reads of the dataset at a panel of sepsis-related state-associated genomic loci (e.g., quantitative measures of RNA transcripts or DNA at the sepsis-related state-associated genomic loci), proteomic data comprising quantitative measures of proteins of the dataset at a panel of sepsis-related state-associated proteins, and/or metabolome data comprising quantitative measures of a panel of sepsis-related state-associated metabolites increased or remained at a constant level from the earlier time point to the later time point), and if an efficacious treatment was indicated at an earlier time point, then the difference may be indicative of a non-efficacy of the course of treatment for treating the sepsis-related state of the subject. A clinical action or decision may be made based on this indication of the non-efficacy of the course of treatment for treating the sepsis-related state of the subject, e.g., ending a current therapeutic intervention and/or switching to (e.g., prescribing) a different new therapeutic intervention for the subject. The clinical action or decision may comprise recommending the subject for a secondary clinical test to confirm the non-efficacy of the course of treatment for treating the sepsis-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, for example, the clinical health data comprises one or more quantitative measures of the subject. Non-limiting examples of clinical health data can comprise age, weight, height, body mass index (BMI), blood pressure, heart rate, and glucose levels. As another example, the clinical health data can comprise one or more categorical measures, such as race, ethnicity, history of medication or other clinical treatment, history of tobacco use, history of alcohol consumption, daily activity or fitness level, genetic test results, blood test results, and imaging results.

Outputting a Report of the Sepsis-Related State

After the sepsis-related state or non-sepsis-related state is identified or an increased risk of the sepsis-related state or non-sepsis-related state is monitored in the subject, a report may be electronically outputted that is indicative of (e.g., identifies or provides an indication of) the sepsis-related state or non-sepsis-related state of the subject. The subject may not display a sepsis-related state (e.g., is asymptomatic of the sepsis-related state such as a sepsis-related complication). The report may be presented on a graphical user interface (GUI) of an electronic device of a user. The user may be the subject, a caretaker, a physician, a nurse, or another health care worker.

The report may include one or more clinical indications such as (i) a diagnosis of the sepsis-related state or non-sepsis-related state of the subject, (ii) a prognosis of the sepsis-related state or non-sepsis-related state of the subject, (iii) an increased risk of the sepsis-related state or non-sepsis-related state of the subject, (iv) a decreased risk of the sepsis-related state or non-sepsis-related state of the subject, (v) an efficacy of the course of treatment for treating the sepsis-related state or non-sepsis-related state of the subject, and (vi) a non-efficacy of the course of treatment for treating the sepsis-related state or non-sepsis-related state of the subject. The report may include one or more clinical actions or decisions made based on these one or more clinical indications. Such clinical actions or decisions may be directed to therapeutic interventions, induction or inhibition of labor, or further clinical assessment or testing of the sepsis-related state or non-sepsis-related state of the subject.

For example, a clinical indication of a diagnosis of the sepsis-related state or non-sepsis-related state (e.g., SIRS) of the subject may be accompanied with a clinical action of prescribing a new therapeutic intervention for the subject. As another example, a clinical indication of an increased risk of the sepsis-related state of the subject may be accompanied with a clinical action of prescribing a new therapeutic intervention or switching therapeutic interventions (e.g., ending a current treatment and prescribing a new treatment) for the subject. As another example, a clinical indication of a decreased risk of the sepsis-related state or non-sepsis-related state of the subject may be accompanied with a clinical action of continuing or ending a current therapeutic intervention for the subject. As another example, a clinical indication of an efficacy of the course of treatment for treating the sepsis-related state of the subject or non-sepsis-related state of the subject may be accompanied with a clinical action of continuing or ending a current therapeutic intervention for the subject. As another example, a clinical indication of a non-efficacy of the course of treatment for treating the sepsis-related state or non-sepsis-related state of the subject may be accompanied with a clinical action of ending a current therapeutic intervention and/or switching to (e.g., prescribing) a different new therapeutic intervention for the subject.

Computer Systems

Figure 19:
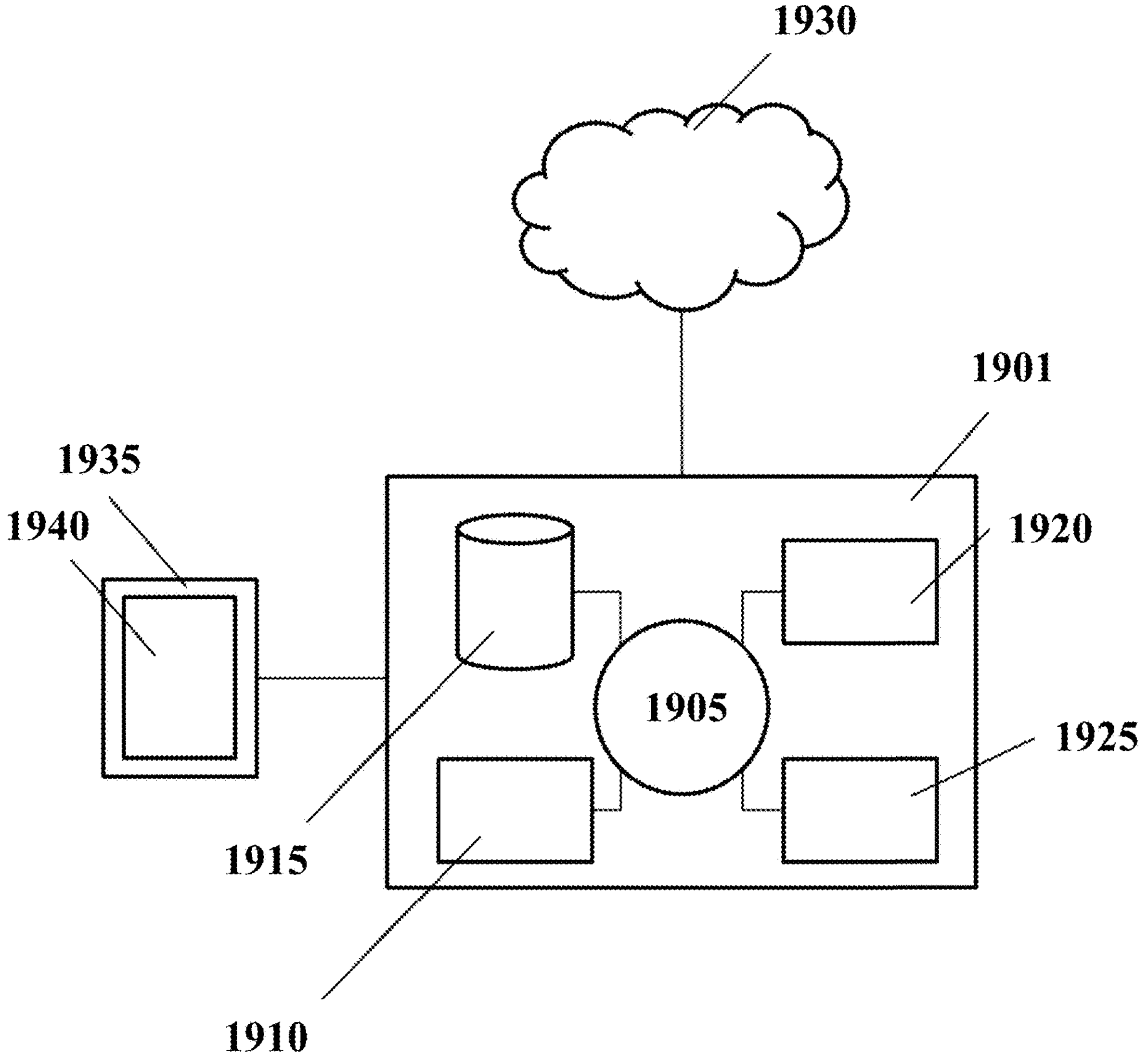
FIG. 19 illustrates a computer system that is programmed or otherwise configured to implement methods provided herein.

The present disclosure provides computer systems that are programmed to implement methods of the disclosure. FIG. 19 shows a computer system 1901 that is programmed or otherwise configured to, for example, (i) train and test a trained algorithm, (ii) use the trained algorithm to process data to determine a sepsis-related state or non-sepsis related state (e.g., SIRS) of a subject, (iii) determine a quantitative measure indicative of a sepsis-related state or non-sepsis related state (e.g., SIRS) of a subject, (iv) identify or monitor the sepsis-related state or non-sepsis related state (e.g., SIRS) of the subject, and (v) electronically output a report that indicative of the sepsis-related state or non-sepsis related state (e.g., SIRS) of the subject.

The computer system 1901 can regulate various aspects of analysis, calculation, and generation of the present disclosure, such as, for example, (i) training and testing a trained algorithm, (ii) using the trained algorithm to process data to determine a sepsis-related state of a subject, (iii) determining a quantitative measure indicative of a sepsis-related state of a subject, (iv) identifying or monitoring the sepsis-related state of the subject, and (v) electronically outputting a report that indicative of the sepsis-related state of the subject. The computer system 1901 can be an electronic device of a user or a computer system that is remotely located with respect to the electronic device. The electronic device can be a mobile electronic device.

The computer system 1901 includes a central processing unit (CPU, also "processor" and "computer processor" herein) 1905, which can be a single core or multi core processor, or a plurality of processors for parallel processing. The computer system 1901 also includes memory or memory location 1910 (e.g., random-access memory, read-only memory, flash memory), electronic storage unit 1915 (e.g., hard disk), communication interface 1920 (e.g., network adapter) for communicating with one or more other systems, and peripheral devices 1925, such as cache, other memory, data storage and/or electronic display adapters. The memory 1910, storage unit 1915, interface 1920 and peripheral devices 1925 are in communication with the CPU 1905 through a communication bus (solid lines), such as a motherboard. The storage unit 1915 can be a data storage unit (or data repository) for storing data. The computer system 1901 can be operatively coupled to a computer network ("network") 1930 with the aid of the communication interface 1920. The network 1930 can be the Internet, an internet and/or extranet, or an intranet and/or extranet that is in communication with the Internet.

The network 1930 in some cases is a telecommunication and/or data network. The network 1930 can include one or more computer servers, which can enable distributed computing, such as cloud computing. For example, one or more computer servers may enable cloud computing over the network 1930 ("the cloud") to perform various aspects of analysis, calculation, and generation of the present disclosure, such as, for example, (i) training and testing a trained algorithm, (ii) using the trained algorithm to process data to determine a sepsis-related state of a subject, (iii) determining a quantitative measure indicative of a sepsis-related state of a subject, (iv) identifying or monitoring the sepsis-related state of the subject, and (v) electronically outputting a report that indicative of the sepsis-related state of the subject. Such cloud computing may be provided by cloud computing platforms such as, for example, Amazon Web Services (AWS), Microsoft Azure, Google Cloud Platform, and IBM cloud. The network 1930, in some cases with the aid of the computer system 1901, can implement a peer-to-peer network, which may enable devices coupled to the computer system 1901 to behave as a client or a server.

The CPU 1905 may comprise one or more computer processors and/or one or more graphics processing units (GPUs). The CPU 1905 can execute a sequence of machine-readable instructions, which can be embodied in a program or software. The instructions may be stored in a memory location, such as the memory 1910. The instructions can be directed to the CPU 1905, which can subsequently program or otherwise configure the CPU 1905 to implement methods of the present disclosure. Examples of operations performed by the CPU 1905 can include fetch, decode, execute, and writeback.

The CPU 1905 can be part of a circuit, such as an integrated circuit. One or more other components of the system 1901 can be included in the circuit. In some cases, the circuit is an application specific integrated circuit (ASIC).

The storage unit 1915 can store files, such as drivers, libraries and saved programs. The storage unit 1915 can store user data, e.g., user preferences and user programs. The computer system 1901 in some cases can include one or more additional data storage units that are external to the computer system 1901, such as located on a remote server that is in communication with the computer system 1901 through an intranet or the Internet.

The computer system 1901 can communicate with one or more remote computer systems through the network 1930. For instance, the computer system 1901 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1901 via the network 1930.

Methods as described herein can be implemented by way of machine (e.g., computer processor) executable code stored on an electronic storage location of the computer system 1901, such as, for example, on the memory 1910 or electronic storage unit 1915. The machine executable or machine readable code can be provided in the form of software. During use, the code can be executed by the processor 1905. In some cases, the code can be retrieved from the storage unit 1915 and stored on the memory 1910 for ready access by the processor 1905. In some situations, the electronic storage unit 1915 can be precluded, and machine-executable instructions are stored on memory 1910.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 1901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1901 can include or be in communication with an electronic display 1935 that comprises a user interface (UI) 1940 for providing, for example, (i) a visual display indicative of training and testing of a trained algorithm, (ii) a visual display of data indicative of a sepsis-related state of a subject, (iii) a quantitative measure of a sepsis-related state of a subject, (iv) an identification of a subject as having a sepsis-related state, or (v) an electronic report indicative of the sepsis-related state of the subject. Examples of Us include, without limitation, a graphical user interface (GUI) and web-based user interface.

Methods and systems of the present disclosure can be implemented by way of one or more algorithms. An algorithm can be implemented by way of software upon execution by the central processing unit 1905. The algorithm can, for example, (i) train and test a trained algorithm, (ii) use the trained algorithm to process data to determine a sepsis-related state of a subject, (iii) determine a quantitative measure indicative of a sepsis-related state of a subject, (iv) identify or monitor the sepsis-related state of the subject, and (v) electronically output a report that indicative of the sepsis-related state of the subject.

It is to be understood that the invention is not limited in its application to the details of construction and the arrangement of components set forth in the following description or illustrated in the following drawings. The invention is capable of other embodiments and of being practiced or of being carried out in various ways.

Having described various aspects of the inventive concept, the same will be explained in further detail in the following examples, which are included herein for illustrative purposes, and which are not intended to be limiting to the invention.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

Example 1: Infection Versus No Infection and Etiology of Infection

Signature Discovery, Validation, and Testing

For each classification/prediction task, the model can be sequentially trained, validated and then tested on subsets of the data. Training allows for variable (e.g., gene) selection and parameter (e.g., weight) estimation for the classification model. The fitted model from training can be used to predict class in the validation dataset. Validation provides an unbiased estimate of candidate model performance. Finally, the test dataset can be used to provide an unbiased evaluation of the final model that was fit on the training data. The test data can be used to estimate classification model performance (e.g., sensitivity and specificity).

Sixty-four gene targets were selected using the signature discovery model and were included in the classification model (Table 1 and FIG. 2). The HUGO gene names in Table 1 and FIG. 2 are representative of the RNA transcripts of the gene targets identified during signature discovery. These gene targets are shown in rank order by weight based on an aggregate of each gene's importance for identifying the presence or absence of infection and the cause of infection. As shown in FIG. 1, the ability of a gene target to discriminate infection from non-infection and the ability to identify the pathogen class responsible for infection were given equal importance.

The signature thus includes a plurality of genes for use in the diagnosis of infection or no infection in a subject who is suspected to have this condition and for determining the pathogen class of the infection. Each biomarker includes at least one gene target that may be used during development of a test for implementation on a specific testing platform. Thus, the signature includes a plurality of gene targets for use in the diagnosis of a condition in a subject who is suspected to have an infection and for determining the pathogen class of the infectious agent. Each diagnostic task can be comprised of at least one gene target in the host response signature. For this endeavor, a gene target can be an mRNA.

FIG. 2 illustrates the 64 genes in the sparse model arising from the discovery process, where importance in the model is indicated by the weights associated with each individual gene in the discovery model (x-axis). The genes are listed in the figure according to the weight determined during training, sorted from largest (most highly weighted) to smallest (least highly weighted). The weight for each gene is assumed to indicate the importance of the particular gene in correctly predicting the presence or absence of infection as well as the microbiological etiology of infection.

Evaluation of the Signatures

The performance and stability of the resulting model was evaluated with five rounds of five-fold cross validation, with the data used as follows (the same datasets described in data Sources, but are further divided into how the individual datasets and samples were used for modeling (e.g., training, validation and testing)):

Data Sources

GEO—194 Studies, 7476 Samples

ArrayExpress—12 Studies, 520 Samples

Train/Validation/Test

Number of Studies used to Train, Validate, and Test the model

Train: 150

Validation: 28

Test: 28

Number of Samples used to Train, Validate, and Test the model

Train: 5112

Validate: 1421

Test: 1463

Number of infection versus non-infection (e.g. a binary phenotype) samples used to Train, Validate, and Test the model Train (3546 Infection, 1566 Non-infection)

Validation (713 Infection, 708 Non-infection)

Test (706 Infection, 757 Non-infection)

Number of samples with each phenotype used to Train, Validate, and Test the model (it can be noted that the class label, no infection, includes healthy and non-infectious illness)

Healthy (1288, 555, 361)

Non-infectious illness, including SIRS (278, 153, 396)

Viral (1649, 388, 442)

Bacterial (562, 130, 173)

Fungal (24, 41, 8)

Infection (1311, 154, 83)

Number of samples from each Biological Source used to Train, Validate, and Test the model in vivo (4401, 1092, 1319)

ex vivo (344, 302, 107)

in vitro (367, 27, 37)

Figure 3:
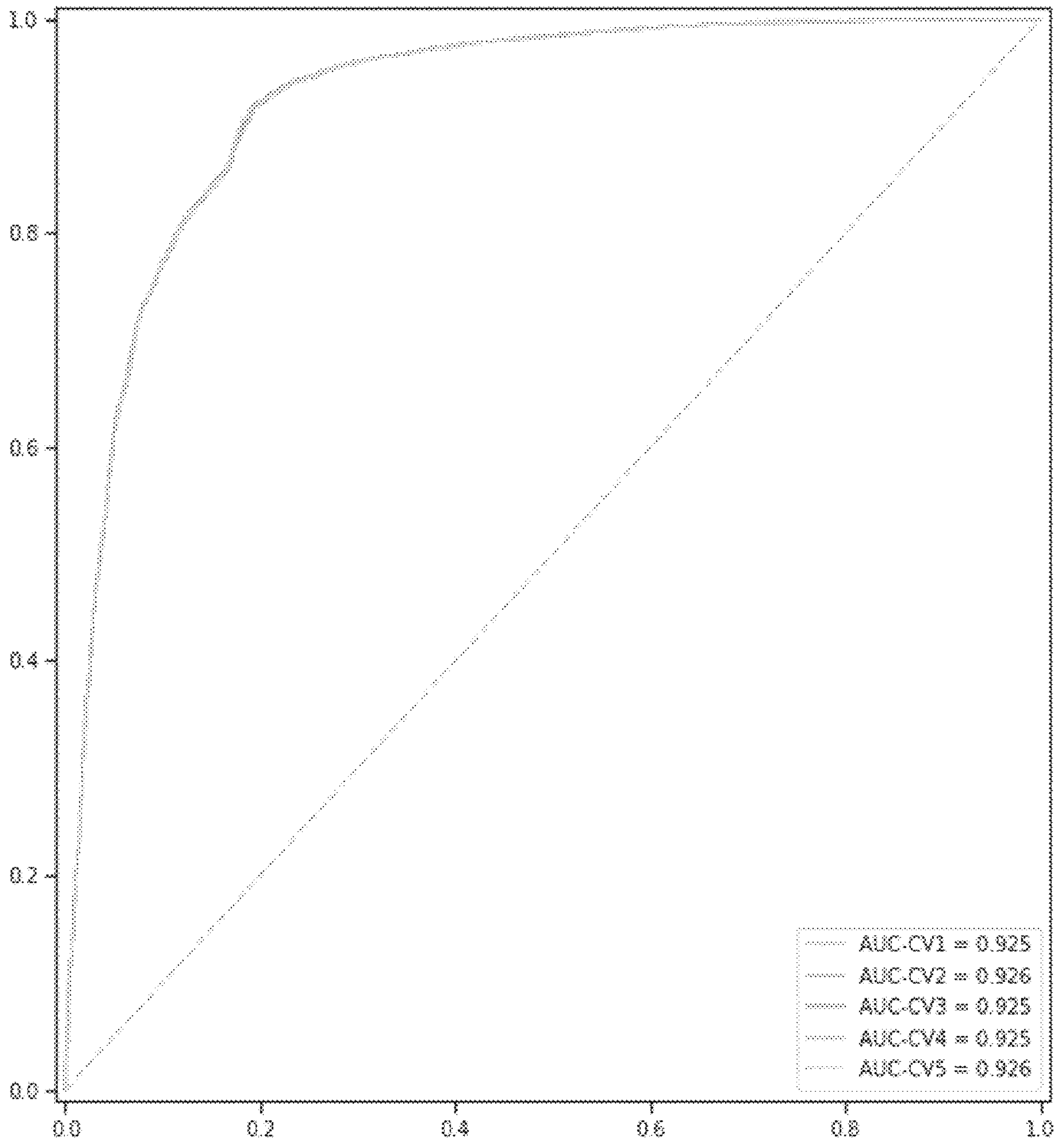
FIG. 3 depicts the ROC curves from 5 distinct rounds of 5-fold cross validation. All rounds achieve an AUC of 0.925 or 0.926 demonstrating stability of the model across different data splits. This data, and the confusion matrix in FIG. 4, use all top-performing genes.
Figure 4:
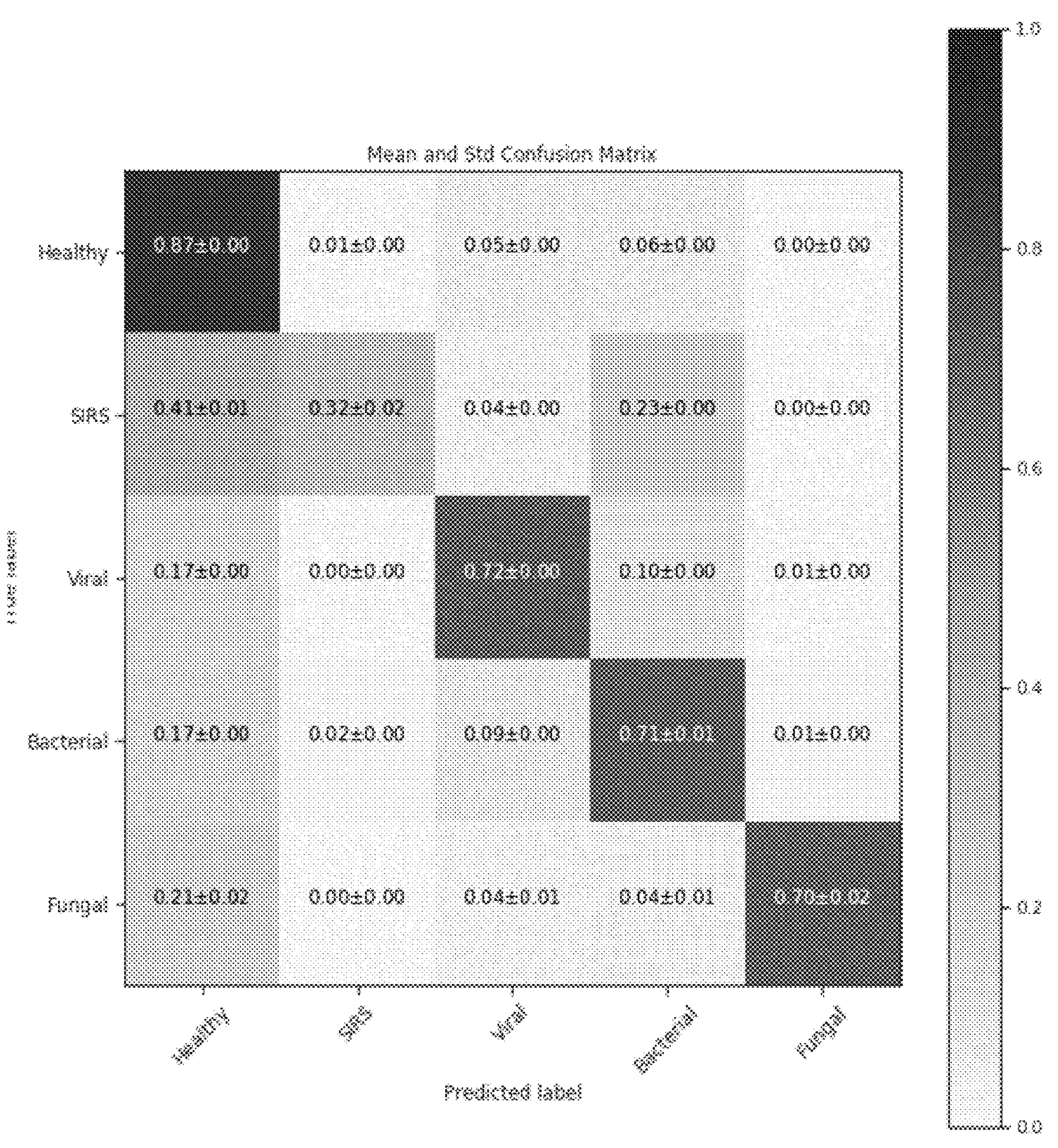
FIG. 4 depicts a confusion matrix providing class labels for all five phenotype classes (healthy, SIRS, bacterial, fungal, and viral) simultaneously using the 64 top-performing genes.

The ROC curves from 5 distinct rounds of 5-fold cross validation are shown in FIG. 3. All rounds achieve an AUC of 0.925 or 0.926 demonstrating stability of the model across difference data splits. This data, and the confusion matrix in FIG. 4, use all genes (specifically, the top performing approximately 100-200 genes). The confusion matrix shown in FIG. 4 provides class for all five phenotype classes (healthy, non-infectious illness (including SIRS), bacterial, fungal, viral) simultaneously.

Infection Signature Evaluation Continued

Figure 5:
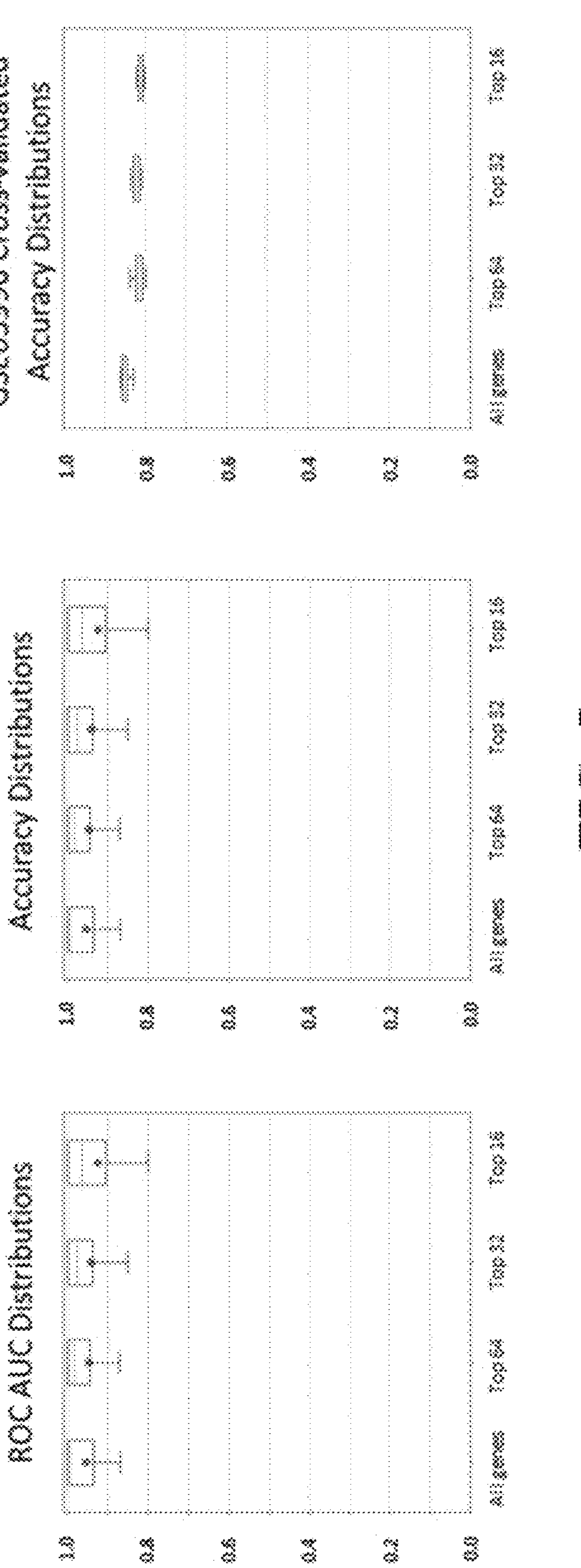
FIG. 5 depicts the distribution of classification accuracy for the infection versus no infection task for the 4 gene sets (all genes, top 64 genes, top 32 genes, top 16 genes) based on ROC AUC distributions, accuracy distributions, and highlights accuracy distribution performance in one particular dataset (GSE63990).

Gene signature subsets (e.g., all genes, top 64, top 32, top 16) were also evaluated by fitting the logistic regression classification models to each study (e.g., each dataset) individually rather than across all datasets. This was done to remove the effects of non-biological variation between studies, and to test the descriptive ability of the selected genes. This allows us to see the ability of the model to classify subjects (samples) once technical variability (e.g., non-biological study variance) is removed. Mean AUC and accuracy are shown for infection vs. no infection across all studies (FIG. 5). Within each graph, the performances are shown for classifiers incorporating all genes (number estimated to be 100-200 genes), top 64, top 32, and top 16 genes. In addition, the accuracy distribution for cross-validation is shown for a single study, GSE63990, as an example. Removing the non-biological source of variation (e.g., due to technical differences in the generation of data for each study) improves the classification performance.

Figure 6:
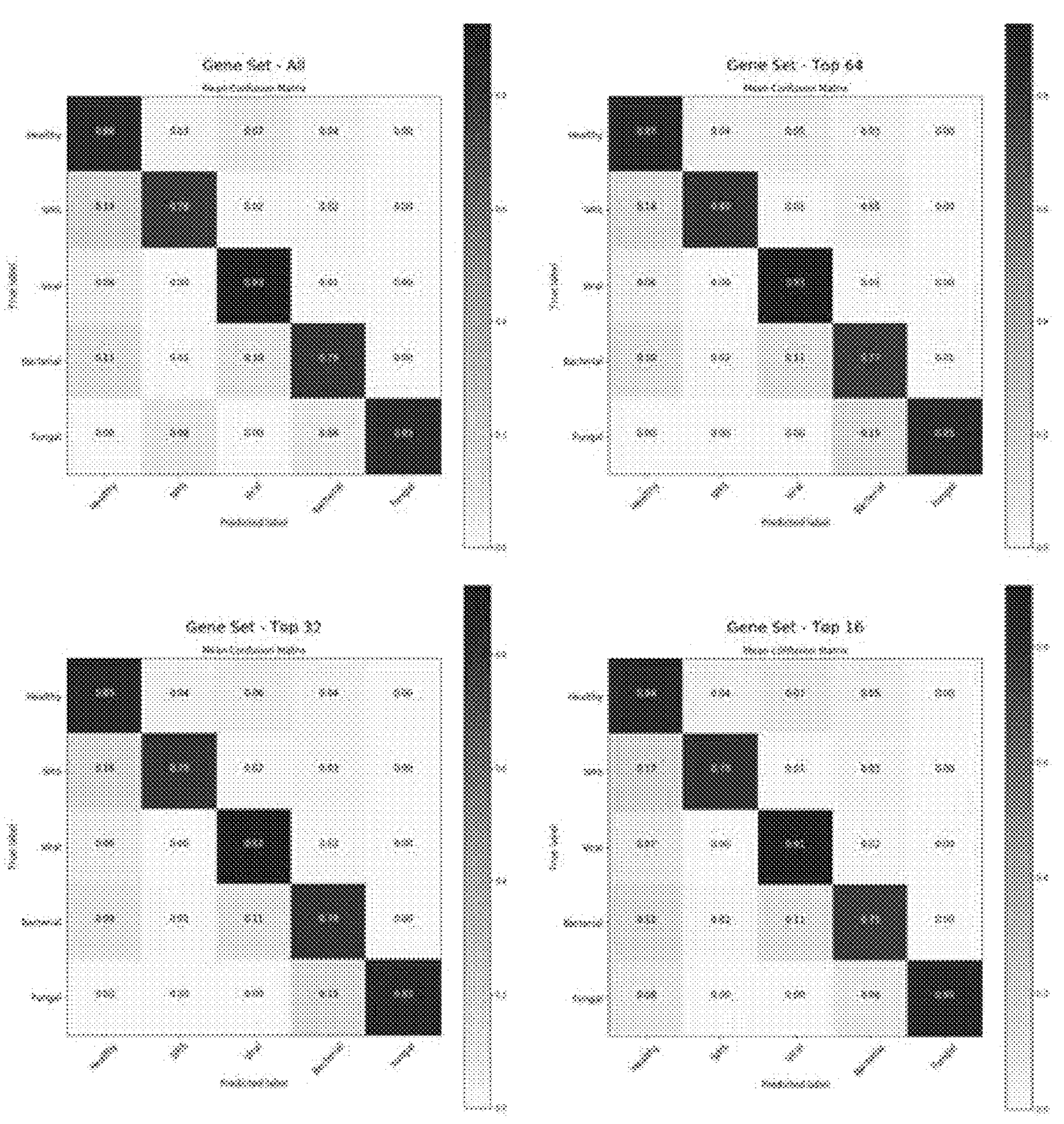
FIG. 6 depicts confusion matrices for the 4 gene sets (all genes, top 64 genes, top 32 genes, and top 16 genes) following infection signature evaluation.

FIG. 6 shows the accuracy for each phenotype class (infection, healthy, non-infectious illness including SIRS, bacterial, fungal, viral) in the multi-phenotype analysis when the logistic regression models were trained individually on each study to remove the influence on non-biological variance across studies. For each study, the four gene sets were evaluated. In the figures, SIRS indicates non-infectious illness including SIRS.

The rows are normalized and sum to 1 so for each "True" label on the y-axis to show how often a sample drawn from one of the multi-phenotype classes is correctly classified or misclassified into another bin. This demonstrates that removing the non-biological sources of variation improves classification and that classification remains stable as the size of the gene signature is reduced from all genes to 16 genes. This is an important finding since many assay platforms are limited with respect to the number of genes that may be analyzed.

Figure 7:
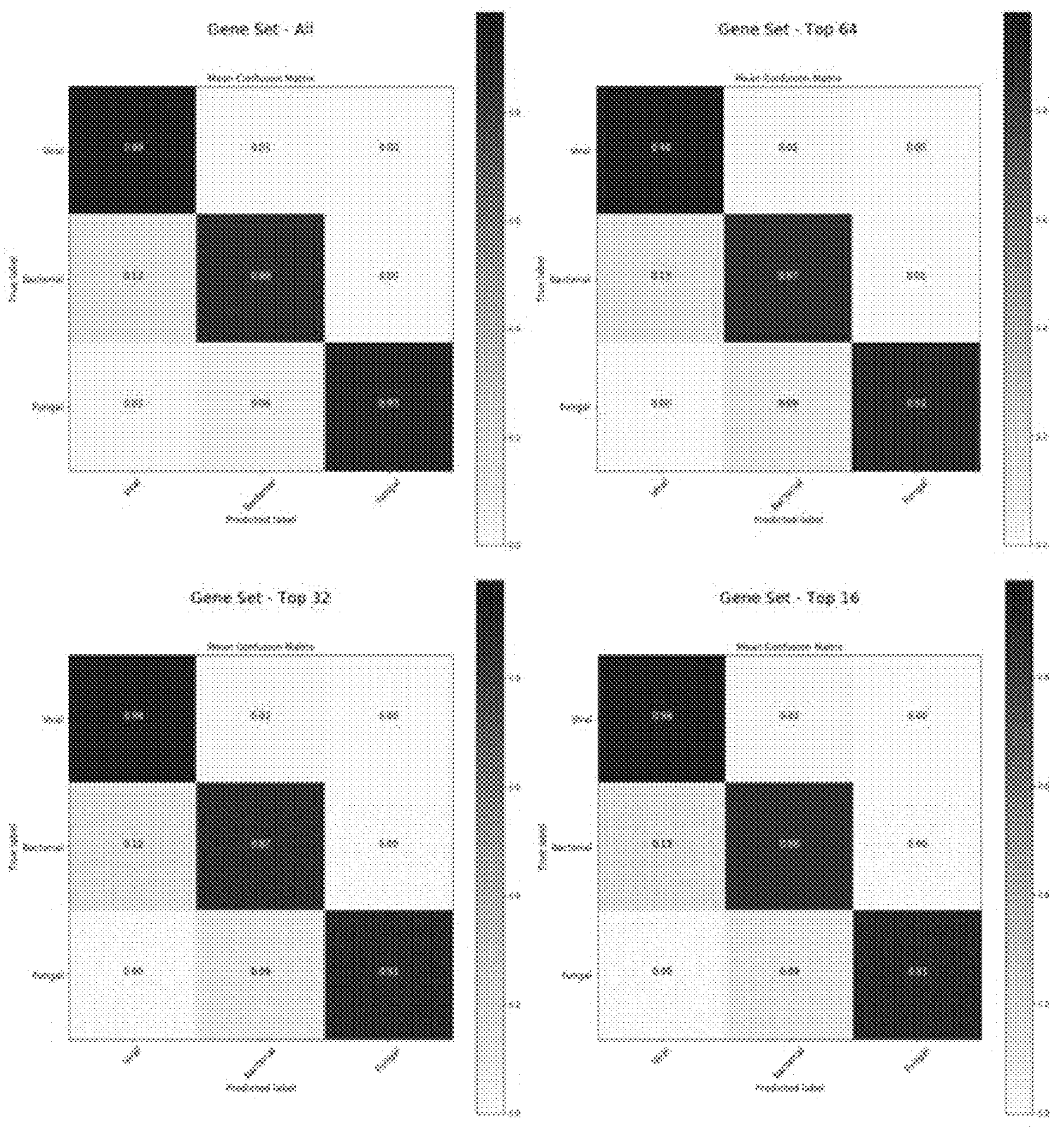
FIG. 7 depicts confusion matrices for the 4 gene sets given an infected sample. This demonstrates that if we are certain that the sample is infected then we can differentiate between the three infection classes more easily than when the model must first decide if a sample is infected and then determine the infection source as shown in FIG. 6.

FIG. 7 depicts confusion matrices for four gene sets given an infected sample. In these confusion matrices, only samples that are labeled as belonging to an infection class (bacterial, fungal, or viral) are considered. This demonstrates that, if the sample is known to be infected, the three infection classes may be differentiated more easily than when the model must first decide if a sample is infected and then determine the pathogen class causing the infection.

This scenario more closely resembles a use case where there is a high degree of certainty that a patient is suffering from an infection, but the source of the infection may be unknown and is to be ascertained.

These confusion matrices show that classification accuracy is not greatly decreased as one moves from the largest (64 gene) to the smallest (16 gene) models. It may be recognized by one skilled in the art that 64, 32 and 16 gene signatures are examples and in practice the informative gene signatures may be any number of genes less than 64, including less than 16 genes. The size of the gene list will be determined during model training, as described elsewhere.

SUMMARY

A classification model including, for example, a set of 64, 32 or 16 genes, or any subset thereof, can discriminate between infection and non-infection even with a diverse array of pathogens causing infection. The model is stable, and classification is not greatly diminished as the size of the gene signature is reduced to 16 or fewer genes, or any subset thereof. In addition, removing the non-biological source of variation—meaning variation not due to the specific treatment or condition in each study—improves classification. Anyone skilled in the art will recognize that in a test translated to a technology platform, removal of non-biological variation may occur through a process of normalization. Given the large number and diversity of studies included, non-biological sources of variation are very high.

Example 2: Evaluating the Infection Signature for Identification of Sepsis

Data Used 71 studies/datasets from GEO and ArrayExpress were selected specifically for evaluating sepsis classification. These studies were selected because they included patients with sepsis and/or critical illness by virtue of ICU admission. "Infection" as a phenotype includes those with and without critical illness. "Sepsis" as a phenotype includes those with infection and critical illness.

Only 40 of the 71 studies were deemed to be acceptable for use in evaluation of sepsis because 20 studies were missing processed data in the repositories and 11 studies had only a single binary class and were excluded.

In this analysis, only data from 'in vivo' samples were used (e.g., data from ex vivo or in vitro samples were excluded).

Signature Evaluation Method

To evaluate the model for identification of sepsis, cross-validated logistic regression models were trained separately on each study. Training the models on each study individually removes the influence of non-biological variance across studies. The Top 16, 32, or 64 genes in the signature were used for training and testing in three separate tests of sepsis versus not sepsis.

The first test defined the sepsis class as infection due to bacterial, fungal, or viral pathogens and the class that was negative for sepsis was composed of data from the healthy and non-infectious, including SIRS, samples.

The second test included only infection due to bacterial sepsis and the negative (no sepsis) class was composed of data from the combined healthy and non-infectious samples.

As with the second test, the third test used data from bacterial infection samples only in the sepsis class, but the infection-negative class was composed of non-infectious, including SIRS, samples only (e.g., samples from healthy were omitted in the comparator group).

Test 1: Sepsis (bacterial, fungal, viral)

Negative class (e.g., negative for sepsis, included healthy, SIRS)

1370 samples

Positive class (e.g., positive for sepsis, included bacterial, fungal, viral)

2320 samples

Test 2: Sepsis (bacterial only)

Negative class (healthy, SIRS)

1278 samples

Positive class (bacterial):

1565 samples

Test 3: Sepsis (bacterial only) vs non-infectious illness, including SIRS (henceforth noted as 'SIRS')

Negative class (SIRS)

544 samples

Positive class (bacterial)

653 samples

Signature Evaluation for Each Test

The performance and stability of the resulting classification models, using the Top 16, 32 or 64 gene targets from discovery (Table 1), were evaluated with five rounds of five-fold cross validation such that 5 receiver operating curves were generated for each of the three tests described above, and the sensitivity and specificity of the model for each test was determined. The data for the Top 64, 32 and 16 genes are given, with the data for the Top 16 illustrated for each Test scenario.

Test 1 results for evaluation of the model for classification of Positive for sepsis due to Bacterial, Viral, or Fungal infection versus Negative for sepsis (Healthy and SIRS samples).

Figure 8:
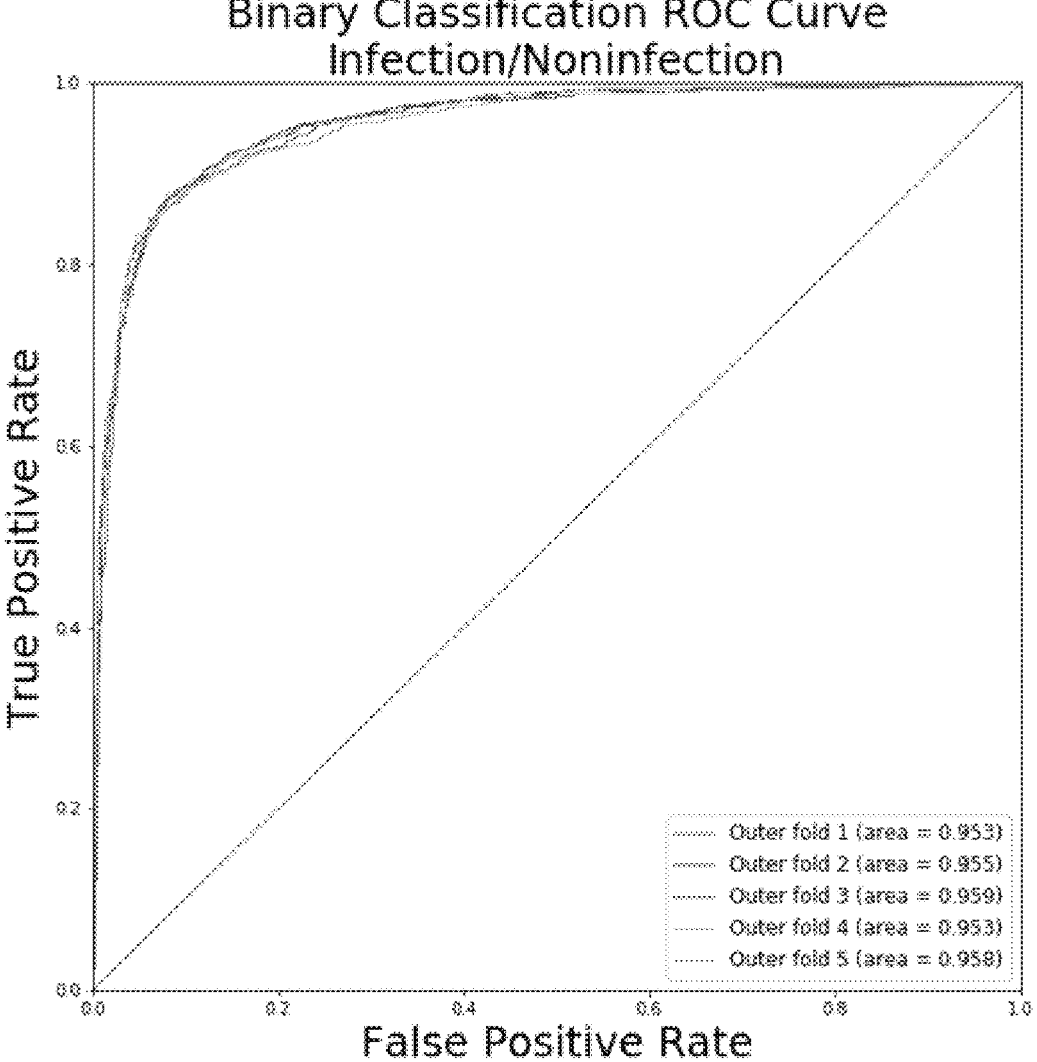
FIG. 8 depicts five-fold cross validation results for the 16 gene model for classification of sepsis due to bacterial, viral, or fungal infection versus negative for sepsis (healthy and SIRS samples) (Test 1).
Figure 9:
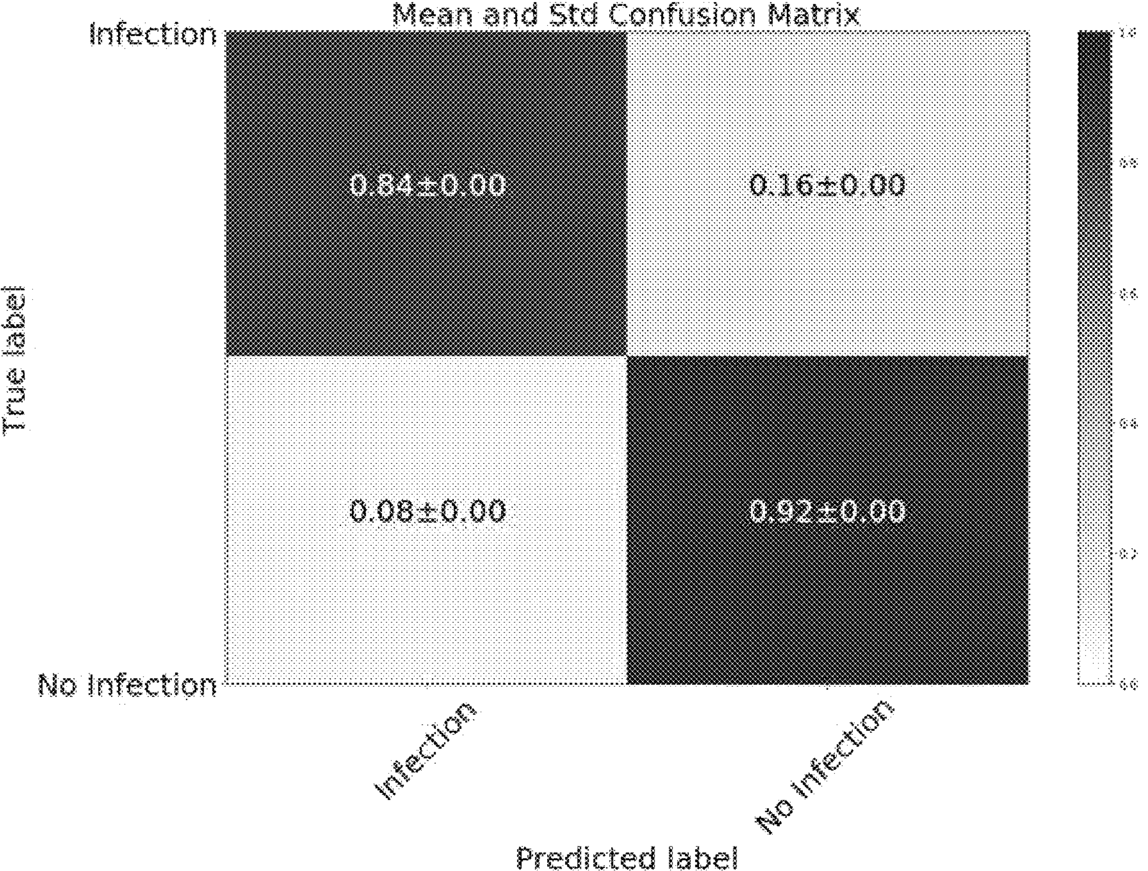
FIG. 9 depicts the confusion matrix for the 16 gene model in Test 1, sepsis (bacteria, virus, and fungus) versus no sepsis (healthy and SIRS).

Five rounds of cross validation generated 5 values for area under the receiver operating characteristic curves (AUROC) for each of the models (Top 64, 32, and 16 genes). The ranges of the five AUROC values are given for each model (Table 3) and the ROC curves for the Top 16 gene model is shown in FIG. 8. The accompanying confusion matrix (FIG. 9) demonstrates that the 16 gene model achieved 84% sensitivity and 92% specificity for determining sepsis due to bacterial, viral, or fungal infection versus no sepsis (healthy plus SIRS states) (FIG. 9). The sensitivity and specificity for the other models is summarized in Table 3.

TABLE 3

| # Genes in Model | AUROC Range | Sensitivity (%) | Specificity (%) |
|---|---|---|---|
| 16 | 0.953-0.959 | 84 ± 0.00 | 92 ± 0.00 |
| 32 | 0.963-0.968 | 88 ± 0.01 | 94 ± 0.00 |
| 64 | 0.965-0.972 | 89 ± 0.01 | 94 ± 0.00 |

Test 2 results for evaluation of the model for classification of Positive for sepsis due to Bacterial infection versus Negative for sepsis (Healthy and SIRS samples).

Figure 10:
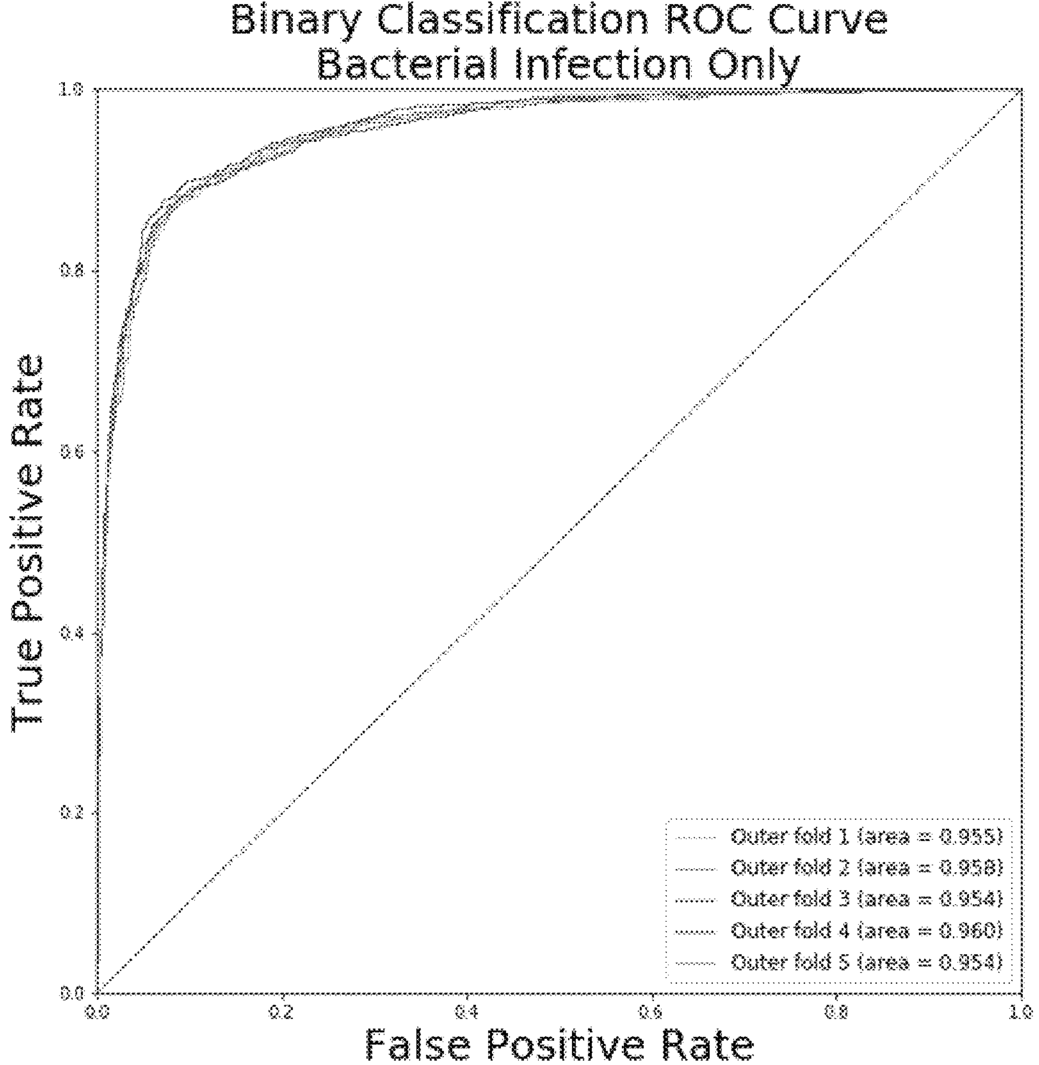
FIG. 10 depicts the five-fold cross validation results for the 16-gene model for classification of positive for sepsis due to bacterial infection versus negative for sepsis (healthy and SIRS samples) (Test 2).
Figure 11:
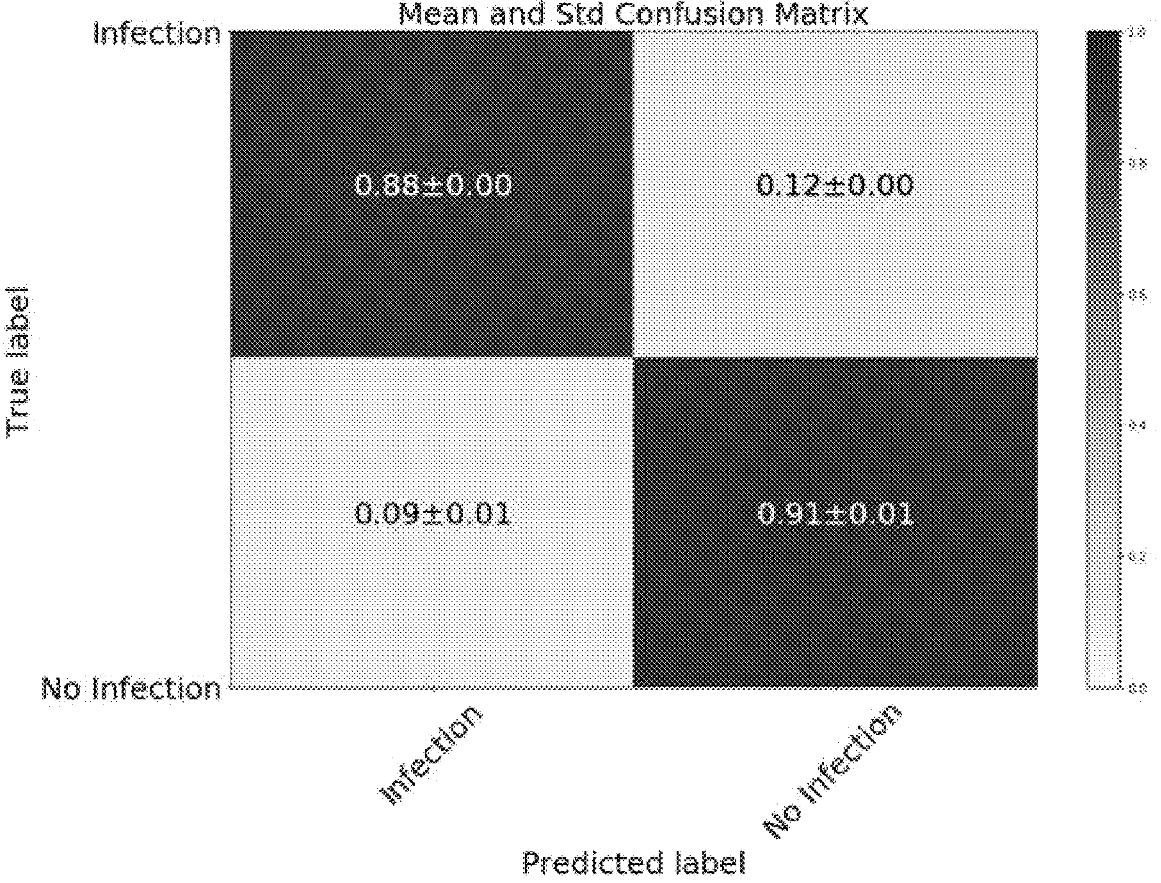
FIG. 11 depicts the confusion matrix for Test 2, sepsis (bacteria) versus no sepsis (healthy and SIRS) using the 16-gene model.

Five rounds of cross validation generated 5 values for area under the receiver operating characteristic curves (AUROC) for each of the models (Top 64, 32, and 16 genes). The ranges of the five AUROC values are given for each model (Table 4) and the data for the Top 16 genes is shown in FIG. 10. The accompanying confusion matrix (FIG. 11) demonstrates that the 16 gene model achieves 88% sensitivity and 91% specificity for determining sepsis due to bacterial infection versus no sepsis (healthy plus SIRS states). The sensitivity and specificity for the other models is summarized in Table 4.

TABLE 4

| # Genes in Model | AUROC Range | Sensitivity (%) | Specificity (%) |
|---|---|---|---|
| 16 | 0.954-0.960 | 88 ± 0.00 | 91 ± 0.01 |
| 32 | 0.964-0.967 | 90 ± 0.00 | 92 ± 0.00 |
| 64 | 0.963-0.972 | 90 ± 0.01 | 93 ± 0.00 |

Test 3 results for evaluation of the model for classification of Positive for sepsis due to Bacterial infection versus Negative for sepsis (SIRS samples only).

Figure 12:
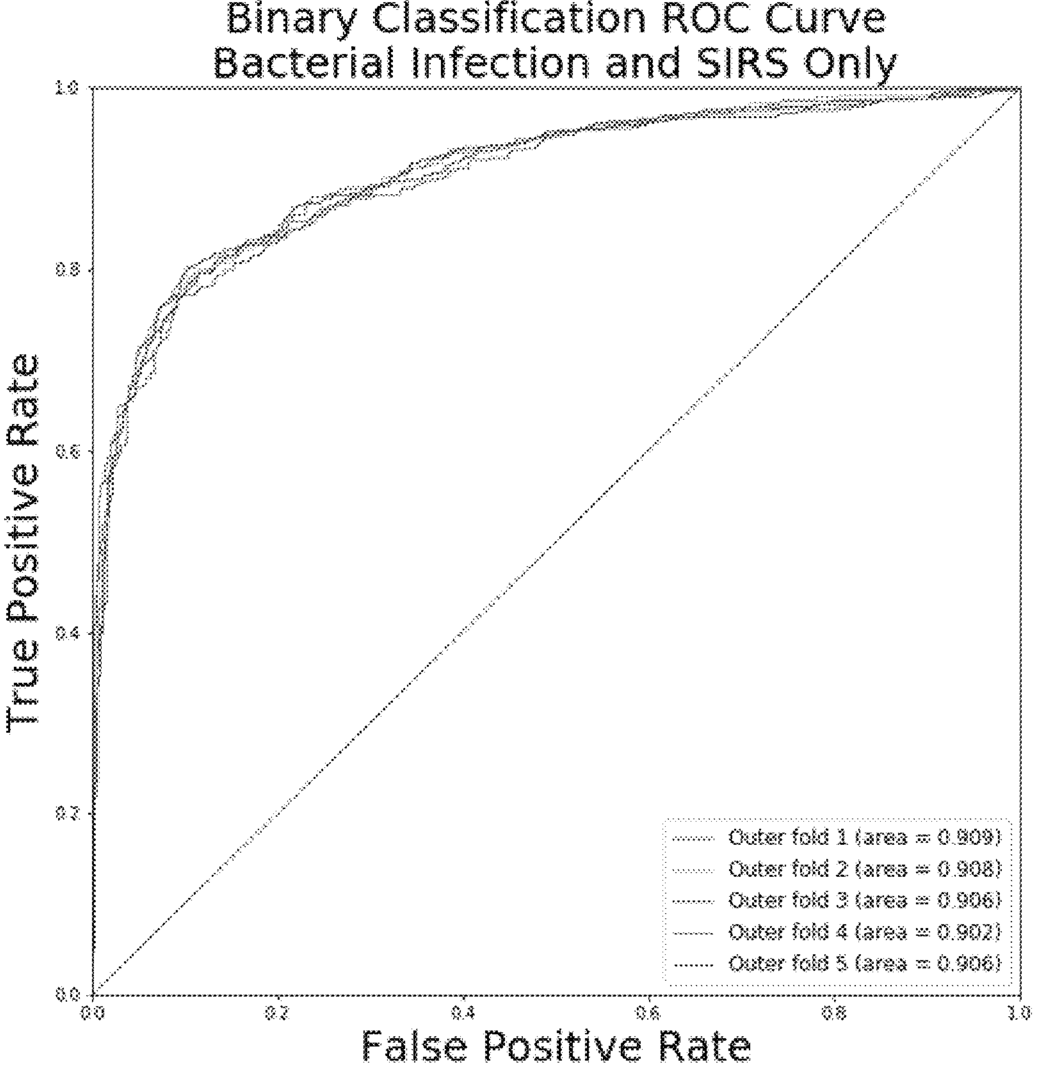
FIG. 12 depicts the five-fold cross validation results for the 16-gene model for classification of positive for sepsis due to bacterial infection versus negative for sepsis (SIRS samples) (Test 3).
Figure 13:
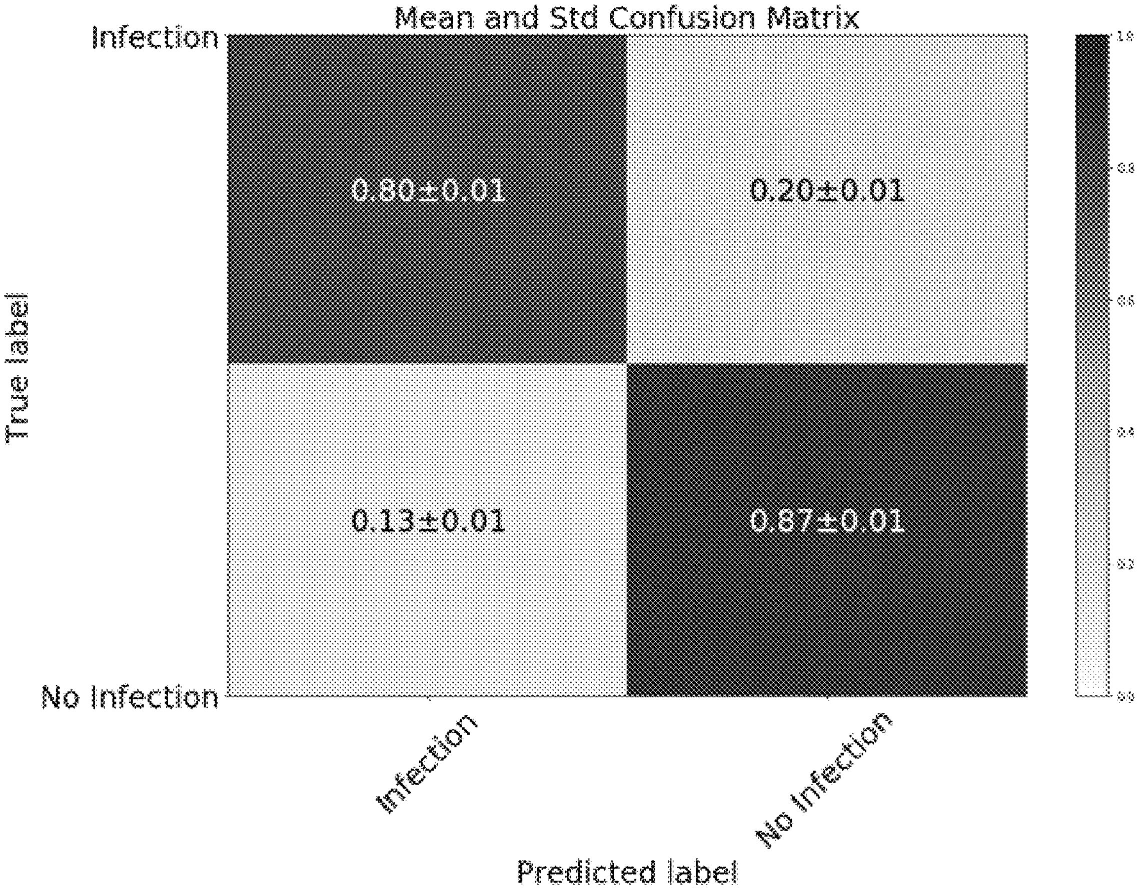
FIG. 13 depicts the confusion matrix for Test 3, with the 16-gene model, for classification of sepsis (due to bacteria) versus no sepsis (SIRS).
Figure 14:
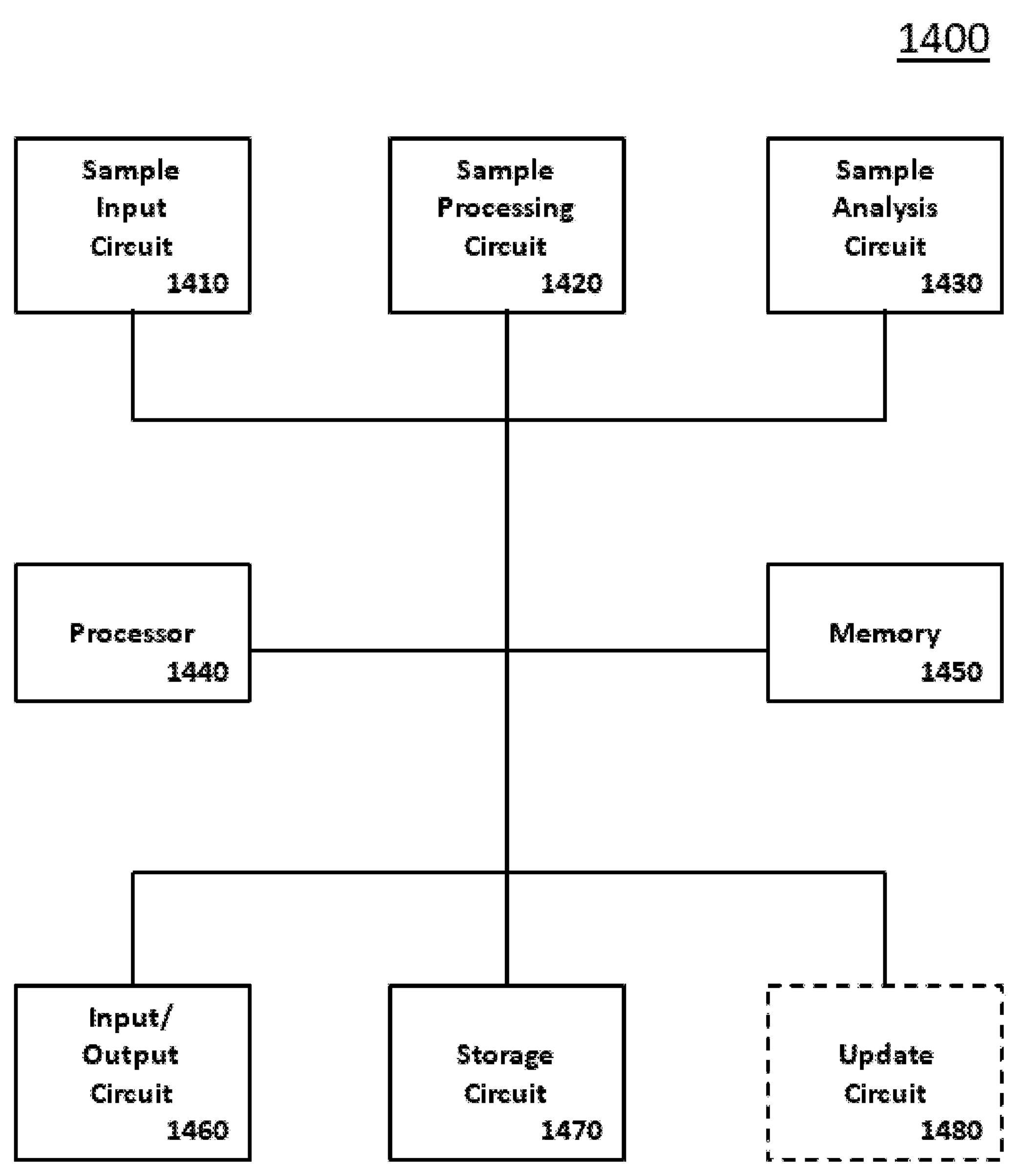
FIG. 14 is a block diagram of a classification system, computer program product, and/or compute-implemented method that may be used in a platform. A classification system 1400, computer program product, and/or computer-implemented method may include a processor subsystem 1440, including one or more Central Processing Units (CPU) on which one or more operating systems and/or one or more applications run. While one processor 1440 is shown, it will be understood that multiple processors 1440 may be present, which may be either electrically interconnected or separate. Processor(s) 1440 are configured to execute computer program code from memory devices, such as memory 1450, to perform at least some of the operations and methods described herein. The storage circuit 1470 may store databases which provide access to the data/parameters/classifiers used by the classification system 1400 such as the signatures, weights, thresholds, etc. An input/output circuit 1460 may include displays and/or user input devices, such as keyboards, touch screens and/or pointing devices. Devices attached to the input/output circuit 1460 may be used to provide information to the processor 1440 by a user of the classification system 1400. Devices attached to the input/output circuit 1460 may include networking or communication controllers, input devices (keyboard, a mouse, touch screen, etc.) and output devices (printer or display). An optional update circuit 1480 may be included as an interface for providing updates to the classification system 1400 such as updates to the code executed by the processor 1440 that are stored in the memory 1450 and/or the storage circuit 1470. Updates provided via the update circuit 1480 may also include updates to portions of the storage circuit 1470 related to a database and/or other data storage format which maintains information for the classification system 1400, such as the signatures, weights, thresholds, etc. The sample input circuit 1410 provides an interface for the classification system 1400 to receive biological samples to be analyzed. The sample processing circuit 1420 may further process the biological sample within the classification system 1400 so as to prepare the biological sample for automated analysis.

Five rounds of cross validation generated 5 values for area under the receiver operating characteristic curves (AUROC) for each of the models (Top 64, 32, and 16 genes). The ranges of the five AUROC values are given for each model (Table 5) and the data for the Top 16 genes is shown in FIG. 12. The accompanying confusion matrix (FIG. 13) demonstrates that the 16 gene model achieved 80% sensitivity and 87% specificity for determining sepsis due to bacterial infection versus no sepsis (SIRS only). The sensitivity and specificity for the other models is summarized in Table 5.

TABLE 5

| # Genes in Model | AUROC Range | Sensitivity (%) | Specificity (%) |
|---|---|---|---|
| 16 | 0.902-0.909 | 80 ± 0.01 | 87 ± 0.01 |
| 32 | 0.912-0.921 | 81 ± 0.01 | 88 ± 0.01 |
| 64 | 0.921-0.932 | 83 ± 0.00 | 90 ± 0.01 |

SUMMARY

Together, these results indicate that for each of the three tests, the sparsest model (Top 16 genes) delivers similar performance characteristics to the less parsimonious models (Top 32 and 64 gene models).

Example 3: Identification of Normalization Genes for qPCR

Common methods for achieving quantitation of RNA include the use of a standard curve and comparative Ct (2-ΔΔCt) method. A number of operations are undertaken to perform real time PCR, necessitating the use of controls to check for assay performance at various stages, including the efficiency of reverse transcription and PCR amplification, and the amount of template mRNA included added to the reaction. In addition, to achieve accurate, repeatable and reliable quantification of gene transcripts, the transcript or cDNA counts, concentration, or level of expression of the genes of interest are compared to the transcript or cDNA counts, level or concentration of at least one endogenous reference gene whose expression does not vary under the experimental conditions or disease state of interest. This normalization procedure can occur in every assay performed as part of the test. Normalization against one or more stable reference or housekeeping genes accounts for assay-to-assay variability in, for example, mRNA extraction efficiency from sample, or in amount of mRNA template in the assays for each gene that will be included in each classifier. RNA transcript normalization removes non-biological variation in each gene transcript level to reveal gene expression variability that is most likely caused by the underlying disease process (e.g., infection, infection by a specific pathogen class, etc.).

A description of the various sources of experimental and sample issues that require the use of a normalization process, and selection of normalization genes, is described by Kozera and Rapacz (J. Appl. Genet. 2013. 54(4), 391-406).

Several potential housekeeping genes were identified during the course of the analyses. These genes are chosen because they have invariant levels regardless of the phenotype, or biological process (e.g., no infection, infection, bacterial infection, viral infection, etc.), and using the following criteria.

The selection of normalization genes was performed using only studies with large sample sizes.

The selected genes were those with low variance due to phenotype and values close to the median expression value for all genes in that dataset.

Gene sets were further filtered by selecting those that are present in our analysis as well as in a literature derived list.

Selected reference genes are listed in Table 6. Additional, or alternative, reference genes, such as, but not limited, HPRT1, may be included in a test implemented on a specific platform to, for example, control for platform-specific features. In some embodiments, a reference gene or reference genes in a test implemented on a specific platform may be selected based on low Ct values, and low coefficients of variation. In some embodiments, the reference gene may be HPRT1 and/or PUM1.

TABLE 6

Selected reference genes

| Reference genes HGNC approved gene symbol | |
|---|---|
| CRCP | CGRP receptor component |
| WDR33 | WD repeat domain 33 |
| HIGD1A | HIG1 hypoxia inducible domain family member 1A |
| DMTF1 | cyclin D binding myb like transcription factor 1 |
| UBE3A | ubiquitin protein ligase E3A |
| G3BP2 | G3BP stress granule assembly factor 2 |
| PUM1 | pumilio RNA binding family member 1 |
| RBBP4 | RB binding protein 4, chromatin remodeling factor |
| HNRNPM | heterogeneous nuclear ribonucleoprotein M |
| ZNF250 | zinc finger protein 250 |

These reference genes, or a subset thereof, may be used for a variety of assays, e.g. infection versus no infection, sepsis due to bacteria versus SIRS, implemented using a variety of assay methodologies, e.g. microarray, qRT-PCR, RNA sequencing, array, on a variety of devices, e.g. TLDA, Nanostring nCounter® platform and, Qvella FAST-ID™.

Example 4: Translation of Signature to a Diagnostic Platform

The aforementioned signatures may be readily adapted for use on any number of testing platforms that may quantitatively or semi-quantitatively measure mRNA expression levels in a sample/biological sample for the genes, or subset thereof, listed in Table 1.

A number of platforms and/or devices that employ these methodologies for detecting and measuring gene products are either commercially available or under development. Examples of these include Pixel™ System, incorporating Molecular Indexing™, developed by CELLULAR RESEARCH, INC.®, NanoString® Technologies nCounter gene expression system; mRNA-Seq, Tag-Profiling, BeadArray™ technology and VeraCode from Illumina, the ICEPlex System from PrimeraDx, the QuantiGene 2.0 Multiplex Assay from Affymetrix and Qvella FAST-ID™ technology. In an embodiment, detection, and quantification of gene expression levels in the methods according to the inventive concept are accomplished by detecting and quantitating mRNA expression levels using Qvella FAST-ID™ technology.

Qvella's innovative method of performing gene expression assays from whole blood samples is described in International PCT Patent Publication No. WO 2018/085928. The assay employs centrifugal processing of samples collected in PAXgene tubes to form complexes of nucleic acids and surfactant (NAS complexes) containing host mRNA. The NAS complexes are centrifugally precipitated, centrifugally washed, and subsequently resuspended in an aqueous resuspension liquid, forming a purified NAS complex suspension. The suspension is then subjected to high amplitude pulsed electric fields and rapid Joule heating (performed via Qvella's e-Lysis method) to dissociate the NAS complexes, releasing the mRNA and forming a nucleic acid solution. The mRNA is then amplified and quantitated by qRT-PCR without the need for nucleic acid extraction. The entire assay workflow is performed in less than an hour and will be fully automated.

As a demonstration of how the Qvella platform measures and applies these methods, and to demonstrate the translation of the gene signatures and classifier development for a specific platform, we developed assays on the FAST-HR qRT-PCR system for 61 infection-diagnostic targets and 2 normalization genes (HPRT1 and PUM1). These two normalization genes were selected from a pool of 8 candidate normalization targets (CRCP, WDR33, DMTF1, UBE3A, HPRT1, G3BP2, PUM1, and ZNF250) based on low Ct values, and low coefficients of variation.

These 63 targets were then measured using the described methods in a cohort of 100 subjects, which included blood samples from 25 patients with bacterial infection, 21 patients with viral infection, 9 patients with fungal infection, 25 patients with systemic inflammatory response syndrome (SIRS) without infection, and 20 healthy patients. These samples were from subjects enrolled in IRB-approved clinical studies.

Figure 15:
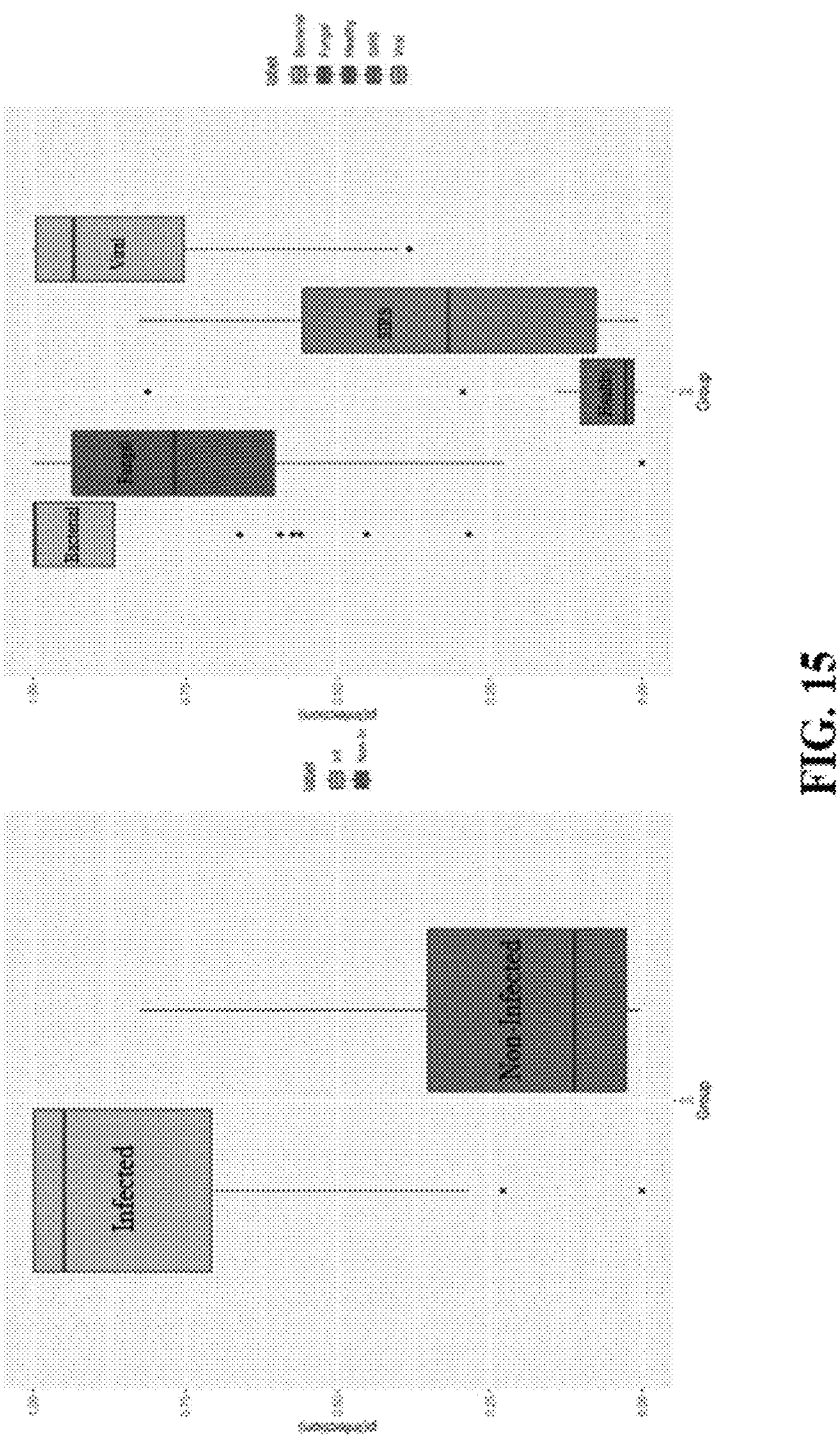
FIG. 15 depicts LOOCV Results for 60 targets: infection (bacterial, viral, or fungal) vs non-infection (SIRS or healthy).

One target had a high missingness rate and so test performance was assessed based on the contribution of 60 discriminating host response genes, normalized using HPRT1 and PUM1. The accuracy and AUC of the test were assessed using leave-one-out cross-validation (LOOCV)

based on its ability to discriminate subjects with infection (bacterial, viral, or fungal) from those without infection (SIRS or healthy) (FIG. 15). Overall accuracy of this test was 0.86 with an AUC of 0.94. The associated confusion matrix is shown in FIG. 16.

Figure 17:
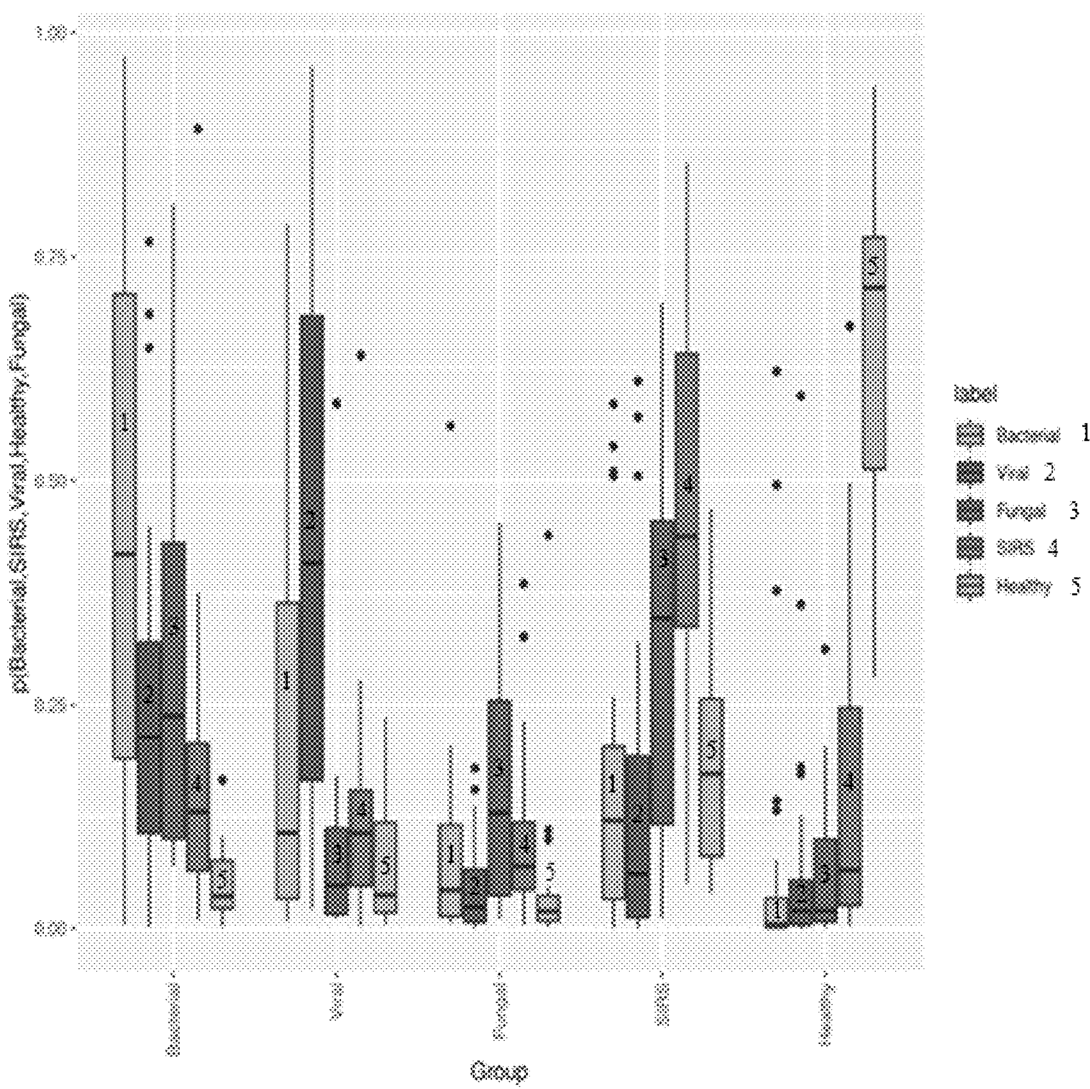
FIG. 17 depicts LOOCV results using 60 of the top 64 gene targets: The results are for individual classifiers developed for each class (bacterial infection, viral infection, fungal infection, SIRS, healthy).

Multiple classifiers were also developed using these same gene targets to discriminate among bacterial infection, viral infection, fungal infection, SIRS, and healthy subjects. The results of the LOOCV analysis are shown in FIG. 17 and the accompanying performance metrics and confusion matrix are shown in FIG. 18.

Using the same methodology, results for smaller numbers of targets (e.g., 16 or 30 targets) were also modeled.

Any patents or publications mentioned in this specification are indicative of the levels of those skilled in the art to which the inventive concept pertains. The patents and publications are herein incorporated by reference to the same extent as if each individual publication was specifically and individually indicated to be incorporated by reference. In case of conflict, the present specification, including definitions, will control.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for detecting a presence or an absence of sepsis in a sample from a biological source, said method comprising:

(a) measuring gene expression levels of a set of genes from said sample; and (b) analyzing said gene expression levels of said set of genes from said sample with a classifier for a presence of sepsis versus an absence of sepsis or a presence of a noninfectious illness/inflammation, wherein the presence of sepsis is indicated when a score derived from said classifier for the presence of sepsis exceeds a cutoff or threshold value indicating the presence of sepsis, or said score falls within a range or band indicating the presence of sepsis, wherein said classifier is generated by selecting gene signatures that differentiate among multiclass phenotypes comprising healthy, non-infectious illness, systemic inflammatory response syndrome (SIRS), bacterial infection, fungal infection, and viral infection, and wherein said classifier takes the form of: P (having condition)=$\Phi(\beta_1 X_1+\beta_2 X_2+ \ldots +\beta_d X_d)$, wherein said condition is an infection, $\Phi(\cdot)$ is a probit link function, $\{\beta_1, \beta_2, \ldots \beta_d\}$ are coefficients, $\{X_1, X_2, \ldots, X_d\}$ are normalized gene expression levels of said set of genes, and d is said number of genes in said set of genes.

2. The method of claim 1, wherein said classifier for the presence of sepsis comprises an iterative determination of an optimized weighting value for each gene target.

3. The method of claim 2, wherein the optimized weighting value for each gene target is determined during training of said classifier, and wherein said training comprises using data from samples from biological sources known to have an infection and from biological sources known to have SIRS.

4. The method of claim 3, wherein said data further comprises data from samples from biological sources known to be healthy.

5. The method of claim 3, wherein said infection comprises a bacterial infection, a viral infection, and/or a fungal infection.

6. The method of claim 2, wherein said analyzing comprises normalizing said gene expression levels of said set of genes against an expression level of one or more reference genes, and comparing a sum of weighted and normalized gene expression levels of said set of genes in said signature to a pre-defined cutoff or threshold value.

7. The method of claim 6, wherein said one or more reference genes is selected from the group consisting of HPRT1, CRCP, WDR33, HIGD1A, DMTF1, UBE3A, G3BP2, PUM1, RBBP4, HNRNPM, and ZNF250, or any combination thereof.

8. The method of claim 1, wherein said gene expression levels of said set of genes are obtained from assaying RNA transcription levels of individual genes in said set.

9. The method of claim 1, wherein said classifier indicative of the presence of sepsis comprises a gene signature for the presence of sepsis.

10. The method of claim 1, wherein said classifier indicative of the absence of sepsis comprises a gene signature for the presence of SIRS.

11. The method of claim 1, further comprising differentiating sepsis from SIRS.

12. The method of claim 1, wherein if the absence of sepsis is determined, said method further comprises determining a presence or an absence of SIRS.

13. The method of claim 1, wherein if the presence of sepsis is determined, said method further comprises determining an infection associated with said sepsis.

14. The method of claim 13, wherein said infection is selected from the group consisting of:

(a) a bacterial infection, (b) a fungal infection, (c) a viral infection, (d) a bacterial infection and a fungal infection, (e) a bacterial infection and a viral infection, (f) a fungal infection and a viral infection, and (g) a bacterial infection, a fungal infection, and a viral infection.

15. The method of claim 1, wherein said set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, ILIRAP, SPSB3, CNIH4, UBE211, GNAI2, STXBP2, KLF6, SERPINB1, BID, SARIB, EVL, CACYBP, VPS53, UGCG, CCL5, RC3H2, MPZL1, CD44, HNMT, POLC3, HNRNPA3, GABARAPL1, TM7SF3, ST3GAL5, PRKARIA, ABHD2, KYNU, TAGLN2, PCYOX1, PSMF1, UNC45A, GMEB1, CD46, BASP1, OGFOD1, MKNK2, RXRA, AKIRIN2, and KIF18, or a subset thereof.

16. The method of claim 1, wherein said set of genes comprises XAF1, DDX58, HPSE, SMOX, IDH1, GRB10, C19orf66, MKRN2, CLN8, MPZL2, ACO1, TRIM5, TRIM25, OGFRL1, EGR1, GBP1, CDC42EP2, ADAP2, CHPT1, SPATS2, PGRMC2, SLC39A8, YWHAH, TNFAIP3, GLRX, IL1RAP, SPSB3, CNIH4, UBE211, GNAI2, STXBP2, and KLF6, or a subset thereof.

17. The method of claim 1, wherein said set of genes comprises XAF1, DDX58, HPSE, SMOX, IDH1, GRB10, C19orf66, MKRN2, CLN8, MPZL2, ACO1, TRIM5, TRIM25, OGFRL1, EGR1, and GBP1, or a subset thereof.

18. The method of claim 1, wherein said sample comprises a blood sample, a sputum sample, a nasopharyngeal swab sample, a nasopharyngeal wash sample, a synovial fluid sample, a cerebrospinal fluid sample, a bronchoalveolar lavage sample, or an endotracheal aspirate sample from said biological source.

19. The method of claim 1, wherein said biological source is a human subject, and wherein said human subject has or is suspected of having sepsis or SIRS.

20. A method for developing a test on a platform to determine a presence or an absence of an infection in a subject, said method comprising:

(a) analyzing expression levels of genes in biological sources on said platform;

(b) selecting a set of genes, wherein genes in said set are selected for having differential gene expression levels among multiclass phenotypes comprising healthy, non-infectious illness, systemic inflammatory response syndrome (SIRS), bacterial infection, fungal infection, and viral infection; and (c) using expression levels of genes in said set of genes to generate a classifier for the presence or the absence of said infection, wherein said classifier is usable in said test to determine the presence or the absence of said infection in said subject on said platform, and wherein said test to determine the presence or the absence of said infection comprises a test to determine a presence or an absence of sepsis, and wherein said classifier takes the form of: P (having condition)=$\Phi(\beta_1 X_1 + \beta_2 X_2 + \ldots + \beta_d X_d)$, wherein said condition is an infection, $\Phi(\cdot)$ is a probit link function, $\{\beta_1, \beta_2, \ldots, B_d\}$ are coefficients, $\{X_1, X_2, \ldots, X_d\}$ are normalized gene expression levels of said set of genes, and d is the number of genes in said set of genes.

* * * * *